(12) United States Patent
Priepke et al.

(10) Patent No.: US 9,676,781 B2
(45) Date of Patent: Jun. 13, 2017

(54) SUBSTITUTED GLYCINAMIDES, PROCESS FOR THEIR MANUFACTURE AND USE THEREOF AS MEDICAMENTS

(71) Applicant: Boehringer Ingelheim International GmbH, Ingelheim am Rhein (DE)

(72) Inventors: Henning Priepke, Warthausen (DE); Georg Dahmann, Warthausen-Birkenhard (DE); Kai Gerlach, Mittelbiberach (DE); Roland Pfau, Biberach an der Riss (DE); Wolfgang Wienen, Biberach an der Riss (DE); Annette Schuler-Metz, Ulm (DE); Sandra Handschuh, Biberach an der Riss (DE); Herbert Nar, Ochsenhausen (DE)

(73) Assignee: Boehringer Ingelheim International GmbH, Ingelhem am Rhein (DE)

( * ) Notice: Subject to any disclaimer, the term of this patent is extended or adjusted under 35 U.S.C. 154(b) by 0 days.

(21) Appl. No.: 14/716,227

(22) Filed: May 19, 2015

(65) Prior Publication Data

US 2015/0252050 A1    Sep. 10, 2015

Related U.S. Application Data

(63) Continuation of application No. 13/785,176, filed on Mar. 5, 2013, now Pat. No. 9,062,034, which is a continuation of application No. 11/993,426, filed as application No. PCT/EP2006/063611 on Jun. 28, 2006, now abandoned.

(30) Foreign Application Priority Data

Jun. 30, 2005   (EP) ..................................... 05014270

(51) Int. Cl.
| | | |
|---|---|---|
| *A61K 31/55* | (2006.01) |
| *C07D 409/12* | (2006.01) |
| *C07D 409/14* | (2006.01) |
| *C07D 487/04* | (2006.01) |
| *C07D 413/14* | (2006.01) |
| *C07D 417/14* | (2006.01) |
| *C07D 471/04* | (2006.01) |
| *C07D 471/08* | (2006.01) |

(52) U.S. Cl.
CPC ......... *C07D 487/04* (2013.01); *C07D 409/12* (2013.01); *C07D 409/14* (2013.01); *C07D 413/14* (2013.01); *C07D 417/14* (2013.01); *C07D 471/04* (2013.01); *C07D 471/08* (2013.01)

(58) Field of Classification Search
CPC ..... A61K 31/55; C07D 409/12; C07D 409/14
USPC ........... 514/212.02, 212.07, 217.01, 217.02; 540/524, 543, 594, 595
See application file for complete search history.

(56) References Cited

U.S. PATENT DOCUMENTS

| | | |
|---|---|---|
| 7,476,663 B2 | 1/2009 | Pfau et al. |
| 7,563,786 B2 | 7/2009 | Priepke et al. |
| 7,732,466 B2 | 6/2010 | Pfau et al. |
| 2003/0153610 A1 | 8/2003 | Straub et al. |
| 2004/0038858 A1 | 2/2004 | Dorsch et al. |
| 2005/0256107 A1 | 11/2005 | Pfau et al. |
| 2006/0052376 A1 | 3/2006 | Dorsch et al. |
| 2006/0069082 A1 | 3/2006 | Priepke et al. |
| 2006/0223826 A1 | 10/2006 | Abe et al. |
| 2006/0293300 A1 | 12/2006 | Pfau et al. |
| 2010/0317848 A1 | 12/2010 | Han et al. |

FOREIGN PATENT DOCUMENTS

| | | |
|---|---|---|
| CA | 2396561 A1 | 7/2001 |
| CA | 2506716 A1 | 6/2004 |
| CA | 2562714 A1 | 11/2005 |
| CA | 2564207 A1 | 11/2005 |
| CA | 2565186 A1 | 11/2005 |
| CA | 2581580 A1 | 4/2006 |
| WO | 0076971 A2 | 12/2000 |
| WO | 0147919 A1 | 7/2001 |
| WO | 0170232 A1 | 9/2001 |
| WO | 02092563 A2 | 11/2002 |
| WO | 2004046138 A1 | 6/2004 |
| WO | 2004108892 A2 | 12/2004 |
| WO | 2005111013 A1 | 11/2005 |
| WO | 2005111014 A1 | 11/2005 |
| WO | 2005111029 A1 | 11/2005 |
| WO | 2006034822 A1 | 4/2006 |
| WO | 2008080891 A2 | 7/2008 |

OTHER PUBLICATIONS

International Search Report for PCT/EP2006/063611 mailed Aug. 10, 2006.
International Search Report for PCT/EP2007/064406 mailed Aug. 13, 2008.
Lavrador, Karine, et al; A New Series of Cyclic Amino Acids as Inhibitors of S-Adenosyl L-Methionine Synthetase; Bioorganic & Medicinal Chemistry Letters (1998) vol. 8 pp. 1629-1634.
Mederski, Werner W.K.R. et al. "Chlorothiophenecarboxamides as P1 surrogates of inhibitors of blood coagulation factor Xa" Bioorganic & Medicinal Chemistry Letters (2004) 14 pgs 5817-5822.

*Primary Examiner* — Brenda Coleman
(74) *Attorney, Agent, or Firm* — Paula K. Wittmayer; David L. Kershner

(57) ABSTRACT

The present invention relates to new substituted glycinamides of general formula (I)

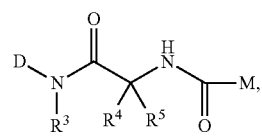

wherein D, M, $R^3$, $R^4$ and $R^5$ are defined as in the specification, the tautomers, enantiomers, diastereomers, mixtures and salts thereof, particularly the physiologically acceptable salts thereof with inorganic or organic acids or bases, which have valuable properties.

8 Claims, No Drawings

SUBSTITUTED GLYCINAMIDES, PROCESS FOR THEIR MANUFACTURE AND USE THEREOF AS MEDICAMENTS

This application is a continuation of U.S. application Ser. No. 13/785,176 filed Mar. 5, 2013 which is now allowed and which is a continuation of U.S. application Ser. No. 11/993,426 filed Apr. 9, 2010 which is a national phase entry under 35 U.S.C. 371 of international application PCT/EP2006/063611, filed Jun. 28, 2006, which claims priority to European Application No. EP 05 014 270.2, filed Jun. 30, 2005, each of which is hereby incorporated by reference in its entirety.

The present invention relates to new substituted glycinamides of general formula (I)

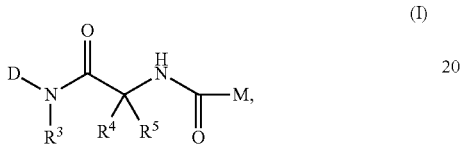

(I)

the tautomers, enantiomers, diastereomers, mixtures and salts thereof, particularly the physiologically acceptable salts thereof with inorganic or organic acids or bases, which have valuable properties.

The compounds of the above general formula (I) as well as the tautomers, enantiomers, diastereomers, mixtures and salts thereof, particularly the physiologically acceptable salts thereof with inorganic or organic acids or bases, and the stereoisomers thereof, have valuable pharmacological properties, particularly an antithrombotic activity and a factor Xa-inhibiting activity.

The present application relates to new compounds of the above general formula (I), the preparation thereof, the pharmaceutical compositions containing the pharmacologically effective compounds, the preparation and use thereof.

A 1st embodiment of the present invention includes those compounds of general formula (I) wherein
D denotes a substituted bicyclic ring system of formula (II),

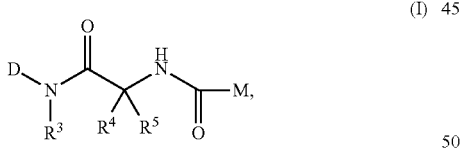

(I)

wherein
$K^1$ and $K^4$
each independently of one another denote a —$CH_2$—, —$CHR^{7a}$—, —$CR^{7b}R^{7c}$— or a —$C(O)$— group, and
$R^{7a}/R^{7b}/R^{7c}$
each independently of one another denote a fluorine atom, a hydroxy, $C_{1-5}$-alkyloxy, tetrahydrofuranyl, oxetanyl, amino, $C_{1-5}$-alkylamino, di-($C_{1-5}$-alkyl)-amino, $C_{3-5}$-cycloalkyleneimino or $C_{1-5}$-alkylcarbonylamino group,
a $C_{1-5}$-alkyl group which may be substituted by 1-3 fluorine atoms, a hydroxy-$C_{1-5}$-alkyl, $C_{1-5}$-alkyloxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl, $C_{4-7}$-cycloalkyleneiminocarbonyl-$C_{0-5}$-alkyl- group,
a phenyl group or a 5- or 6-membered heteroaryl group which may be substituted by 1-2 substituents selected from among a nitro, amino, hydroxy, methoxy, cyano, $C_{1-5}$-alkyl group or a fluorine, chlorine or bromine atom,
wherein the two groups $R^{7b}/R^{7c}$ cannot both simultaneously be bound to the cyclic carbon atom via a heteroatom, except if —$C(R^{7b}R^{7c})$— corresponds to a —$CF_2$ group,
or
two groups $R^{7b}/R^{7c}$ together with the cyclic carbon atom may form a 3, 4, 5-, 6- or 7-membered saturated carbocyclic group or a cyclopentene, cyclohexene, oxetane, azetidine, thietane, tetrahydrofuran, pyrrolidine, tetrahydrothiophene, tetrahydropyran, piperidine, pentamethylene sulphide, hexamethyleneimine, 1,3-dioxolane, 1,4-dioxane, hexahydropyridazine, piperazine, thiomorpholine, morpholine, 2-imidazolidinone, 2-oxazolidinone, tetrahydro-2(1H)-pyrimidinone, [1,3]oxazinan-2-one ring,
wherein the methylene groups thereof may be substituted by 1-2 $C_{1-3}$-alkyl or $CF_3$— groups, and/or
the methylene groups thereof, if they are not bound to a heteroatom, may be substituted by 1-2 fluorine atoms, and/or
wherein a —$CH_2$ group adjacent to an N atom may be replaced by a —CO group, and/or
the imino groups of which may be substituted in each case by a $C_{1-3}$-alkyl or $C_{1-3}$-alkylcarbonyl group, and/or wherein the sulphur atom may be oxidised to form a sulphoxide or sulphone group,
$K^2$ and $K^3$
each independently of one another denote a —$CH_2$, —$CHR^{8a}$, —$CR^{8b}R^{8c}$ or a —$C(O)$— group, and
$R^{8a}/R^{8b}/R^{8c}$
each independently of one another denote a $C_{1-5}$-alkyl group which may be substituted by 1-3 fluorine atoms, a hydroxy-$C_{1-5}$-alkyl, $C_{1-5}$-alkyloxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl, $C_{4-7}$-cycloalkyleneiminocarbonyl-$C_{0-5}$-alkyl group,
or two groups $R^{8b}/R^{8c}$ together with the cyclic carbon atom may form a 3, 4, 5-, 6- or 7-membered saturated carbocyclic group or a cyclopentene, cyclohexene, oxetane, azetidine, thietane, tetrahydrofuran, pyrrolidine, tetrahydrothiophene, tetrahydropyran, piperidine, pentamethylene sulphide, hexamethyleneimine, hexahydropyridazine, tetrahydro-2(1H)-pyrimidinone, [1,3]oxazinan-2-one ring,
wherein the methylene groups thereof may be substituted by 1-2 $C_{1-3}$-alkyl or $CF_3$— groups, and/or the methylene groups thereof, if they are not bound to a heteroatom, may be substituted by 1-2 fluorine atoms, and/or wherein a —CH$_2$ group next to a nitrogen atom may be replaced by a —CO group, and/or
the imino groups of which may be substituted in each case by a C$_{1-3}$-alkyl or C$_{1-3}$-alkylcarbonyl group, and/or wherein the sulphur atom may be oxidised to form a sulphoxide or sulphone group,
with the proviso that a heteroatom introduced by R$^{8b}$ or R$^{8c}$ may not be separated from X in formula (I) by only one carbon atom, and
in all there should be no more than four groups selected from among R$^{7a}$, R$^{7b}$, R$^{7c}$, R$^{8a}$, R$^{8b}$ and R$^{8c}$ in formula (II), and
X denotes an oxygen or sulphur atom, a sulphene, sulphone or an NR$^1$ group, wherein
R$^1$ denotes a hydrogen atom or a hydroxy, C$_{1-3}$-alkyloxy, amino, C$_{1-3}$-alkylamino, di-(C$_{1-3}$-alkyl)-amino, a C$_{1-5}$-alkyl, C$_{2-5}$-alkenyl-CH$_2$, C$_{2-5}$-alkynyl-CH$_2$, C$_{3-6}$-cycloalkyl, C$_{4-6}$-cycloalkenyl, oxetan-3-yl, tetrahydrofuran-3-yl, benzyl, C$_{1-5}$-alkyl-carbonyl, trifluoromethylcarbonyl, C$_{3-6}$-cycloalkyl-carbonyl, C$_{1-5}$-alkyl-sulphonyl, C$_{3-6}$-cycloalkyl-sulphonyl, aminocarbonyl, C$_{1-5}$-alkylaminocarbonyl, di-(C$_{1-5}$-alkyl)-aminocarbonyl, C$_{1-5}$-alkyloxycarbonyl, C$_{4-7}$-cycloalkyleneiminocarbonyl group,
wherein the methylene and methyl groups present in the above-mentioned groups may additionally be substituted by a C$_{1-3}$-alkyl, carboxy, C$_{1-5}$-alkoxycarbonyl group or by a hydroxy, C$_{1-5}$-alkyloxy, amino, C$_{1-5}$-alkylamino, C$_{1-5}$-dialkylamino or C$_{4-7}$-cycloalkyleneimino group, provided that the methylene or methyl groups are not directly bound to a heteroatom selected from among O, N or S, and/or
one to three hydrogen atoms may be replaced by fluorine atoms, provided that the methylene or methyl groups are not directly bound to a heteroatom selected from among O, N or S,
and wherein
A$^1$ denotes either N or CR$^{10}$,
A$^2$ denotes either N or CR$^{11}$,
A$^3$ denotes either N or CR$^{12}$,
wherein R$^{10}$, R$^{11}$ and R$^{12}$ each independently of one another represent
a hydrogen, fluorine, chlorine, bromine or iodine atom, or a C$_{1-5}$-alkyl, CF$_3$, C$_{2-5}$-alkenyl, C$_{2-5}$-alkynyl, a cyano, carboxy, C$_{1-5}$-alkyloxycarbonyl, hydroxy, C$_{1-3}$-alkyloxy, CF$_3$O, CHF$_2$O, CH$_2$FO, amino, C$_{1-5}$-alkylamino, di-(C$_{1-5}$-alkyl)-amino or C$_{4-7}$-cycloalkyleneimino group, or
D denotes one of the four groups (II-1), (II-2), (II-3) or (II-4)

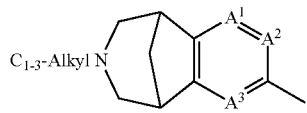

(II-1)

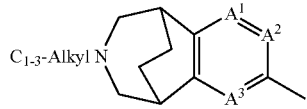

(II-2)

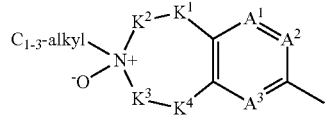

(II-3)

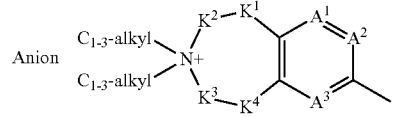

(II-4)

wherein the groups A1, A2, A3, K1, K2, K3, K4 are as hereinbefore defined, and
Anion in (II-4) denotes a fluoride, chloride, bromide, iodide, sulphate, hydrogen sulphate, phosphate, hydrogen phosphate, benzoate, salicylate, succinate, citrate or tartrate,
R$^3$ denotes a hydrogen atom or a C$_{1-3}$-alkyl group, and
R$^4$ and R$^5$ each independently of one another represent
a hydrogen atom,
a straight-chain or branched C$_{1-6}$-alkyl, C$_{2-6}$-alkenyl or C$_{2-6}$-alkynyl group, wherein the hydrogen atoms of the methylene and/or methyl fragments of the straight-chain or branched C$_{1-6}$-alkyl, C$_{2-6}$-alkenyl or C$_{2-6}$-alkynyl group may optionally be wholly or partly replaced by fluorine atoms, and/or
one or two hydrogen atoms of the straight-chain or branched C$_{1-6}$-alkyl, C$_{2-6}$-alkenyl or C$_{2-6}$-alkynyl group in their methylene and/or methyl fragments may optionally each be replaced independently of one another by a C$_{3-7}$-cycloalkyl group, a nitrile, hydroxy or C$_{1-5}$-alkyloxy group,
wherein the hydrogen atoms of the C$_{1-5}$-alkyloxy group may optionally be wholly or partly replaced by fluorine atoms,
an allyloxy, propargyloxy, phenylmethyloxy, phenethyloxy, C$_{1-5}$-alkylcarbonyloxy, C$_{1-5}$-alkyloxycarbonyloxy, carboxy-C$_{1-5}$-alkyloxy, C$_{1-5}$-alkyloxycarbonyl-C$_{1-5}$-alkyloxy, C$_{1-5}$-alkyloxy-C$_{2-5}$-alkyloxy, mercapto, C$_{1-5}$-alkylsulphanyl, C$_{1-5}$-alkylsulphinyl, C$_{1-5}$-alkylsulphonyl, carboxy, C$_{1-5}$-alkyloxycarbonyl, aminocarbonyl, C$_{1-5}$-alkylaminocarbonyl, di-(C$_{1-5}$-alkyl)-aminocarbonyl, C$_{1-5}$-alkyl-aminocarbonyloxy, di-(C$_{1-5}$-alkyl)-aminocarbonyloxy, C$_{4-7}$-cycloalkyleneiminocarbonyl, aminosulphonyl, C$_{1-5}$-alkylaminosulphonyl, di-(C$_{1-5}$-alkyl)-aminosulphonyl, C$_{4-7}$-cycloalkyleneiminosulphonyl, di-(C$_{1-5}$-alkyl)-phosphoryl, amino, C$_{1-5}$-alkylamino, di-(C$_{1-5}$-alkyl)-amino, C$_{1-5}$-alkylcarbonylamino, trifluoracetylamino, C$_{1-5}$-alkyloxy-C$_{1-5}$-alkylcarbonylamino, phenylcarbonylamino, C$_{1-5}$-alkylaminocarbonylamino, di-(C$_{1-5}$-alkyl)-aminocarbonylamino, C$_{1-5}$-alkyloxy-carbonylamino, phenylmethyloxy-carbonylamino, C$_{1-5}$-alkyloxy-C$_{2-5}$-alkyloxy-C$_{1-2}$-alkylcarbonylamino, C$_{1-5}$-alkylsulphonylamino, N—(C$_{1-5}$-alkylsulphonyl)-C$_{1-5}$-alkylamino, C$_{3-6}$-cycloalkylcarbonylamino group, 4-morpholinocarbonylamino, or a morpholinyl, thiomorpholinyl, pyrrolidinyl, piperidinyl, piperazinyl, tetrahydrofuranyl, tetrahydropyranyl group,
wherein the above-mentioned carbo- and heterocycles in the ring may each be substituted by 1 to 4 C$_{1-3}$-alkyl or C$_{1-3}$-alkylcarbonyl groups or may each be substituted by 1 or 2 oxo groups, and/or
the above-mentioned phenyl and heteroaryl groups may be replaced by 1 or 2 substituents selected from among fluorine, chlorine, bromine, methyl, methoxy, amino or trifluoromethyl or two adjacent carbon atoms of a phenyl ring may be substituted by a —CH$_2$—O—CH$_2$ group, and/or the above-mentioned alkyl groups may be substituted by a cyano-C$_{1-5}$-alkyloxycarbonyl or carboxy group,
   wherein the above-mentioned carboxylic acid or sulphonic acid amide may optionally be additionally substituted at the nitrogen by a C$_{1-5}$-alkyl group,
   and/or the hydrogen atoms of the sp$^2$-hybridised carbon atoms of the straight-chain or branched C$_{2-6}$-alkenyl group may optionally be wholly or partly replaced by fluorine atoms,
a carboxy, aminocarbonyl, C$_{1-5}$-alkylaminocarbonyl, C$_{3-6}$-cycloalkylaminocarbonyl, di-(C$_{1-5}$-alkyl)-aminocarbonyl, C$_{1-5}$-alkyloxycarbonyl, C$_{4-7}$-cycloalkyleneiminocarbonyl group,
a phenyl, mono- or bicyclic heteroaryl, phenyl-C$_{1-5}$-alkyl or mono- or bicyclic heteroaryl-C$_{1-5}$-alkyl group,
   which may optionally be mono- to trisubstituted in the phenyl or heteroaryl moiety by identical or different substituents selected from among fluorine, chlorine, bromine and iodine atoms, and C$_{1-5}$-alkyl, trifluoromethyl, benzyl, amino, nitro, C$_{1-5}$-alkyl-amino, di-(C$_{1-5}$-alkyl)-amino, hydroxy, C$_{1-5}$-alkyloxy, mono-, di- or trifluoromethoxy, carboxy- and C$_{1-5}$-alkyloxycarbonyl group, or two adjacent carbon atoms of a phenyl ring may be substituted by a —CH$_2$—O—CH$_2$ group,
or
a C$_{3-7}$cycloalkyl, morpholinyl, thiomorpholinyl, pyrrolidinyl, piperidinyl, piperazinyl, tetrahydrofuranyl, tetrahydropyranyl group,
   which may optionally be substituted by one to two groups selected independently of one another from among C$_{1-3}$-alkyl, acetyl, C$_{1-5}$-alkyloxycarbonyl, and hydroxycarbonyl, or
R$^4$ and R$^5$ together with the carbon atom to which they are bound,
   form a C$_{3-7}$-cycloalkyl or C$_{5-7}$-cycloalkenyl group,
   wherein one of the methylene groups of a C$_{4-7}$-cycloalkyl group may be replaced by an oxygen or sulphur atom or an —NH, —N(C$_{1-5}$-alkyl), —N(C$_{1-4}$-alkylcarbonyl), —N(C$_{1-4}$-alkyloxycarbonyl)- or a carbonyl, sulphinyl or sulphonyl group, and/or
   two directly adjacent methylene groups of a C$_{4-7}$-cycloalkyl group may together be replaced by a —C(O)NH, —C(O)N(C$_{1-5}$-alkyl), —S(O)$_2$NH, or —S(O)$_2$N(C$_{1-5}$-alkyl) group, and/or
   1 to 3 carbon atoms of a C$_{3-7}$-cycloalkyl group may each optionally be substituted independently of one another by one or two fluorine atoms or one or two C$_{1-5}$-alkyl groups or a hydroxy, C$_{1-5}$-alkyloxy, formyloxy, C$_{1-5}$-alkylcarbonyloxy, C$_{1-5}$-alkylsulphanyl, C$_{1-5}$-alkylsulphonyl, aminosulphonyl, C$_{1-5}$-alkylaminosulphonyl, di-(C$_{1-5}$-alkyl)-aminosulphonyl, C$_{4-7}$-cycloalkyleneiminosulphonyl, amino, C$_{1-5}$-alkylamino, di-(C$_{1-5}$-alkyl)-amino, C$_{1-5}$-alkylcarbonylamino, C$_{1-5}$-alkylsulphonylamino, N—(C$_{1-5}$-alkylsulphonyl)-C$_{1-5}$-alkylamino, C$_{3-6}$-cycloalkylcarbonylamino, Nitril, carboxy-C$_{1-5}$-alkyl, C$_{1-5}$-alkyloxycarbonyl-C$_{1-5}$-alkyl, carboxy, C$_{1-5}$-alkyloxycarbonyl, aminocarbonyl, C$_{1-5}$-alkylaminocarbonyl, di-(C$_{1-5}$-alkyl)-aminocarbonyl or C$_{4-7}$-cycloalkyleneiminocarbonyl group, and/or
   1 to 2 carbon atoms of a C$_{5-7}$-cycloalkenyl group may optionally be substituted independently of one another by in each case a C$_{1-5}$-alkyl, nitrile, carboxy-C$_{1-5}$-alkyl, C$_{1-5}$-alkyloxycarbonyl-C$_{1-5}$-alkyl, carboxy, C$_{1-5}$-alkyloxycarbonyl, aminocarbonyl, C$_{1-5}$-alkylaminocarbonyl, di-(C$_{1-5}$-alkyl)-aminocarbonyl, C$_{3-6}$-cycloalkyleneiminocarbonyl, aminosulphonyl, C$_{1-5}$-alkylaminosulphonyl, di-(C$_{1-5}$-alkyl)-aminosulphonyl, C$_{3-6}$-cycloalkyleneiminosulphonyl groups or 1-2 fluorine atoms, and/or 1 to 2 carbon atoms of a C$_{4-7}$-cycloalkenyl group which are not bound to another carbon atom by a double bond, may optionally be substituted independently of one another by a hydroxy, C$_{1-5}$-alkyloxy, C$_{1-5}$-alkylcarbonyloxy, C$_{1-5}$-alkylsulphanyl, C$_{1-5}$-alkylsulphonyl, amino, C$_{1-5}$-alkylamino, di-(C$_{1-5}$-alkyl)-amino, C$_{1-5}$-alkylcarbonylamino, C$_{1-5}$-alkylsulphonylamino, N—(C$_{1-5}$-alkylsulphonyl)-C$_{1-5}$-alkylamino or C$_{3-6}$-cycloalkylcarbonylamino groups,
with the proviso that a C$_{3-7}$-cycloalkyl or C$_{5-7}$-cycloalkenyl group of this kind formed from R$^4$ and R$^5$ together,
   wherein two heteroatoms in the cyclic group selected from among oxygen and nitrogen are separated from one another by precisely one optionally substituted —CH$_2$ group, and/or
   wherein one or both methylene groups of the cyclic group which are joined directly to the carbon atom to which the groups R$^4$ and R$^5$ are linked, are replaced by a heteroatom selected from among oxygen, nitrogen and sulphur, and/or
   wherein a substituent bound to the cyclic group, which is characterised in that a heteroatom selected from among oxygen, nitrogen, sulphur and fluorine is bound directly to the cyclic group, is separated from one other heteroatom selected from among oxygen, nitrogen and sulphur, with the exception of the sulphone group, by precisely one, optionally substituted, methylene group, and/or
   wherein two atoms in the ring form an —O—O or —S—O— bond,
is excluded,
M denotes a thiophene ring according to formula (III),

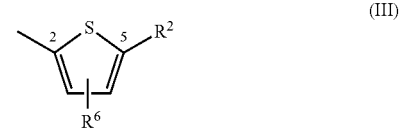

(III)

which is bound to the carbonyl group in formula (I) via the 2-position and which is substituted the in 5-position by R$^2$ and optionally additionally by R$^6$, wherein
R$^2$ denotes a hydrogen, fluorine, chlorine, bromine or iodine atom or a methoxy, C$_{1-2}$-alkyl, formyl, NH$_2$CO or ethynyl group,
R$^6$ denotes a hydrogen, fluorine, chlorine, bromine or iodine atom or a C$_{1-2}$-alkyl or amino group,
wherein, unless otherwise stated, the term "heteroaryl group" mentioned hereinbefore in the definitions denotes a monocyclic 5- or 6-membered heteroaryl group, wherein
   the 6-membered heteroaryl group contains one, two or three nitrogen atoms, and
   the 5-membered heteroaryl group contains an imino group optionally substituted by a C$_{1-3}$-alkyl group, or an oxygen or sulphur atom, or
      an imino group optionally substituted by a C$_{1-3}$-alkyl group or an oxygen or sulphur atom and additionally one or two nitrogen atoms, or
      an imino group optionally substituted by a C$_{1-3}$-alkyl group and three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group phenyl ring may be fused to the above-mentioned monocyclic heteroaryl groups via two adjacent carbon atoms, and the bond is effected via a nitrogen atom or a carbon atom of the heterocyclic moiety or a fused-on phenyl ring, and wherein, unless otherwise stated, by the term "halogen atom" mentioned hereinbefore in the definitions is meant an atom selected from among fluorine, chlorine, bromine and iodine, and wherein the alkyl, alkenyl, alkynyl and alkyloxy groups contained in the previously mentioned definitions which have more than two carbon atoms may, unless otherwise stated, be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, enantiomers, diastereomers, mixtures and salts thereof.

Examples of monocyclic heteroaryl groups are the pyridyl, N-oxy-pyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thiophenyl, thiazolyl, isothiazolyl, [1,2,3]thiadiazolyl, [1,2,4]thiadiazolyl or [1,2,5]thiadiazolyl group.

Examples of bicyclic heteroaryl groups are the benzimidazolyl, benzofuranyl, benzo[c]furanyl, benzothiophenyl, benzo[c]thiophenyl, benzothiazolyl, benzo[c]-isothiazolyl, benzo[d]isothiazolyl, benzooxazolyl, benzo[c]isoxazolyl, benzo[d]-isoxazolyl, benzo[1,2,5]oxadiazolyl, benzo[1,2,5]thiadiazolyl, benzo[1,2,3]thiadiazolyl, benzo[d][1,2,3]triazinyl, benzo[1,2,4]triazinyl, benzotriazolyl, cinnolinyl, quinolinyl, N-oxy-quinolinyl, isoquinolinyl, quinazolinyl, N-oxy-quinazolinyl, quinoxalinyl, phthalazinyl, indolyl, isoindolyl or 1-oxa-2,3-diaza-indenyl group.

Examples of the $C_{1-6}$-alkyl groups mentioned hereinbefore in the definitions are the methyl, ethyl, 1-propyl, 2-propyl, n-butyl, sec-butyl, tert-butyl, 1-pentyl, 2-pentyl, 3-pentyl, neo-pentyl, 3-methyl-2-butyl, 1-hexyl, 2-hexyl, 3-hexyl, 3-methyl-2-pentyl, 4-methyl-2-pentyl, 3-methyl-3-pentyl, 2-methyl-3-pentyl, 2,2-dimethyl-3-butyl or 2,3-dimethyl-2-butyl group.

Examples of the $C_{1-5}$-alkyloxy groups mentioned hereinbefore in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy or neo-pentyloxy group.

Examples of the $C_{2-5}$-alkenyl groups mentioned hereinbefore in the definitions are the ethenyl, 1-propen-1-yl, 2-propen-1-yl, 1-buten-1-yl, 2-buten-1-yl, 3-buten-1-yl, 1-penten-1-yl, 2-penten-1-yl, 3-penten-1-yl, 4-penten-1-yl, 1-hexen-1-yl, 2-hexen-1-yl, 3-hexen-1-yl, 4-hexen-1-yl, 5-hexen-1-yl, but-1-en-2-yl, but-2-en-2-yl, but-1-en-3-yl, 2-methyl-prop-2-en-1-yl, pent-1-en-2-yl, pent-2-en-2-yl, pent-3-en-2-yl, pent-4-en-2-yl, pent-1-en-3-yl, pent-2-en-3-yl, 2-methyl-but-1-en-1-yl, 2-methyl-but-2-en-1-yl, 2-methyl-but-3-en-1-yl or 2-ethyl-prop-2-en-1-yl group.

Examples of the $C_{2-5}$-alkynyl groups mentioned hereinbefore in the definitions are the ethynyl, 1-propynyl, 2-propynyl, 1-butyn-1-yl, 1-butyn-3-yl, 2-butyn-1-yl, 3-butyn-1-yl, 1-pentyn-1-yl, 1-pentyn-3-yl, 1-pentyn-4-yl, 2-pentyn-1-yl, 2-pentyn-3-yl, 3-pentyn-1-yl, 4-pentyn-1-yl, 2-methyl-1-butyn-4-yl, 3-methyl-1-butyn-1-yl or 3-methyl-1-butyn-3-yl group.

A 2nd embodiment of the present invention includes those compounds of general formula (I), wherein
D denotes a substituted bicyclic ring system of formula (II),

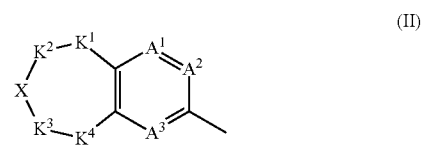

(II)

wherein
$K^1$ and $K^4$
each independently of one another denote a —$CH_2$, —$CHR^{7a}$, —$CR^{7b}R^{7c}$ or a —C(O) group, wherein $R^{7a}/R^{7b}/R^{7c}$
each independently of one another denote a fluorine atom, a hydroxy, $C_{1-5}$-alkyloxy group, a $C_{1-5}$-alkyl group which may be substituted by 1-3 fluorine atoms, a hydroxy-$C_{1-5}$-alkyl, $C_{1-5}$-alkyloxy-$C_{1-5}$-alkyl group, or a phenyl group which may be substituted by 1-2 substituents selected from among a nitro, amino, hydroxy-methoxy, cyano, $C_{1-5}$-alkyl group or a fluorine, chlorine or bromine atom, or a 5- or 6-membered heteroaryl group,
wherein the two groups $R^{7b}/R^{7c}$ cannot both simultaneously be bound to the cyclic carbon atom via a heteroatom, except if —C($R^{7b}R^{7c}$)— corresponds to a —$CF_2$ group, or two groups $R^{7b}/R^{7c}$ may form, together with the cyclic carbon atom, a 3-, 4-, 5-, 6- or 7-membered saturated carbocyclic group or a cyclopentene, cyclohexene, oxetane, tetrahydrofuran or tetrahydropyran ring,
wherein the methylene groups thereof may be substituted by 1-2 $C_{1-3}$-alkyl or $CF_3$— groups, and/or the methylene groups thereof, if they are not bound to a heteroatom, may be substituted by 1-2 fluorine atoms, and $K^2$ and $K^3$
each independently of one another represent a —$CH_2$, —$CHR^{8a}$, —$CR^{8b}R^{8c}$ or a —C(O)— group, and $R^{8a}/R^{8b}/R^{8c}$
each independently of one another denote a $C_{1-5}$-alkyl group which may be substituted by 1-3 fluorine atoms, a hydroxy-$C_{1-5}$-alkyl, $C_{1-5}$-alkyloxy-$C_{1-5}$-alkyl group,
or two groups $R^{8b}/R^{8c}$ may form, together with the cyclic carbon atom, a 3-, 4-, 5-, 6- or 7-membered carbocyclic group or a cyclopentene, cyclohexene, oxetane, tetrahydrofuran, tetrahydropyran ring,
wherein the methylene groups thereof may be substituted by 1-2 $C_{1-3}$-alkyl or $CF_3$— groups, and/or
the methylene groups thereof, if they are not bound to a heteroatom, may be substituted by 1-2 fluorine atoms, with the proviso that a heteroatom introduced by $R^{8b}$ or $R^{8c}$ must not be separated from X in formula (I) by only one carbon atom, and in all in formula (II) there should be no more than four groups selected from among $R^{7a}$, $R^{7b}$, $R^{7c}$, $R^{8a}$, $R^{8b}$ and $R^{8c}$, and X denotes an oxygen or sulphur atom, a sulphene, sulphone or an $NR^1$ group, wherein $R^1$ denotes a hydrogen atom or a $C_{1-5}$-alkyl, $C_{2-5}$-alkenyl-$CH_2$, $C_{2-5}$-alkynyl-$CH_2$, $C_{3-6}$-cycloalkyl, $C_{4-6}$-cycloalkenyl, oxetan-3-yl, tetrahydrofuran-3-yl, benzyl, $C_{1-5}$-alkyl-carbonyl, trifluoromethylcarbonyl, $C_{3-6}$-cycloalkyl-carbonyl, $C_{1-5}$-alkyl-sulphonyl, $C_{3-6}$-cycloalkyl-sulphonyl, aminocarbonyl, $C_{1-5}$-alkylaminocarbonyl, di-($C_{1-5}$-alkyl)-aminocarbonyl, $C_{1-5}$-alkyloxycarbonyl, $C_{4-7}$-cycloalkyleneiminocarbonyl group, wherein the methylene and methyl groups present in the above-mentioned groups may additionally be substituted by a $C_{1-3}$-alkyl, carboxy, $C_{1-5}$-alkoxycarbonyl group or by a hydroxy, $C_{1-5}$-alkyloxy, amino, $C_{1-5}$-alkylamino, $C_{1-5}$-dialkylamino or $C_{4-7}$-cycloalkyleneimino group, provided that the methylene or methyl groups are not directly bound to a heteroatom selected from among O, N or S, and/or one to three hydrogen atoms may be replaced by fluorine atoms, provided that the methylene or methyl groups are not directly bound to a heteroatom selected from among O, N or S, and wherein $A^1$, $A^2$, and $A^3$ are each defined as described in the 1st embodiment, or D denotes one of the four groups (II-1a), (II-2a), (II-3) or (II-4)

(II-1a)

(II-2a)

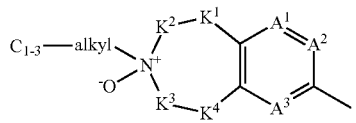

(II-3)

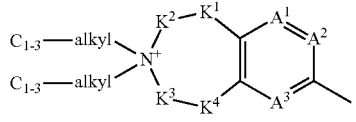

(II-4)

wherein the groups A1, A2, A3, K1, K2, K3, K4 are as hereinbefore defined, and

Anion in (II-4) denotes a fluoride, chloride, bromide, iodide, sulphate, hydrogen sulphate, phosphate, hydrogen phosphate, benzoate, salicylate, succinate, citrate or tartrate, and $R^3$ denotes a hydrogen atom, and $R^4$, $R^5$ and M are each defined as described in the 1st embodiment, the tautomers, enantiomers, diastereomers, mixtures and salts thereof.

A 3rd embodiment of the present invention includes those compounds of general formula (I), wherein D denotes a substituted bicyclic ring system of formula (II),

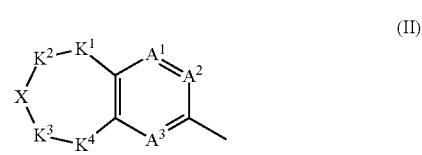

(II)

wherein

K1, K2, K3 and K4 are defined as described in the 1st or 2nd embodiment, and

X denotes an $NR^1$ group, wherein $R^1$ denotes a hydrogen atom or a $C_{1-5}$-alkyl, $C_{2-5}$-alkenyl-$CH_2$, $C_{2-5}$-alkynyl-$CH_2$, $C_{3-6}$-cycloalkyl, $C_{4-6}$-cycloalkenyl group, wherein the methylene and methyl groups present in the above-mentioned groups may additionally be substituted by a $C_{1-3}$-alkyl, carboxy, $C_{1-5}$-alkoxycarbonyl group or by a hydroxy, $C_{1-5}$-alkyloxy, amino, $C_{1-5}$-alkylamino, $C_{1-5}$-dialkylamino or $C_{4-7}$-cycloalkyleneimino group, provided that the methylene or methyl groups are not directly bound to a heteroatom selected from among O, N or S, and/or one to three hydrogen atoms may be replaced by fluorine atoms, so long as the methylene or methyl groups are not directly bound to the nitrogen atom, and wherein $A^1$ denotes either N or $CR^{10}$, $A^2$ denotes either N or $CR^{11}$, $A^3$ denotes either N or $CR^{12}$, wherein $R^{10}$, $R^{11}$ and $R^{12}$ each independently of one another represent a hydrogen, fluorine, chlorine, bromine atom or a $C_{1-5}$-alkyl, $CF_3$, a cyano, carboxy, $C_{1-5}$-alkyloxycarbonyl, hydroxy, $C_{1-3}$-alkyloxy, $CF_3O$, $CHF_2O$, $CH_2FO$— group, or D denotes one of the four groups (II-1a), (II-2a), (II-3) or (II-4)

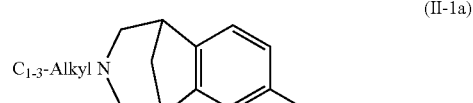

(II-1a)

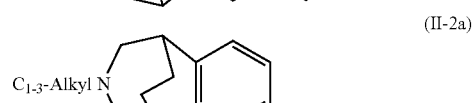

(II-2a)

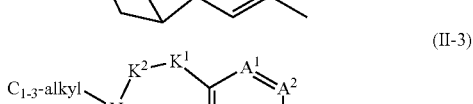

(II-3)

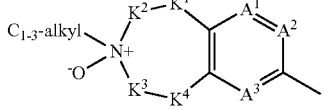

-continued

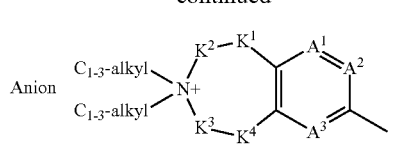
(II-4)

wherein the groups A1, A2, A3, K1, K2, K3, K4 are as hereinbefore defined, and Anion in (II-4) may be selected from among fluoride, chloride, bromide, iodide, sulphate, phosphate, benzoate, salicylate, succinate, citrate and tartrate, and
$R^3$, $R^4$, $R^5$ and M are each defined as in the 1st or 2nd embodiment, wherein $R^6$ denotes a hydrogen atom, the tautomers, enantiomers, diastereomers, mixtures and salts thereof.

A 4th embodiment of the present invention includes those compounds of general formula (I), wherein
D, $R^3$ and M are each defined as in the 1st, 2nd or 3rd embodiment, and
$R^4$ denotes a straight-chain or branched $C_{3-6}$-alkenyl or $C_{3-6}$-alkynyl group,
a straight-chain or branched $C_{1-6}$-alkyl group,
wherein the hydrogen atoms of the straight-chain or branched $C_{1-6}$-alkyl group may optionally be wholly or partly replaced by fluorine atoms,
and wherein optionally one to two hydrogen atoms may be replaced independently of one another by a $C_{3-7}$-cycloalkyl, hydroxy, $C_{1-5}$-alkyloxy, phenylmethyloxy, phenethyloxy, carboxy-$C_{1-5}$-alkyloxy, $C_{1-5}$-alkyloxycarbonyl-$C_{1-5}$-alkyloxy, $C_{1-5}$-alkyloxy-$C_{2-5}$-alkyloxy, $C_{1-5}$-alkylsulphanyl, $C_{1-5}$-alkylsulphinyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{1-5}$-alkyl-aminocarbonyloxy, di-($C_{1-5}$-alkyl)-aminocarbonyloxy, $C_{4-7}$-cycloalkyleneiminocarbonyl, amino, $C_{1-5}$-alkylamino or di-($C_{1-5}$-alkyl)-amino group $C_{1-5}$-alkylcarbonylamino, trifluoracetylamino, $C_{1-5}$-alkyloxy-$C_{1-5}$-alkylcarbonylamino, phenylcarbonylamino, $C_{1-5}$-alkylaminocarbonylamino, di-($C_{1-5}$-alkyl)-aminocarbonylamino, $C_{1-5}$-alkyloxy-carbonylamino, phenylmethyloxycarbonylamino, $C_{1-5}$-alkyloxy-$C_{2-5}$-alkyloxy-$C_{1-2}$ alkylcarbonylamino, $C_{1-5}$-alkylsulphonylamino, $C_{3-6}$-cycloalkylcarbonylamino group, 4-morpholinocarbonylamino- group,
wherein the above-mentioned carbo- and heterocycles in the ring may each be substituted by 1 to 4 $C_{1-3}$-alkyl or $C_{1-3}$-alkylcarbonyl groups or may each be substituted by 1 or 2 oxo groups, and/or
the above-mentioned phenyl and heteroaryl groups may be replaced by 1 to 2 substituents selected from among fluorine, chlorine, bromine, methyl, methoxy, or trifluoromethyl, or two adjacent carbon atoms of a phenyl ring may be substituted by a —$CH_2$—O—$CH_2$ group, and/or the above-mentioned alkyl groups may be substituted by a cyano-$C_{1-5}$-alkyloxycarbonyl or carboxy group,
wherein the above-mentioned carboxylic acid or sulphonic acid amide may optionally additionally be substituted at the nitrogen by a $C_{1-5}$-alkyl group,
a phenyl, phenyl-$C_{1-2}$-alkyl, heteroaryl-$C_{1-2}$-alkyl or C-linked heteroaryl group, wherein the heteroaryl group is selected from among imidazolyl, furanyl, thiophenyl, thiazolyl, pyrazolyl, tetrazolyl, benzimidazolyl, indolyl, pyrimidinyl, pyrazinyl-oxazolyl, 1,2,4-triazolyl and pyridinyl, and which may optionally be mono- to disubstituted in the phenyl or heteroaryl moiety by identical or different substituents selected from among chlorine or fluorine atoms or $C_{1-3}$-alkyl, benzyl, hydroxy, amino, $CF_3$, $CH_3O$— or $CHF_2O$— groups,
$R^5$ denotes a hydrogen atom, a straight-chain or branched $C_{1-4}$-alkyl group, wherein the hydrogen atoms of the straight-chain or branched $C_{1-4}$-alkyl groups may optionally be wholly or partly replaced by fluorine atoms, or a propargyl or $C_{1-3}$alkyloxy-$C_{1-3}$-alkyl group, or
$R^4$ and $R^5$ together with the carbon atom to which they are bound,
form a $C_{5-6}$-cycloalkenyl or $C_{3-7}$-cycloalkyl group,
wherein one of the methylene groups of a $C_{4-7}$-cycloalkyl group may be replaced by an oxygen or sulphur atom or an —NH—, —N($C_{1-5}$-alkyl), —N($C_{1-4}$-alkylcarbonyl), carbonyl, sulphinyl or a sulphonyl group, or two immediately adjacent methylene groups of a $C_{4-7}$-cycloalkyl group may together be replaced by a —C(O)NH, —C(O)N($C_{1-5}$-alkyl), —S(O)$_2$NH— or —S(O)$_2$N($C_{1-5}$-alkyl) group,
and/or 1 to 2 carbon atoms of a $C_{3-7}$-cycloalkyl group may optionally be substituted independently of one another by in each case one or two fluorine atoms or one or two $C_{1-5}$-alkyl groups or a hydroxy, $C_{1-5}$-alkyloxy, formyloxy, amino, $C_{1-5}$-alkylamino, di-($C_{1-5}$-alkyl)-amino, $C_{1-5}$-alkylcarbonylamino, $C_{3-6}$-cycloalkylcarbonylamino, nitrile, carboxy, $C_{1-5}$-alkyloxycarbonyl, aminocarbonyl, $C_{1-5}$-alkylaminocarbonyl, di-($C_{1-5}$-alkyl)-aminocarbonyl or $C_{4-7}$-cycloalkyleneiminocarbonyl group,
with the proviso that a $C_{3-7}$-cycloalkyl group of this kind, formed from $R^4$ and $R^5$ together,
wherein two heteroatoms in the cyclic group selected from among oxygen and nitrogen are separated from one another by precisely one optionally substituted —$CH_2$ group, and/or
wherein one or both methylene groups of the cyclic group which are joined directly to the carbon atom to which the groups $R^4$ and $R^5$ are bound, are replaced by a heteroatom selected from among oxygen, nitrogen and sulphur, and/or
wherein a substituent bound to the cyclic group, which is characterised in that a heteroatom selected from among oxygen, nitrogen, sulphur and fluorine atom is bound directly to the cyclic group, is separated from another heteroatom selected from among oxygen, nitrogen and sulphur by precisely one optionally substituted methylene group, and/or wherein two atoms in the ring form a —O—O or —S—O— bond,
is excluded,
the tautomers, enantiomers, diastereomers, mixtures and salts thereof.

A 5th embodiment of the present invention includes those compounds of general formula (I), wherein
D denotes a substituted bicyclic ring system of formula (II),

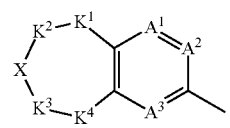
(II)

wherein

K¹ and K⁴
each independently of one another represent a —CH₂, —CHR$^{7a}$ or a —CR$^{7b}$R$^{7c}$— group, wherein R$^{7a}$/R$^{7b}$/R$^{7c}$
each independently of one another denote a $C_{1-2}$-alkyl group or a phenyl group which may be substituted by 1 or 2 substituents selected from among a nitro, amino, hydroxyl, methoxy, cyano, $C_{1-5}$-alkyl group or a fluorine, chlorine or bromine atom, K² and K³
each denote a —CH₂ group X denotes an NR¹ group, wherein
R¹ denotes a hydrogen atom or
a $C_{1-5}$-alkyl, $C_{2-4}$-alkenyl-CH₂, $C_{2-4}$-alkynyl-CH₂ or $C_{3-6}$-cycloalkyl group,
wherein the methylene and methyl groups present in the previously mentioned $C_{2-5}$-alkyl groups may be substituted by one to three fluorine atoms, as long as the methylene or methyl groups are not directly bound to the nitrogen atom, and wherein
A¹ denotes either N or CR¹⁰,
A² denotes either N or CR¹¹,
A³ denotes either N or CR¹²,
wherein R¹⁰, R¹¹ and R¹² each independently of one another represent
a hydrogen, fluorine or chlorine atom, or a $C_{1-3}$-alkyl, CF₃, hydroxy or CH₃O— group,
or D denotes one of the groups (II-3) or (II-4)

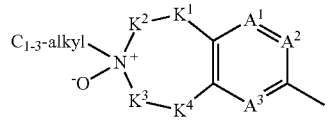

(II-3)

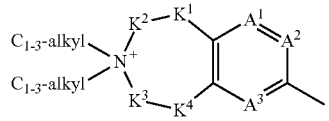

(II-4)

Anion wherein the groups A1, A2, A3, K1, K2, K3, K4 are as hereinbefore defined, and the anion in (II-4) may be selected from among fluoride, chloride, bromide, iodide, sulphate, phosphate, benzoate, salicylate, succinate, citrate or tartrate, and R³ denotes a hydrogen atom,
R⁴ denotes a straight-chain or branched $C_{3-6}$-alkenyl or $C_{3-6}$-alkynyl group,
a straight-chain or branched $C_{1-4}$-alkyl group,
wherein the hydrogen atoms of the straight-chain or branched $C_{1-4}$-alkyl group may optionally be partially replaced by up to four fluorine atoms,
and wherein optionally one to two hydrogen atoms may be replaced independently of one another by a $C_{3-7}$-cycloalkyl, hydroxy, $C_{1-5}$-alkyloxy, phenylmethyloxy, $C_{1-5}$-alkylsulphanyl, $C_{1-5}$-alkylsulphinyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-7}$-cycloalkyleneiminocarbonyl, amino, $C_{1-5}$-alkylamino or di-($C_{1-5}$-alkyl)-amino, $C_{1-5}$-alkylcarbonylamino, carboxy-$C_{1-5}$-alkylcarbonylamino or a $C_{1-5}$-alkyloxycarbonyl-$C_{1-5}$-alkylcarbonylamino group,
wherein the above-mentioned phenyl groups may be replaced by 1 or 2 substituents selected from fluorine, chlorine, bromine, methyl, methoxy, or trifluoromethyl, or wherein the above-mentioned carboxylic acid amide may optionally be additionally substituted at the nitrogen by a $C_{1-5}$-alkyl group, a phenyl, phenyl-$C_{1-2}$-alkyl, heteroaryl-$C_{1-2}$-alkyl or C-linked heteroaryl group, wherein the heteroaryl group is selected from among imidazolyl, furanyl, thiophenyl, thiazolyl, pyrazolyl, tetrazolyl, benzimidazolyl, indolyl, pyrimidinyl, pyrazinyl, oxazolyl, and pyridinyl, and which may optionally be mono- to disubstituted in the phenyl or heteroaryl moiety by identical or different substituents selected from among chlorine or fluorine atoms or $C_{1-3}$-alkyl, CF₃, HO, CH₃O or CHF₂O— groups, R⁵ denotes a hydrogen atom, a straight-chain or branched $C_{1-4}$-alkyl group, a propargyl or $C_{1-3}$-alkyloxy-$C_{1-3}$-alkyl group, or R⁴ and R⁵ together with the carbon atom to which they are bound form
a $C_{5-6}$-cycloalkenyl or $C_{3-7}$-cycloalkyl group,
wherein one of the methylene groups of a $C_{4-7}$-cycloalkyl group may be replaced by an oxygen or sulphur atom or a sulphonyl group, or
1 to 2 carbon atoms of a $C_{3-7}$-cycloalkyl group may optionally be substituted independently of one another by in each case one or two fluorine atoms, or one or two $C_{1-5}$-alkyl groups, or a hydroxy, $C_{1-5}$-alkyloxy, formyloxy, nitrile, carboxy, $C_{1-5}$-alkyloxycarbonyl, aminocarbonyl, $C_{1-5}$-alkylaminocarbonyl, di-($C_{1-5}$-alkyl)-aminocarbonyl or $C_{4-7}$-cycloalkyleneiminocarbonyl group,
with the proviso that a $C_{3-7}$-cycloalkyl group of this kind formed from R⁴ and R⁵ together,
wherein one of the methylene groups of the cyclic group which is linked directly to the carbon atom to which the groups R⁴ and R⁵ are bound, is replaced by an oxygen or sulphur atom,
is excluded, and M denotes a thiophene ring according to formula (III),

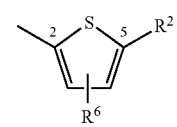

(III)

which is bound to the carbonyl group in formula (I) via the 2-position and is substituted by R² in the 5-position, where
R² denotes a chlorine or bromine atom or an ethynyl group, and
R⁶ denotes a hydrogen atom,
wherein the alkyl, alkenyl, alkynyl and alkyloxy groups contained in the previously mentioned definitions which have more than two carbon atoms may, unless otherwise stated, be straight-chain or branched and the alkyl groups in the previously mentioned dialkylated groups, for example the dialkylamino groups, may be identical or different,
the tautomers, enantiomers, diastereomers, mixtures and salts thereof.

A 6th embodiment of the present invention includes those compounds of general formula (I), corresponding to embodiments 1, 2, 3, 4 or 5, wherein the group
D denotes a substituted bicyclic ring system of formula (II),

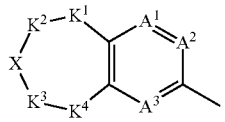

(II)

wherein
$K^1$ and $K^4$
each independently of one another represent a —$CH_2$, —$CHR^{7a}$ or a —$CR^{7b}R^{7c}$— group, where
$R^{7a}/R^{7b}/R^{7c}$
each independently of one another denote a $C_{1-2}$-alkyl group,
$K^2$ and $K^3$
each denote a —$CH_2$ group,
X denotes an $NR^1$ group, wherein
$R^1$ denotes a hydrogen atom or
a $C_{1-5}$-alkyl or $C_{3-6}$-cycloalkyl group,
wherein in the methylene and methyl groups present in the above-mentioned groups one to three hydrogen atoms may be replaced by fluorine atoms, provided that the methylene or methyl groups are not directly bound to the nitrogen atom,
and wherein
$A^1$ denotes $CR^{10}$,
$A^2$ denotes $CR^{11}$,
$A^3$ denotes $CR^{12}$,
where $R^{10}$, $R^{11}$ and $R^{12}$ each independently of one another represent
a hydrogen, fluorine or chlorine atom, or a $C_{1-3}$-alkyl, $CF_3$, HO, $CH_3O$— group,
or
D denotes the group (II-4)

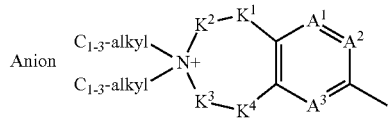

(II-4)

wherein the groups A1, A2, A3, K1, K2, K3, K4 are as hereinbefore defined, and the anion in (II-4) may be selected from among fluoride, chloride, bromide, iodide, sulphate, phosphate, benzoate, salicylate, succinate, citrate or tartrate,
the tautomers, enantiomers, diastereomers, mixtures and salts thereof.

A 7th embodiment of the present invention includes those compounds of general formula (I), corresponding to embodiments 1, 2, 3, 4, 5 or 6, wherein neither
$R^4$ nor $R^5$ may represent a hydrogen atom,
the tautomers, enantiomers, diastereomers, mixtures and salts thereof.

An 8th embodiment of the present invention includes those compounds of general formula (I), corresponding to embodiments 1, 2, 3, 4, 5 or 6, wherein $R^4$ and $R^5$ together with the carbon atom to which they are bound,
form a $C_{5-6}$-cycloalkenyl or $C_{3-7}$-cycloalkyl group,
wherein one of the methylene groups of a $C_{4-7}$-cycloalkyl group may be replaced by an oxygen or sulphur atom,
with the proviso that a $C_{3-7}$-cycloalkyl group of this kind formed from $R^4$ and $R^5$ together,
wherein one of the methylene groups of the cyclic group, which is linked directly to the carbon atom, to which the groups $R^4$ and $R^5$ are bound, is replaced by an oxygen or sulphur atom,
is excluded,
the tautomers, enantiomers, diastereomers, mixtures and salts thereof.

The following ring systems are mentioned as particularly preferred examples of the cyclic groups which may be formed from $R^4/R^5$ and the carbon atom to which they are bound:

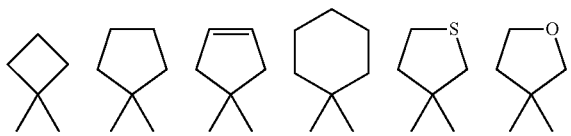

The following preferred compounds of general formula (I) are mentioned by way of example, both as the tautomers, enantiomers, diastereomers, mixtures and salts thereof:

3-[(5-bromo-thiophen-2-yl)-carbonylamino]-N-(3-methyl-2,3,4,5-tetrahydro-1H-benzo[d]azepin-7-yl)-tetrahydro-furan-3-carboxylic acid amide, 3-[(5-chloro-thiophen-2-yl)-carbonylamino]-N-(3-methyl-2,3,4,5-tetrahydro-1H-benzo[d]azepin-7-yl)-tetrahydro-furan-3-carboxylic acid amide, 5-chloro-thiophene-2-carboxylic acid-N-[1-(3-ethyl-2,3,4,5-tetrahydro-1H-benzo[d]azepin-7-ylcarbamoyl)-1-methyl-ethyl]-amide, 5-ethynyl-N-[1-methyl-1-(3-methyl-2,3,4,5-tetrahydro-1H-benzo[d]azepin-7-ylcarbamoyl)-ethyl]-thiophene-2-carboxylic acid amide, 5-chloro-thiophene-2-carboxylic acid-N-[1-methyl-1-(3-methyl-2,3,4,5-tetrahydro-1H-benzo[d]azepin-7-ylcarbamoyl]-ethyl}-amide, 5-bromo-thiophene-2-carboxylic acid-N-[1-methyl-1-(3-methyl-2,3,4,5-tetrahydro-1H-benzo[d]azepin-7-ylcarbamoyl]-ethyl}-amide, 5-chloro-thiophene-2-carboxylic acid-N-[2-methoxy-1-(3-methyl-2,3,4,5-tetrahydro-1H-benzo[d]azepin-7-ylcarbamoyl)-ethyl]-amide, 1-[(5-bromo-thiophen-2-yl)-carbonylamino]-N-(3-methyl-2,3,4,5-tetrahydro-1H-benzo[d]azepin-7-yl)-cyclopentane-1-carboxylic acid amide, 1-[(5-chloro-thiophen-2-yl)-carbonylamino]-N-(3-methyl-2,3,4,5-tetrahydro-1H-benzo[d]azepin-7-yl)-cyclopentane-1-carboxylic acid amide, 3-[(5-chloro-thiophen-2-yl)-carbonylamino]-N-(3-methyl-2,3,4,5-tetrahydro-1H-benzo[d]azepin-7-yl)-tetrahydro-thiophene-3-carboxylic acid amide, 1-[(5-chloro-thiophen-2-yl)carbonylamino]-N-(3-methyl-2,3,4,5-tetrahydro-1H-benzo[d]azepin-7-yl)-cyclobutane-1-carboxylic acid amide, 1-[(5-bromo-thiophen-2-yl)carbonylamino]-N-(3-methyl-2,3,4,5-tetrahydro-1H-benzo[d]azepin-7-yl)-cyclopent-3-ene-1-carboxylic acid amide, 1-[(5-chloro-thiophen-2-yl)carbonylamino]-N-(3-methyl-2,3,4,5-tetrahydro-1H-benzo[d]azepin-7-yl)-cyclohexane-1-carboxylic acid amide, (R)-5-chloro-thiophene-2-carboxylic acid-N-[2-benzyloxy-1-(3-methyl-2,3,4,5-tetrahydro-1H-benzo[d]azepin-7-ylcarbamoyl)-ethyl]-amide, 5-chloro-thiophene-2-carboxylic acid-N-[2-benzyloxy-1-methyl-1-(3-methyl-2,3,4,5-tetrahydro-1H-benzo[d]azepin-7-ylcarbamoyl)-ethyl]-amide, (R)-5-chloro-thiophene-2-carboxylic acid-N-[2-hydroxy-1-methyl-1-(3-methyl-2,3,4,5-tetrahydro-1H-benzo[d]azepin-7-ylcarbamoyl)-ethyl]-amide, 5-bromo-thiophene-2-carboxylic acid-N-[3-hydroxy-1-methyl-1-(3-methyl-2,3,4,5-tetrahydro-1H-benzo[d]azepin-7-ylcarbamoyl)-propyl]-amide, 5-chloro-thiophene-2-carboxylic acid-N-[1-methyl-3-dimethylaminocarbonyl-1-(3-methyl-2,3,4,5-tetrahydro-1H-benzo[d]azepin-7-ylcarbamoyl)-propyl]-amide, 5-chloro-thiophene-2-carboxylic acid-N-[2-(4-hydroxyphenyl)-1-methyl-1-(3-methyl-2,3,4,5-tetrahydro-1H-benzo[d]azepin-7-ylcarbamoyl)-ethyl]-amide, 5-chloro-thiophene-2-carboxylic acid-N-[1-methyl-1-(3,5-dimethyl-2,3,4,5-tetrahydro-1H-benzo[d]azepin-7-ylcarbamoyl)-ethyl]-amide, 5-chloro-thiophene-2-carboxylic acid-N-{1-methyl-1-[3-methyl-5-(4-aminophenyl)-2,3,4,5-tetrahydro-1H-benzo[d]azepin-7-ylcarbamoyl]-ethyl}-amide, 5-chloro-thiophene-2-carboxylic acid-N-[2-ethoxy-1-(3-methyl-2,3,4,5-tetrahydro-1H-benzo[d]azepin-7-ylcarbamoyl)-ethyl]-amide, 5-chloro-thiophene-2-carboxylic acid-N-[3-methoxy-1-(3-methyl-2,3,4,5-tetrahydro-1H-benzo[d]azepin-7-ylcarbamoyl)-propyl]-amide, 5-chloro-thiophene-2-carboxylic acid-N-[2-isopropyloxy-1-(3-methyl-2,3,4,5-tetrahydro-1H-benzo[d]azepin-7-ylcarbamoyl)-ethyl]-amide, (R)-5-chloro-thiophene-2-carboxylic acid-N-[3-benzyloxy-1-(3-methyl-2,3,4,5-tetrahydro-1H-benzo[d]azepin-7-ylcarbamoyl)-propyl]-amide, 1-[(5-chloro-thiophen-2-yl)-carbonylamino]-3,4-dimethoxy-N-(3-methyl-2,3,4,5-tetrahydro-1H-benzo[d]azepin-7-yl)-cyclopentane-1-carboxylic acid amide, 5-chloro-thiophene-2-carboxylic acid-N—C-(1-methylpyrazol-3-yl)-C-(3-methyl-2,3,4,5-tetrahydro-1H-benzo[d]azepin-7-ylcarbamoyl)-methyl]-amide, (R)-5-chloro-thiophene-2-carboxylic acid-N-[2-phenyl-1-(3-methyl-2,3,4,5-tetrahydro-1H-benzo[d]azepin-7-ylcarbamoyl)-ethyl]-amide, (R)-5-chloro-thiophene-2-carboxylic acid-N-[2-(furan-2-yl)-1-(3-methyl-2,3,4,5-tetrahydro-1H-benzo[d]azepin-7-ylcarbamoyl)-ethyl]-amide, 5-chloro-thiophene-2-carboxylic acid-N-[2-(4-methoxyphenyl)-1-(3-methyl-2,3,4,5-tetrahydro-1H-benzo[d]azepin-7-ylcarbamoyl)-ethyl]-amide, 5-chloro-thiophene-2-carboxylic acid-N-[2-(4-hydroxy-3-nitro-phenyl)-1-(3-methyl-2,3,4,5-tetrahydro-1H-benzo[d]azepin-7-ylcarbamoyl)-ethyl]-amide, (R)-5-chloro-thiophene-2-carboxylic acid-N-[2-(4-hydroxyphenyl)-1-(3-methyl-2,3,4,5-tetrahydro-1H-benzo[d]azepin-7-ylcarbamoyl)-ethyl]-amide, (R)-5-chloro-thiophene-2-carboxylic acid-N-[2-cyclohexyl-1-(3-methyl-2,3,4,5-tetrahydro-1H-benzo[d]azepin-7-ylcarbamoyl)-ethyl]-amide, (R)-5-chloro-thiophene-2-carboxylic acid-N-[3-aminocarbonyl-1-(3-methyl-2,3,4,5-tetrahydro-1H-benzo[d]azepin-7-ylcarbamoyl)-propyl]-amide, (R)-5-chloro-thiophene-2-carboxylic acid-N-[2-acetylamino-1-(3-methyl-2,3,4,5-tetrahydro-1H-benzo[d]azepin-7-ylcarbamoyl)-ethyl]-amide, (R)-5-bromo-thiophene-2-carboxylic acid-N-[2-benzoylamino-1-(3-methyl-2,3,4,5-tetrahydro-1H-benzo[d]azepin-7-ylcarbamoyl)-ethyl]-amide, (R)-5-chloro-thiophene-2-carboxylic acid-N-[2-(2-hydroxycarbonyl-ethyl)carbonylamino-1-(3-methyl-2,3,4,5-tetrahydro-1H-benzo[d]azepin-7-ylcarbamoyl)-ethyl]-amide, (R)-5-chloro-thiophene-2-carboxylic acid-N-[2-(2-hydroxycarbonyl-ethyl)carbonylamino-1-(3-methyl-2,3,4,5-tetrahydro-1H-benzo[d]azepin-7-ylcarbamoyl)-ethyl]-amide, (R)-5-chloro-thiophene-2-carboxylic acid-N-[2-(4-methoxycarbonyl-butyl)carbonylamino-1-(3-methyl-2,3,4,5-tetrahydro-1H-benzo[d]azepin-7-ylcarbamoyl)-ethyl]-amide, 5-chloro-thiophene-2-carboxylic acid-N-[1-methyl-1-(3,3-dimethyl-2,3,4,5-tetrahydro-1H-benzo[d]azepinium-7-ylcarbamoyl)-ethyl}-amide iodide, 3-[(5-chloro-thiophen-2-yl)-carbonylamino]-N-(3,5-dimethyl-2,3,4,5-tetrahydro-1H-benzo[d]azepin-7-yl)-tetrahydrofuran-3-carboxylic acid amide.

The invention also relates to physiologically acceptable salts of the compounds according to the embodiments defined above and the Examples.

The invention also relates to pharmaceutical compositions containing a compound or a physiologically acceptable salt of a compound according to the embodiments defined above and the Examples, optionally together with one or more inert carriers and/or diluents.

The invention also relates to the use of a compound or a physiologically acceptable salt of a compound according to the embodiments defined above and the Examples, for preparing a pharmaceutical composition with an inhibitory effect on factor Xa and/or an inhibitory effect on related serine proteases.

The invention also relates to a process for preparing a pharmaceutical composition, characterised in that by a non-chemical method a compound or a physiologically acceptable salt of a compound according to the embodiments defined above and the Examples is incorporated in one or more inert carriers and/or diluents.

According to the invention the compounds of general formula (I) are obtained by methods known per se, for example by the following methods:

(a) The preparation of a compound of general formula (Ia)

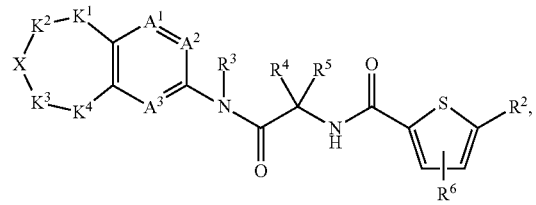

(Ia)

wherein $A^1$ to $A^3$, $K^1$ to $K^4$, X and $R^1$ to $R^6$ are defined as in embodiment 1, and which may optionally be protected at any amino, hydroxy, carboxy or thiol groups present by the usual protective groups such as for example those described in T. W. Greene, P. G. M. Wuts in "Protective Groups in Organic Synthesis" and the protective groups of which may be cleaved in a manner known from the literature, is described in the exemplifying embodiments or may be carried out for example according to one of the following formula schemes 1 and 2:

Scheme 1

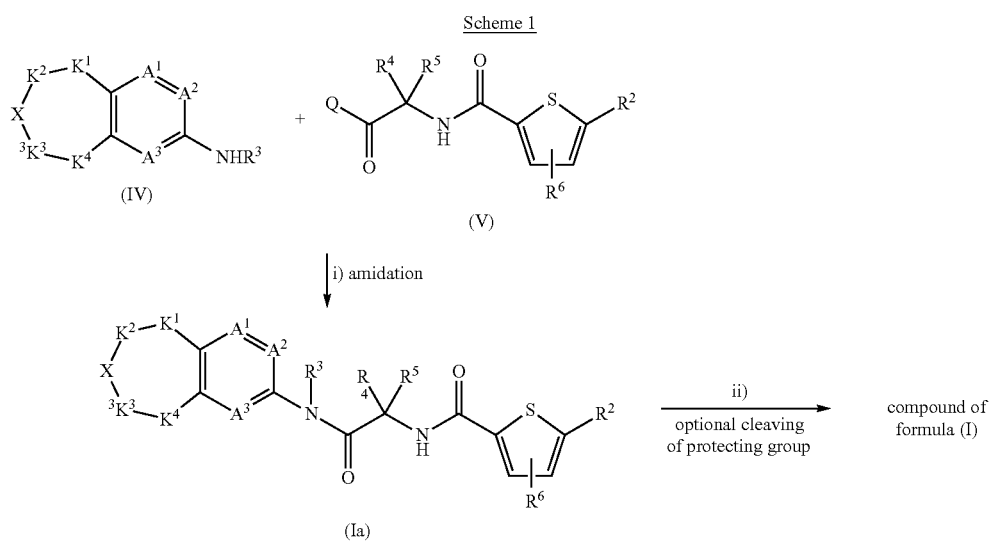

Scheme 2

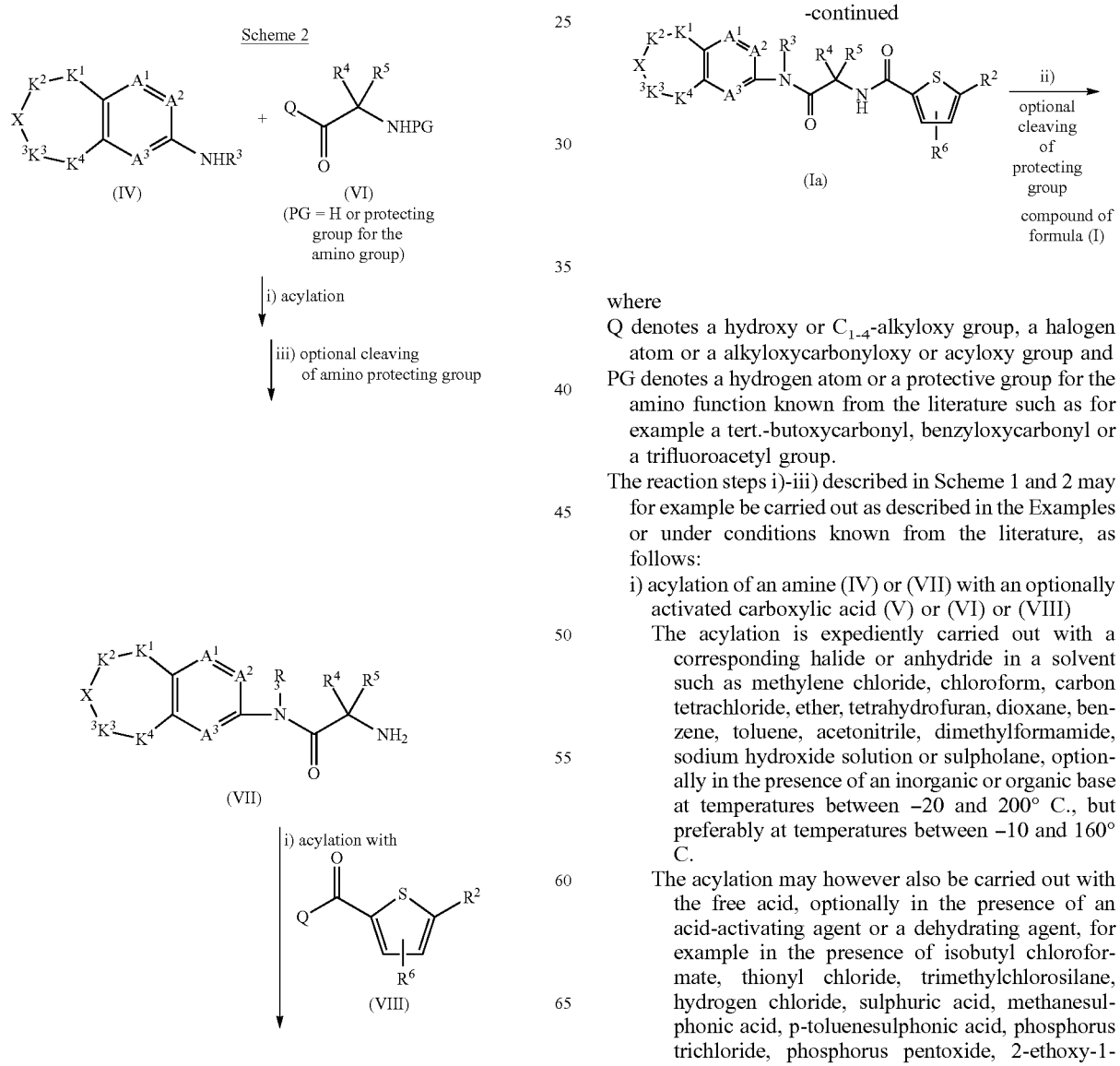

where
Q denotes a hydroxy or $C_{1-4}$-alkyloxy group, a halogen atom or a alkyloxycarbonyloxy or acyloxy group and
PG denotes a hydrogen atom or a protective group for the amino function known from the literature such as for example a tert.-butoxycarbonyl, benzyloxycarbonyl or a trifluoroacetyl group.

The reaction steps i)-iii) described in Scheme 1 and 2 may for example be carried out as described in the Examples or under conditions known from the literature, as follows:

i) acylation of an amine (IV) or (VII) with an optionally activated carboxylic acid (V) or (VI) or (VIII)

The acylation is expediently carried out with a corresponding halide or anhydride in a solvent such as methylene chloride, chloroform, carbon tetrachloride, ether, tetrahydrofuran, dioxane, benzene, toluene, acetonitrile, dimethylformamide, sodium hydroxide solution or sulpholane, optionally in the presence of an inorganic or organic base at temperatures between −20 and 200° C., but preferably at temperatures between −10 and 160° C.

The acylation may however also be carried out with the free acid, optionally in the presence of an acid-activating agent or a dehydrating agent, for example in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, 2-ethoxy-1- ethoxycarbonyl-1,2-dihydroquinoline (EEDQ), N,N'-dicyclohexylcarbodiimide, N,N'-dicyclohexylcarbodiimide/camphorsulphonic acid, N,N'-dicyclohexylcarbodiimide/N-hydroxysuccinimide or 1-hydroxy-benzotriazole, N,N'-carbonyldiimidazole, O-(benzotriazol-1-yl)-N,N, N,N'-tetramethyluronium tetrafluoroborate/N-methylmorpholine, O-(benzotriazol-1-yl)-N,N,N',N'-tetramethyluronium tetrafluoroborate/N-ethyldiisopropylamine, O-pentafluorophenyl-N,N,N',N'-tetramethyluronium-hexafluorophosphate/triethylamine, N,N'-thionyldiimidazole or triphenylphosphine/carbon tetrachloride, at temperatures between −20 and 200° C., but preferably at temperatures between −10 and 160° C.

The acylation may also be carried out with a carboxylic acid ester (V) or (VI) and the amine (IV) by activation with trimethylaluminium.

The acylation of a compound of general formula (IV) may however also be carried out with a reactive carboxylic acid derivative of general formula (IX)

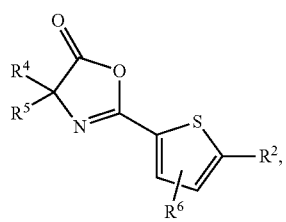

(IX)

wherein $R^4$ to $R^6$ and $R^2$ are defined as in embodiment 1. The acylation is then conveniently carried out in a solvent such as for example toluene, tetrahydrofuran or dimethylformamide, with the addition of an acid such as acetic acid or camphorsulphonic acid or optionally in the presence of a Lewis acid such as zinc chloride or copper(II) chloride and optionally by the addition of amine bases such as for example diisopropylethylamine, triethylamine or N-methylmorpholine, at temperatures between −10 and 100° C., for example using a microwave oven or as described in P. Wipf et al., Helvetica Chimica Acta, 69, 1986, 1153.

Compounds of general formula (IX) may be prepared from compounds of general formula (V), expediently in a solvent or mixture of solvents such as dichloromethane, trichloromethane, carbon tetrachloride, benzene, chlorobenzene, toluene, xylene, hexamethyldisiloxane, ether, tetrahydrofuran, dioxane, acetonitrile, pyridine, optionally in the presence of N,N'-dicyclohexylcarbodiimide, N,N'-dicyclohexylcarbodiimide/N-hydroxysuccinimide or 1-hydroxy-benzotriazole, N,N'-carbonyldiimidazole, O-(benzotriazol-1-yl)-N,N,N',N'-tetramethyluronium tetrafluoroborate/N-methylmorpholine, O-(benzotriazol-1-yl)-N,N,N',N'-tetramethyluronium tetrafluoroborate/N-ethyldiisopropylamine, or in acetic anhydride at temperatures between −20 and 200° C., but preferably at temperatures between −10 and 100° C. Other methods of amide coupling are described for example in P. D. Bailey, I. D. Collier, K. M. Morgan in "Comprehensive Functional Group Interconversions", Vol. 5, page 257ff., Pergamon 1995 or in Supplementary Volume 22 to Houben-Weyl, Thieme Verlag, 2003 and literature cited therein.

ii) or iii) Cleaving a protective group

The optional subsequent cleaving of any protective group used is carried out hydrolytically, for example, in an aqueous solvent, e.g. In water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether cleavage, e.g. In the presence of iodotrimethylsilane, at temperatures between 0 and 100° C., preferably at temperatures between 10 and 50° C.

A benzyl, methoxybenzyl or benzyloxycarbonyl group may, however, be cleaved hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at room temperature, and under a hydrogen pressure of 1 to 7 bar, but preferably 1 to 5 bar.

A protective group may however also be cleaved by the methods described in T. W. Greene, P. G. M. Wuts in "Protective Groups in Organic Synthesis".

(b) The components of general formula

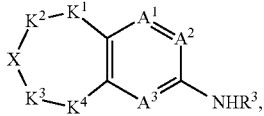

(IV)

wherein $A^1$, $A^2$, $A^3$, $K^1$, $K^2$, $K^3$, $K^4$, X and $R^3$ are defined as in embodiment 1, and and which may optionally be protected at any amino, hydroxy, carboxy or thiol groups present by the usual protective groups such as for example those described in T. W. Greene, P. G. M. Wuts in "Protective Groups in Organic Synthesis" and the protective groups of which may be cleaved in a manner known from the literature in the course of the synthesis sequence to form compounds of formula (I), are known from the literature, or their synthesis is described in the exemplifying embodiments, or they may be prepared for example using methods of synthesis known from the literature or analogously to methods of synthesis known from the literature as described for example in DE4429079, U.S. Pat. No. 4,490,369, DE3515864, U.S. Pat. No. 5,175,157, DE1921861, WO85/00808 or in G. Bobowski et al., J. Heterocyclic Chem. 16, 1525, 1979 or in P. D. Johnson et al., Bioorg. Med. Chem. Lett 2003, 4197. Fragments bridged in the azepine moiety as shown in formula II-1 or II-2 may for example be prepared analogously to J. W. Coe et al. J. Med. Chem., 2005, 48, 3474 or J. W. Coe et al., US Patent application US2005/0020616.

The benzazepine modifications in formula II-3 or II-4 may for example be prepared by oxidation using meta-chloroperbenzoic acid or alkylation with an alkyl halide from suitable benzepine precursors as described in the experimental section.

For example, a compound of general formula (IV), wherein $R^3$ denotes a hydrogen atom and A1, A2, A3, K1, K2, K3, K4 and X are defined as in embodiment 1, may be prepared by reduction of the nitro group of a compound of general formula (III)

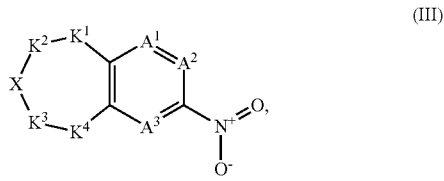

(III)

wherein A1, A2, A3, K1, K2, K3, K4 and X are defined as in embodiment 1, as follows.

The reduction of the nitro group is for example conveniently carried out in a solvent or mixture of solvents such as water, aqueous ammonium chloride solution, hydrochloric acid, sulphuric acid, phosphoric acid, formic acid, acetic acid, acetic anhydride with base metals such as iron, zinc, tin or sulphur compounds such as ammonium sulphide, sodium sulphide or sodium dithionite or by catalytic hydrogenation with hydrogen, for example under a pressure between 0.5 and 100 bar, but preferably between 1 and 50 bar, or with hydrazine as reducing agent, conveniently in the presence of a catalyst such as for example Raney nickel, palladium charcoal, platinum oxide, platinum on mineral fibres or rhodium, or with complex hydrides such as lithium aluminium hydride, sodium borohydride, sodium cyanoborohydride, diisobutylaluminium hydride, conveniently in a solvent or mixture of solvents such as water, methanol, ethanol, isopropanol, pentane, hexane, cyclohexane, heptane, benzene, toluene, xylene, ethyl acetate, methylpropionate, glycol, glycoldimethylether, diethyleneglycoldimethylether, dioxane, tetrahydrofuran, N-methylpyrrolidinone, or N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C.

(c) The components of general formula

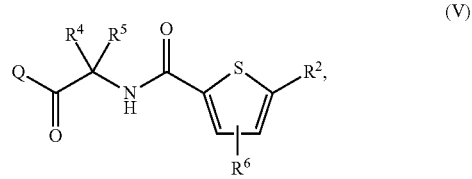

(V)

wherein $R^4$, $R^5$, $R^6$ and $R^2$ are defined as in embodiment 1, and where Q denotes a hydroxy or $C_{1-4}$-alkyloxy group, a halogen atom or a alkyloxycarbonyloxy or acyloxy group which may optionally be protected at any amino, hydroxy, carboxy or thiol groups present by the usual protective groups such as for example those described in T. W. Greene, P. G. M. Wuts in "Protective Groups in Organic Synthesis" and the protective groups of which may be cleaved in a manner known from the literature in the course of the synthesis sequence to form compounds of formula (I), are known from the literature, or their synthesis is described in the exemplifying embodiments, or they may be prepared for example using methods of synthesis known from the literature or analogously to methods of synthesis known from the literature as described for example in WO04/46138.

Scheme 3

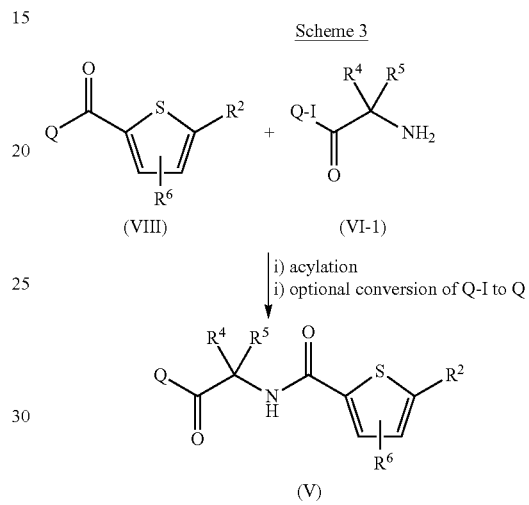

For example they may also be prepared according to Scheme 3 by reacting a compound (VIII) with an amine (VI-1), where Q denotes a hydroxy or $C_{1-4}$-alkyloxy group, a halogen atom or an alkyloxycarbonyloxy or acyloxy group and Q-I denotes a hydroxy or $C_{1-4}$-alkyloxy group, which may optionally be converted into Q after the acylation step by saponification and activation as described above. The acylation may be carried out according to the acylation conditions described above.

The amino acid derivatives (VI-1) are known from the literature or may be prepared analogously to methods known from the literature as described in the Examples, for example, from commercially obtainable amino acid derivatives.

In the reactions described hereinbefore any reactive groups present such as hydroxy, carboxy, amino, alkylamino or imino groups may be protected during the reaction by conventional protective groups which are cleaved again after the reaction.

For example a protecting group for a hydroxy group might be the methoxy, benzyloxy, trimethylsilyl, acetyl, benzoyl, tert.-butyl, trityl, benzyl or tetrahydropyranyl group.

Protecting groups for a carboxyl group might be the trimethylsilyl, methyl, ethyl, tert.-butyl, benzyl or tetrahydropyranyl group.

A protecting group for an amino, alkylamino or imino group might be the acetyl, trifluoroacetyl, benzoyl, ethoxycarbonyl, tert.-butoxycarbonyl, benzyloxycarbonyl, benzyl, methoxybenzyl or 2,4-dimethoxybenzyl group and additionally, for the amino group, the phthalyl group.

For example a protecting group for an ethynyl group might be the trimethylsilyl, diphenylmethylsilyl, tert.butyldimethylsilyl or a 1-hydroxy-1-methyl-ethyl group.

Other protective groups which may be used and their removal are described in T. W. Greene, P. G. M. Wuts, "Protective Groups in Organic Synthesis", Wiley, 1991 and 1999.

Any protective group used is optionally subsequently cleaved for example by hydrolysis in an aqueous solvent, e.g. In water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by means of ether splitting, e.g. In the presence of iodotrimethylsilane, at temperatures between 0 and 100° C., preferably at temperatures between 10 and 50° C.

A benzyl, methoxybenzyl or benzyloxycarbonyl group, however, is cleaved by hydrogenolysis, for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at room temperature, and under a hydrogen pressure of 1 to 7 bar, but preferably 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures between 0 and 50° C., but preferably at room temperature.

A methoxy group is conveniently cleaved in the presence of boron tribromide in a solvent such as methylene chloride at temperatures between −35 and −25° C.

A 2,4-dimethoxybenzyl group, however, is preferably cleaved in trifluoroacetic acid in the presence of anisol.

A tert.-butyl or tert.-butyloxycarbonyl group is preferably cleaved by treatment with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treatment with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at room temperature and under inert gas, or by treatment with a catalytic amount of tris-(triphenylphosphine)-rhodium(I)chloride in a solvent such as aqueous ethanol and optionally in the presence of a base such as 1,4-diazabicyclo[2,2,2]octane at temperatures between 20 and 70° C. Moreover, the compounds of general formula I obtained may be resolved into their enantiomers and/or diastereomers.

Thus, for example, the compounds of general formula I obtained which occur as racemates may be separated by methods known per se (cf. Allinger N. L. And Eliel E. L. In "Topics in Stereochemistry", Vol. 6, Wiley Interscience, 1971) into their optical enantiomers and compounds of general formula I with at least 2 asymmetric carbon atoms may be resolved into their diastereomers on the basis of their physical-chemical differences using methods known per se, e.g. By chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. Esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. The D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

Furthermore, the compounds of formula (I) obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula (I) contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned hereinbefore, the compounds of general formula (I) and the tautomers, enantiomers, diastereomers and physiologically acceptable salts thereof have valuable pharmacological properties, particularly an antithrombotic activity which is preferably based on an effect on thrombin or factor Xa, for example on a thrombin-inhibiting or factor Xa-inhibiting activity, on a prolonging effect on the aPTT time and on an inhibitory effect on related serine proteases such as e.g. urokinase, factor VIIa, factor IX, factor XI and factor XII.

The compounds listed in the Experimental Section were investigated for their effect on the inhibition of factor Xa as follows:

Method:

Enzyme-kinetic measurement with chromogenic substrate. The quantity of p-nitroaniline (pNA) released from the colourless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material:

Tris(hydroxymethyl)-aminomethane buffer (100 mMol) and sodium chloride (150 mMol), pH 8.0 plus 1 mg/ml Human Albumin Fraction V, protease-free Factor Xa (Calbiochem), spec. Activity: 217 IU/mg, final concentration: 7 IU/ml for each reaction mixture Substrate S 2765 (Chromogenix), final concentration: 0.3 mM/l (1 KM) for each reaction mixture Test substance: final concentration 100, 30, 10, 3, 1, 0.3, 0.1, 0.03, 0.01, 0.003, 0.001 μMol/l Procedure:

10 μl of a 23.5-times concentrated starting solution of the test substance or solvent (control), 175 μl of TRIS/HSA buffer and 25 μl of a 65.8 U/L Factor Xa working solution are incubated for 10 minutes at 37° C. After the addition of 25 μl of S 2765 working solution (2.82 mMol/l) the sample is measured in a photometer (SpectraMax 250) at 405 nm for 600 seconds at 37° C.

Evaluation:
1. Determining the maximum increase (deltaOD/minutes) over 21 measuring points.
2. Determining the % inhibition based on the solvent control.
3. Plotting a dosage/activity curve (% inhibition vs substance concentration).
4. Determining the $IC_{50}$ by interpolating the X-value (substance concentration) of the dosage/activity curve at Y=50% inhibition.

All the compounds tested had an $IC_{50}$ value of less than 100 μmol/L.

The compounds prepared according to the invention are generally well tolerated.

In view of their pharmacological properties the new compounds and the physiologically acceptable salts thereof are suitable for the prevention and treatment of venous and arterial thrombotic diseases, such as for example the prevention and treatment of deep leg vein thrombosis, for preventing reocclusions after bypass operations or angioplasty (PT(C)A), and occlusion in peripheral arterial diseases, and for preventing and treating pulmonary embolism, disseminated intravascular coagulation and severe sepsis, for preventing and treating DVT in patients with exacerbated COPD, for treating ulcerative colitis, for preventing and treating coronary thrombosis, for preventing stroke and the occlusion of shunts.

In addition, the compounds according to the invention are suitable for antithrombotic support in thrombolytic treatment, such as for example with alteplase, reteplase, tenecteplase, staphylokinase or streptokinase, for preventing long-term restenosis after PT(C)A, for the prevention and treatment of ischaemic events in patients with all forms of coronary heart disease, for preventing metastasis and the growth of tumours and inflammatory processes, e.g. In the treatment of pulmonary fibrosis, for preventing and treating rheumatoid arthritis, for preventing and treating fibrin-dependent tissue adhesions and/or the formation of scar tissue and for promoting wound healing processes.

In view of their pharmacological properties the new compounds and the physiologically acceptable salts thereof are also suitable for the treatment of Alzheimer's and Parkinson's disease. One explanation for this arises for example from the following findings, from which it can be concluded that thrombin inhibitors or factor Xa inhibitors, by inhibiting thrombin formation or thrombin activity, may be valuable drugs for treating Alzheimer's and Parkinson's disease. Clinical and experimental studies indicate that neurotoxic mechanisms, for example the inflammation which is associated with the activation of proteases of the clotting cascade, are involved in the dying of neurones following brain injury. Various studies point to the involvement of thrombin in neurodegenerative processes, for example following a stroke, repeated bypass operations or traumatic brain injury. An increased thrombin activity has been demonstrated some days after peripheral nerve damage, for example. It has also been shown that thrombin causes a neurite retraction, as well as glia proliferation, and apoptosis in primary cultures of neurones and neuroblastoma cells (for a summary see: *Neurobiol. Aging* 2004, 25(6), 783-793). Moreover, various in vitro studies on the brains of patients with Alzheimer's disease indicated that thrombin plays a role in the pathogenesis of this disease (*Neurosci. Lett.* 1992, 146, 152-54). A concentration of immune-reactive thrombin has been detected in neurite plaques in the brains of Alzheimer's patients. It has been demonstrated in vitro that thrombin also plays a part in the regulation and stimulation of the production of the "Amyloid Precursor Protein" (APP) as well as in the cleaving of the APP into fragments which can be detected in the brains of Alzheimer's patients. Moreover, it has been demonstrated that the thrombin-induced microglial activation leads in vivo to the degeneration of nigral dopaminergic neurones. These findings lead one to conclude that microglial activation, triggered by endogenous substance(s) such as thrombin, for example, are involved in the neuropathological process of the cell death of dopaminergic neurones of the kind which occurs in patients with Parkinson's disease (*J. Neurosci.* 2003, 23, 5877-86).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day.

For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. Clopidogrel, ticlopidine), with $P_2T$ receptor antagonists (e.g. Cangrelor) or with combined thromboxane receptor antagonists/synthetase inhibitors (e.g. Terbogrel).

EXPERIMENTAL SECTION

The Examples that follow are intended to illustrate the invention, without restricting its scope.

As a rule, melting points and/or IR, UV, $^1$H-NMR and/or mass spectra have been obtained for the compounds prepared. Unless otherwise stated, $R_f$ values were determined using ready-made silica gel 60 $F_{254}$ TLC plates (E. Merck, Darmstadt, Item no. 1.05714) without chamber saturation. The $R_f$ values given under the heading Alox were determined using ready-made aluminium oxide 60 $F_{254}$ TLC plates (E. Merck, Darmstadt, Item no. 1.05713) without chamber saturation. The $R_f$ values given under the heading Reversed-phase-8 (RP-8) were determined using ready-made RP-8 $F_{254s}$ TLC plates (E. Merck, Darmstadt, Item no. 1.15684) without chamber saturation. The ratios given for the eluants refer to units by volume of the solvents in question. For chromato-graphic purification silica gel made by Messrs Millipore (MATREX™, 35-70 μm) was used. Unless more detailed information is provided as to the configuration, it is not clear whether the products are pure stereoisomers or mixtures of enantiomers and diastereomers.

The following abbreviations are used in the test descriptions:
BOC tert.-butoxycarbonyl
DIPEA N-ethyl-diisopropylamine
DMF N,N'-dimethylformamide
sat. saturated
h hour(s)
HATU O-(7-azabenzotriazol-1-yl)-N,N,N',N'-tetramethyl-uronium-hexafluorophosphate
NaHMDS sodium hexamethyldisilazide
i. vac. in vacuo
conc. concentrated
min minute(s)
NMM N-methyl-morpholine
$R_f$ retention factor
$R_t$ retention time
TBTU O-(benzotriazol-1-yl)-N,N,N',N'-tetramethyluronium tetrafluoroborate
TEA triethylamine
TFA trifluoroacetic acid
THF tetrahydrofuran.

The term "thiophen-2-yl" or "thien-2-yl" denotes the group shown in the box:

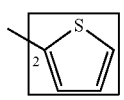

The HPLC-MS data were obtained under the following conditions:
Method 1:
Waters ZQ2000 mass spectrometer, Gilson G215 Autosampler, HP1100 HPLC and diode array detector.
The mobile phase used was:
A: water with 0.10% TFA
B: acetonitrile with 0.10% TFA

| time in min | % A | % B | flow rate in ml/min |
|---|---|---|---|
| 0.00 | 95 | 5 | 1.00 |
| 0.40 | 95 | 5 | 1.00 |
| 4.00 | 2 | 98 | 1.00 |
| 4.35 | 2 | 98 | 1.00 |
| 4.50 | 95 | 5 | 1.00 |

The stationary phase used was an X-Terra MS C18 column, 3.5 μm, 4.6 mm×50 mm.
The diode array detection was carried out at a wavelength range of 210-500 nm.
Method 2:
Waters Alliance 2695, PDA Detector 2996, ZQ 2002
The mobile phase used was:
A: water with 0.10% TFA
B: acetonitrile with 0.10% TFA

| time in min | % A | % B | flow rate in ml/min |
|---|---|---|---|
| 0.00 | 95 | 5 | 1.00 |
| 0.10 | 95 | 5 | 1.00 |
| 3.10 | 2 | 98 | 1.00 |
| 4.50 | 2 | 98 | 1.00 |
| 5.00 | 95 | 5 | 1.00 |

The stationary phase used was a Waters X-Terra MS C18 column, 2.5 μm, 4.6 mm×30 mm
Method 3:
Waters Alliance 2695, PDA Detector 2996
The mobile phase used was:
A: water with 0.13% TFA
B: acetonitrile with 0.10% TFA

| time in min | % A | % B | flow rate in ml/min |
|---|---|---|---|
| 0.00 | 95 | 5 | 1.00 |
| 0.75 | 95 | 5 | 1.00 |
| 5.25 | 2 | 98 | 1.00 |
| 5.75 | 2 | 98 | 1.00 |
| 6.05 | 95 | 5 | 1.00 |
| 6.55 | 95 | 5 | 1.00 |

The stationary phase used was a Varian Microsorb 100 C18 column; 3.5 μm; 4.6 mm×50 mm
Method 3a
Waters Alliance 2695, PDA Detector 2996
The mobile phase used was:
A: water with 0.1% TFA
B: acetonitrile with 0.1% TFA

| time in min | % A | % B | flow rate in ml/min |
|---|---|---|---|
| 0.00 | 95 | 5 | 1.00 |
| 0.1 | 95 | 5 | 1.00 |
| 3.1 | 2 | 98 | 1.00 |
| 4.5 | 2 | 98 | 1.00 |
| 5.0 | 95 | 5 | 1.00 |

The stationary phase used was a Varian Microsorb 100 C18 column; 2.5 μm; 4.6 mm×30 mm
Method 4:
Agilent 1100
The mobile phase used was:
A: water with 0.10% formic acid
B: acetonitrile with 0.10% formic acid

| time in min | % A | % B | flow rate in ml/min |
|---|---|---|---|
| 0.00 | 95 | 5 | 1.60 |
| 4.50 | 10 | 90 | 1.60 |
| 5.00 | 10 | 90 | 1.60 |
| 5.50 | 90 | 10 | 1.60 |

The stationary phase used was a Zorbax StableBond C18 column; 3.5 μm; 4.6 mm×75 mm
Method 5:
Waters Alliance 2695, PDA Detector 2996
The mobile phase used was:
A: water with 0.1% TFA
B: acetonitrile with 0.1% TFA

| time in min | % A | % B | flow rate in ml/min |
|---|---|---|---|
| 0.00 | 95 | 5 | 5.00 |
| 0.20 | 95 | 5 | 5.00 |
| 1.35 | 2 | 98 | 5.00 |
| 1.55 | 2 | 98 | 5.00 |
| 1.65 | 95 | 5 | 5.00 |
| 1.85 | 95 | 5 | 5.00 |

The stationary phase used was an Interchim HS Strategy 5 C18-2 column; 5 μm; 4.6 mm×50 mm
Method 6:
Waters Alliance 26905, PDA Detector 996
The mobile phase used was:
A: water with 0.1% TFA
B: acetonitrile with 0.1% TFA

| time in min | % A | % B | flow rate in ml/min |
|---|---|---|---|
| 0.00 | 95 | 5 | 2.00 |
| 0.10 | 95 | 5 | 2.00 |
| 2.10 | 2 | 98 | 2.00 |
| 3.00 | 2 | 98 | 2.00 |
| 3.25 | 95 | 5 | 2.00 |

The stationary phase used was a MerckChromolith SpeedRod RP-18e column; 4.6 mm×50 mm Example 1

3-[(5-bromo-thiophen-2-yl)-carbonylamino]-N-(3-methyl-2,3,4,5-tetrahydro-1H-benzo[d]azepin-7-yl)-tetrahydrofuran-3-carboxylic acid amide

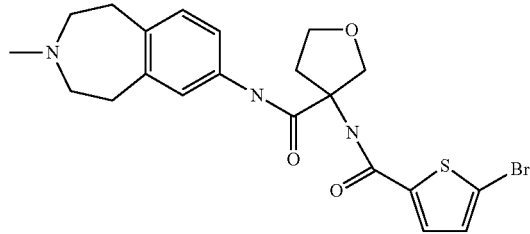 [SMILES: CN1CCc2ccc(NC(=O)C3(NC(=O)c4ccc(Br)s4)CCOC3)cc2CC1]

(a) 7-nitro-2,3,4,5-tetrahydro-1H-benzo[d]azepine 8.4 g (29.0 mmol) 3-trifluoroacetyl-7-nitro-2,3,4,5-tetrahydro-1H-benzo[d]azepine are suspended under a nitrogen atmosphere in 80 ml of methanol and combined with 5 ml NaOH solution (50%) and stirred for 2 h at 70° C.
The methanol is distilled off using the rotary evaporator, the residue is combined with water and extracted with tert.-butylethylether. The organic phase is washed with NaOH solution (50%) and sat. Sodium chloride solution, dried on sodium sulphate and evaporated to dryness i. vac.
Yield: 5.1 g (91%)
$R_f$ value: 0.28 (aluminium oxide; dichloromethane/ethanol=95:5)
$C_{10}H_{12}N_2O_2$ (192.22)
Mass spectrum: $(M+H)^+=193$ (b) 3-methyl-7-nitro-2,3,4,5-tetrahydro-1H-benzo[d]azepine 5.0 g (26.0 mmol) 7-nitro-2,3,4,5-tetrahydro-1H-benzo[d][azepine are mixed in 9.8 ml (260.1 mol) formic acid with 15.5 ml (208.1 mmol) formalin solution in water (37%), with stirring, at room temperature, and stirred overnight at 70° C. The reaction mixture is made alkaline with NaOH solution (50%) while cooling with an ice bath and extracted with tert.-butylmethylether. The organic phase is dried on sodium sulphate and evaporated to dryness i. vac.
Yield: 4.8 g (90%)
$R_f$ value: 0.65 (aluminium oxide; dichloromethane/ethanol=95:5)
$C_{11}H_{14}N_2O_2$ (206.24)
Mass spectrum: $(M+H)^+=207$ (c) 3-methyl-2,3,4,5-tetrahydro-1H-benzo[d]azepin-7-ylamine 4.8 g (23.2 mmol) 3-methyl-7-nitro-2,3,4,5-tetrahydro-1H-benzo[d]azepine are dissolved in 45 ml of methanol and combined with 400 mg Pd/C 10%. The mixture is hydrogenated in a Parr apparatus at room temperature at 3 bar hydrogen pressure for 5 hours. Then the catalyst is filtered off and the filtrate is evaporated down i. vac.
Yield: 3.9 g (96%)
$R_f$ value: 0.36 (aluminium oxide; dichloromethane/ethanol=98:2) $C_{11}H_{16}N_2$ (176.26)
Mass spectrum: $(M+H)^+=177$ (d) 3-amino-tetrahydro-furan-3-carboxylic acid-hydrochloride 3.5 g (15.1 mmol) 3-tert.-butoxycarbonylamino-tetrahydro-furan-3-carboxylic acid are dissolved in 150 ml of 1-molar hydrochloric acid and stirred for 1 h at room temperature. Then the reaction mixture is lyophilised.
Yield: 2.5 g (100%)
$C_5H_9NO_3*HCl$ (167.59)
Mass spectrum: $(M+H)^+=132$ (e) 3-[(5-bromo-thiophen-2-yl)-carbonylamino]-tetrahydro-furan-3-carboxylic acid 3.1 g (14.9 mmol) 5-bromo-thiophene-2-carboxylic acid in 50 ml dichloromethane are combined with 5.4 ml (74.6 mmol) thionyl chloride with stirring at room temperature and stirred for 3.5 h at reflux temperature. Then the reaction mixture is evaporated to dryness.
2.5 g (14.9 mmol) 3-amino-tetrahydro-furan-3-carboxylic acid-hydrochloride are dissolved in 2.0 ml (14.9 mmol) TEA and 150 ml acetonitrile and combined with 5.9 ml (22.4 mmol) N,O-bis-(trimethylsilyl)-trifluoro-acetamide with stirring and refluxed for 4 h with stirring. The reaction mixture is combined with 4.1 ml (29.8 mmol) TEA and the solution of the prepared acid chloride in 50 ml acetonitrile, stirred for 15 min at reflux temperature and then cooled slowly to room temperature. Then the mixture is evaporated to dryness i. vac., the residue is combined with water and 2-molar sodium carbonate solution and washed with diethyl ether. The aqueous phase is adjusted to pH 1 with 20 ml conc. Hydrochloric acid, the precipitate is suction filtered and dried at 50° C. in the vacuum drying cupboard.
Yield: 3.6 g (75%)
$C_{10}H_{10}BrNO_4S$ (320.16)
Mass spectrum: $(M-H)^-=318/320$ (bromine isotopes)

(f) 3-[(5-bromo-thiophen-2-yl)-carbonylamino]-N-(3-methyl-2,3,4,5-tetrahydro-1H-benzo[d]azepin-7-yl)-tetrahydrofuran-3-carboxylic acid amide 700.0 mg (2.19 mmol) 3-[(5-bromo-thiophen-2-yl)-carbonylamino]-tetrahydro-furan-3-carboxylic acid are combined with 890.0 mg (2.34 mmol) HATU and 601.0 µl (5.47 mmol) NMM in 10 ml DMF with stirring at room temperature and stirred for 10 min. Then 385.0 mg (2.19 mmol) 3-methyl-2,3,4,5-tetrahydro-1H-benzo[d]azepin-7-ylamine are added and the mixture is stirred overnight at 65° C. The reaction mixture is combined with water and sat. Sodium hydrogen carbonate solution, the precipitate is filtered off and purified by chromatography on aluminium oxide (eluant: dichloromethane/ethanol 100:0 to 98:2).

Yield: 850.0 mg (81%)
$R_f$ value: 0.62 (aluminium oxide; dichloromethane/ethanol=95:5)
$C_{21}H_{24}BrN_3O_3S$ (478.40)
Mass spectrum: $(M+H)^+=478/480$ (bromine isotopes)

Example 2

3-[(5-chloro-thiophen-2-yl)-carbonylamino]-N-(3-methyl-2,3,4,5-tetrahydro-1H-benzo[d]azepin-7-yl)-tetrahydrofuran-3-carboxylic acid amide

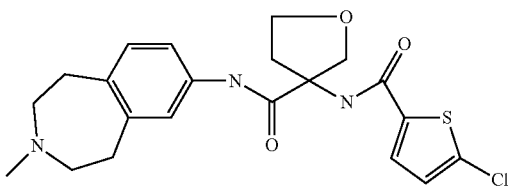 [SMILES: CN1CCc2ccc(NC(=O)C3(NC(=O)c4ccc(Cl)s4)CCOC3)cc2CC1]

(a) benzyl 3-[(5-chloro-thiophen-2-yl)-carbonylamino]-tetrahydro-furan-3-carboxylate 1.59 g (9.8 mmol) 5-chloro-thiophene-2-carboxylic acid is dissolved in 30 ml DMF and stirred with 3.61 g (10.7 mmol) benzyl 3-amino-tetrahydro-furan-3-carboxylate and 3.46 g (10.8 mmol) TBTU and 4.3 ml (39 mmol) NMM at room temperature for 20 h. Then the mixture is evaporated down and purified by chromatography on silica gel (eluant: dichloromethane/ethanol 100:0 to 94:6).

Yield: quantitative
$R_f$ value: 0.59 (silica gel; dichloromethane/ethanol=9:1)
$C_{17}H_{16}ClNO_4S$ (365.83)
Mass spectrum: $(M+H)^+=366/368$ (chlorine isotopes)

(b) 3-[(5-chloro-thiophen-2-yl)-carbonylamino]-tetrahydro-furan-3-carboxylic acid 3.6 g (9.8 mmol) benzyl 3-[(5-chloro-thiophen-2-yl)-carbonylamino]-tetrahydro-furan-3-carboxylate are dissolved in 60 ml of ethanol and combined with 39.1 ml (39.1 mmol) 1-molar aqueous sodium hydroxide solution and stirred for 6 h at room temperature. After evaporation i. vac. The residue is combined with 1-molar aqueous hydrochloric acid while cooling with an ice bath, the precipitate is suction filtered and dried at 60° C. in the vacuum drying cupboard.

Yield: 2.5 g (91%)
$R_f$ value: 0.13 (silica gel; dichloromethane/ethanol 9:1)
$C_{10}H_{10}ClNO_4S$ (275.71)
Mass spectrum: $(M-H)^-=274/276$ (chlorine isotopes)

(c) 3-[(5-chloro-thiophen-2-yl)-carbonylamino]-N-(3-methyl-2,3,4,5-tetrahydro-1H-benzo[d]azepin-7-yl)-tetrahydrofuran-3-carboxylic acid amide Prepared analogously to Example 2(a) from 3-[(5-chloro-thiophen-2-yl)-carbonylamino]-tetrahydro-furan-3-carboxylic acid and 3-methyl-2,3,4,5-tetrahydro-1H-benzo[d]azepin-7-ylamine with TBTU and TEA in THF at room temperature with subsequent purification by chromatography with aluminium oxide (eluant: dichloromethane/ethanol 100:0 to 97:3).

Yield: 67%
$R_f$ value: 0.63 (aluminium oxide; dichloromethane/ethanol=95:5)
$C_{21}H_{24}ClN_3O_3S$ (433.95)
Mass spectrum: $(M+H)^+=434/436$ (chlorine isotopes)

Example 3

5-chloro-thiophene-2-carboxylic acid-N-[1-(3-cyclopropyl-2,3,4,5-tetrahydro-1H-benzo[d]azepin-7-ylcarbamoyl)-1-methyl-ethyl]-amide

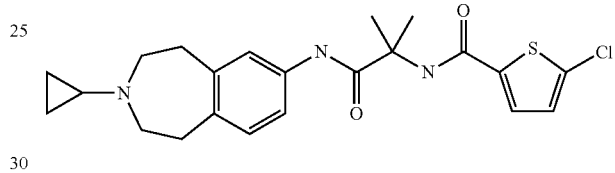

(a) 2-(5-chloro-thiophen-2-yl)-4,4-dimethyl-4H-oxazol-5-one 1.0 g (4.0 mmol) 2-[(5-chloro-thiophen-2-yl)-carbonylamino]-2-methyl-propionic acid in 30 ml acetic anhydride are stirred for 1 h at 85° C. Then the reaction mixture is evaporated to dryness.

Yield: 927.3 mg (100%)
$C_9H_8ClNO_2S$ (229.68)
Mass spectrum: $(M+H)^+=230$ (b) 5-chloro-thiophene-2-carboxylic acid-N-[1-(3-cyclopropyl-2,3,4,5-tetrahydro-1H-benzo[d]azepin-7-ylcarbamoyl)-1-methyl-ethyl]-amide 200.0 µl (10.0 µmol) of a 0.05 molar 2-(5-chloro-thiophen-2-yl)-4,4-dimethyl-4H-oxazol-5-one solution in toluene/acetic acid 9:1 are combined with 200.0 µl (10.0 µmol) of a 0.05-molar 3-cyclopropyl-2,3,4,5-tetrahydro-1H-benzo[d]azepin-7-ylamine solution in DMF and 1.7 µl (10.0 µmol) DIPEA, heated to 80° C. overnight and left to stand for 2 days at room temperature. The reaction solution is filtered through basic aluminium oxide and the filtrate is evaporated down i. vac.

Yield: quantitative
$R_t$ value: 3.31 min (HPLC-MS, method 1)
$C_{22}H_{26}ClN_3O_2S$ (431.99)
Mass spectrum: $(M+H)^+=432/434$ (chlorine isotopes)

Example 4

5-chloro-thiophene-2-carboxylic acid-N-{1-methyl-1-[3-(2,2,2-trifluoro-acetyl)-2,3,4,5-tetrahydro-1H-benzo[d]azepin-7-ylcarbamoyl]-ethyl}-amide

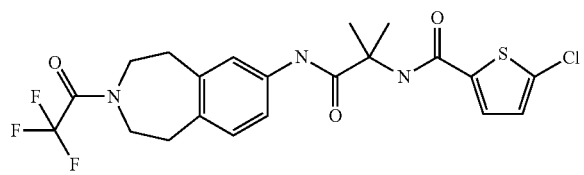 [SMILES: CC(C)(NC(=O)c1ccc(Cl)s1)C(=O)Nc1ccc2c(c1)CCN(C(=O)C(F)(F)F)CC2]

(a) 2-[(5-chloro-thiophen-2-yl)-carbonylamino]-2-methyl-propionic acid 4.5 g (27.7 mmol) 5-chloro-thiophene-2-carboxylic acid are combined with 8.0 ml (110.7 mmol) thionyl chloride in 250 ml dichloromethane with stirring at room temperature and stirred for 3 h at reflux temperature. Then the reaction mixture is evaporated to dryness.

2.9 g (27.7 mmol) 2-amino-isobutyric acid are combined with 8.0 ml (30.4 mmol) N,O-bis-(trimethylsilyl)-trifluoro-acetamide in 300 ml acetonitrile with stirring and stirred for 3.5 h at reflux temperature. The reaction mixture is combined with 8.5 ml (60.9 mmol) TEA and the solution of the prepared acid chloride in 75 ml acetonitrile, stirred for 15 min at reflux temperature and then slowly cooled to room temperature. The reaction mixture is evaporated to dryness i. vac., the residue is mixed with water and 2-molar sodium carbonate solution and washed with diethyl ether. The aqueous phase is adjusted to pH 1 with 20 ml conc. Hydrochloric acid, the precipitate is suction filtered and dried at 50° C. in the vacuum drying cupboard.

Yield: 5.9 g (86%)

$C_9H_{10}ClNO_3S$ (247.70)

Mass spectrum: $(M+H)^+$=248/250 (chlorine isotopes)

(b) 5-chloro-thiophene-2-carboxylic acid-N-{1-methyl-1-[3-(2,2,2-trifluoro-acetyl)-2,3,4,5-tetrahydro-1H-benzo[d]azepin-7-ylcarbamoyl]-ethyl}-amide Prepared analogously to Example 2-c from 2-[(5-chloro-thiophen-2-yl)-carbonylamino]-2-methyl-propionic acid and 3-(2,2,2-trifluoroacetyl)-2,3,4,5-tetrahydro-1H-benzo[d]azepin-7-yl)-amine with TBTU and NMM in DMF at room temperature with subsequent filtration through aluminium oxide.

Yield: (95%)

$R_f$ value: 0.65 (silica gel; dichloromethane/ethanol=9:1)

$C_{21}H_{21}ClF_3N_3O_3S$ (487.92)

Mass spectrum: $(M-H)^-$=486/488 (chlorine isotopes)

Example 5

5-chloro-thiophene-2-carboxylic acid-N-[1-methyl-1-(2,3,4,5-tetrahydro-1H-benzo[d]azepin-7-ylcarbamoyl)-ethyl]-amide

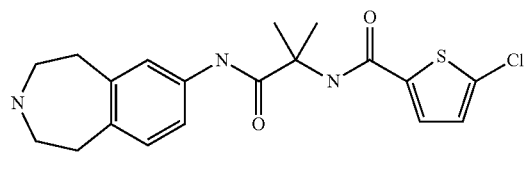 [SMILES: CC(C)(NC(=O)c1ccc(Cl)s1)C(=O)Nc1ccc2c(c1)CCNCC2]

500.0 mg (1.03 mmol) 5-chloro-thiophene-2-carboxylic acid-N-{1-methyl-1-[3-(2,2,2-trifluoro-acetyl)-2,3,4,5-tetrahydro-1H-benzo[d]azepin-7-ylcarbamoyl]-ethyl}-amide are combined with 637.0 mg (4.61 mmol) potassium carbonate in 15 ml of methanol and 10 ml of water with stirring at room temperature and stirred for 3 h at reflux temperature. The reaction mixture is evaporated down i. vac., the residue is combined with water, the precipitate is filtered off and dried in the vacuum drying cupboard at 50° C.

Yield: 340.0 mg (85%)

$R_f$ value: 0.20 (silica gel; dichloromethane/methanol/conc. Ammonia solution=80:20:2)

$C_{19}H_{22}ClN_3O_2S$ (391.92)

Mass spectrum: $(M+H)^-$=390/392 (chlorine isotopes)

Example 6

5-chloro-thiophene-2-carboxylic acid-N-[1-(3-acetyl-2,3,4,5-tetrahydro-1H-benzo[d]azepin-7-ylcarbamoyl)-1-methyl-ethyl]-amide

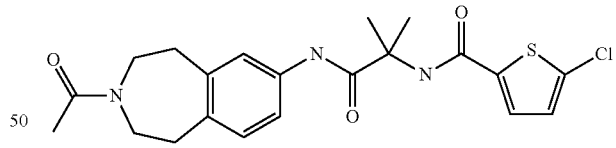

100.0 mg (0.26 mmol) 5-chloro-thiophene-2-carboxylic acid-N-[1-methyl-1-(2,3,4,5-tetrahydro-1H-benzo[d]azepin-7-ylcarbamoyl)-ethyl]-amide are combined with 43.0 µl (0.31 mmol) TEA and 27.0 µl (0.29 mmol) acetic anhydride in 5 ml THF with stirring at room temperature and stirred for 2 h at room temperature. The reaction mixture is mixed with water, the precipitate is filtered off and dried in the vacuum drying cupboard at 50° C.

Yield: 80.0 mg (72%)

$R_f$ value: 0.90 (silica gel; dichloromethane/methanol/conc. Ammonia solution=80:20:2)

$C_{21}H_{24}ClN_3O_3S$ (433.95)

Mass spectrum: $(M+H)^+$=434/436 (chlorine isotopes)

Example 7

5-chloro-thiophene-2-carboxylic acid-N-[1-(3-ethyl-2,3,4,5-tetrahydro-1H-benzo[d]azepin-7-ylcarbamoyl)-1-methyl-ethyl]-amide

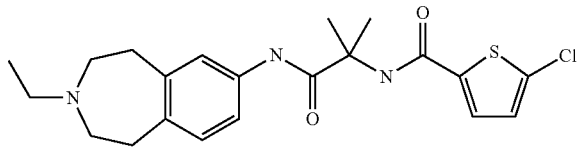 [SMILES: CCN1CCc2ccc(NC(=O)C(C)(C)NC(=O)c3ccc(Cl)s3)cc2CC1]

100.0 mg (0.26 mmol) 5-chloro-thiophene-2-carboxylic acid-N-[1-methyl-1-(2,3,4,5-tetrahydro-1H-benzo[d]azepin-7-ylcarbamoyl)-ethyl]-amide in 5 ml acetone are combined with 74.0 mg (0.54 mmol) potassium carbonate and 21.0 μl (0.26 mmol) iodoethane with stirring at room temperature and stirred for 3 h at reflux temperature. The reaction mixture is mixed with water at room temperature, the precipitate is filtered off and dried in the vacuum drying cupboard at 50° C.

Yield: 60.0 mg (56%)
$R_f$ value: 0.30 (silica gel; dichloromethane/methanol/conc. Ammonia solution=80:20:2)
$C_{21}H_{26}ClN_3O_2S$ (419.97)
Mass spectrum: $(M+H)^+$=420/422 (chlorine isotopes)

Example 8

5-ethynyl-N-[1-methyl-1-(3-methyl-2,3,4,5-tetrahydro-1H-benzo[d]azepin-7-ylcarbamoyl)-ethyl]-thiophene-2-carboxylic acid amide

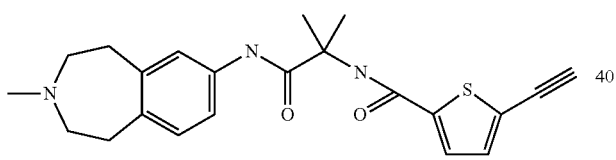

(a) ethyl 5-trimethylsilylethynyl-thiophene-2-carboxylate

Under an argon atmosphere a solution of 32.5 g (138.0 mmol) ethyl 5-bromo-thiophene-2-carboxylate in 320 ml acetonitrile and 640 ml THF is combined with 1.3 g (7.0 mmol) copper-(I)-iodide and 39.0 g (276.0 mmol) trimethylsilylacetylene with stirring, the mixture is stirred for 5 min and then 5.6 g (7.0 mmol) 1,1-bis-(diphenylphosphino)-ferrocene-dichloropalladium(II))-PdCl$_2$ in a complex with CH$_2$Cl$_2$ 1/1 and 57.4 ml (414.0 mmol) TEA are added. The reaction mixture is stirred overnight at room temperature, evaporated down i. vac., the residue is combined with ethyl acetate and washed with ammonia solution (5%) and water. The organic phase is dried on sodium sulphate and evaporated to dryness i. vac. The residue is combined with diethyl ether, the precipitate is suction filtered and dried.

Yield: quantitative
$R_f$ value: 0.71 (silica gel; petroleum ether/ethyl acetate=8:2)
$C_{12}H_{16}O_2SSi$ (252.41)
Mass spectrum: $(M+H)^+$=253

(b) 5-ethynyl-thiophene-2-carboxylic acid

The solution of 36.2 g (114.0 mmol) ethyl 5-trimethylsilanylethynyl-thiophene-2-carboxylate in 185 ml of ethanol is combined with 730.0 ml (1.46 mol) 2-molar aqueous sodium hydroxide solution and stirred overnight at 50° C. The reaction mixture is evaporated to dryness i. vac., combined with water and washed with dichloromethane. The aqueous phase is acidified with 6-molar aqueous hydrochloric acid while cooling with an ice bath, the precipitate is filtered off and dried at 50° C. in the vacuum drying cupboard.

Yield: 8.9 g (41%)
$R_f$ value: 0.64 (RP-8; methanol/NaCl solution (5%)=6:4)
$CO_7H_4O_2S$ (152.17)
Mass spectrum: $(M-H)^-$=151

(c) methyl 2-[(5-ethynyl-thiophen-2-yl)-carbonylamino]-2-methyl-propionate

A solution of 6.0 g (39.4 mmol) 5-ethynyl-thiophene-2-carboxylic acid in 180 ml THF is combined with 20.6 ml (118.3 mmol) DIPEA and 13.9 g (43.3 mmol) TBTU with stirring and stirred for 10 min. Then 6.1 g (39.4 mmol) methyl 2-amino-isobutyrate hydrochloride is added and the mixture is stirred overnight at room temperature. The reaction mixture is evaporated to dryness i. vac., mixed with ethyl acetate and washed with water and sodium hydrogen carbonate solution (5%). The organic phase is dried with sodium sulphate and evaporated down i.vac.

Yield: 9.3 g (94%)
$R_f$ value: 0.71 (silica gel; dichloromethane/ethanol=9:1)
$C_{12}H_{13}NO_3S$ (251.30)
Mass spectrum: $(M+H)^+$=252

(d) 2-[(5-ethynyl-thiophen-2-yl)-carbonylamino]-2-methyl-propionic acid 9.3 g (37.1 mmol) methyl 2-[(5-ethynyl-thiophen-2-yl)-carbonylamino]-2-methyl-propionate are dissolved in 550 ml of water and 370 ml THF and combined with 74.2 ml (74.2 mmol) 1-molar aqueous lithium hydroxide solution and stirred for 2 h at room temperature. THF is distilled off i. vac. And the residue is extracted with dichloromethane. The aqueous phase is acidified with 3-molar aqueous hydrochloric acid, the precipitate is filtered off and dried at 50° C. in the vacuum drying cupboard.

Yield: 8.4 g (95%)
$R_f$ value: 0.20 (silica gel; dichloromethane/ethanol=9:1)
$C_{11}H_{11}NO_3S$ (237.28)
Mass spectrum: $(M+H)^+$=238 e) 2-(5-ethynyl-thiophen-2-yl)-4,4-dimethyl-4H-oxazol-5-one

Prepared analogously to Example 3-a from 2-[(5-ethynyl-thiophen-2-yl)-carbonylamino]-2-methyl-propionic acid in acetic anhydride at 65° C. with subsequent purification by chromatography on silica gel with the eluant (petroleum ether/ethyl acetate=2:1).

Yield: 3.1 g (84%)
$R_f$ value: 0.67 (silica gel; petroleum ether/ethyl acetate=7:3)
$C_{11}H_9NO_2S$ (219.26)
Mass spectrum: $(M+H)^+$=220 f) 5-ethynyl-N-[1-methyl-1-(3-methyl-2,3,4,5-tetra-hydro-1H-benzo[d]azepin-7-ylcarbamoyl)-ethyl]-thiophene-2-carboxylic acid amide A solution of 150.0 mg (0.7 mmol) 2-(5-ethynyl-thiophen-2-yl)-4,4-dimethyl-4H-oxazol-5-one in 7.5 ml of toluene and 850.0 µl acetic acid is combined with a solution of 134.2 mg (0.8 mmol) 3-methyl-2,3,4,5-tetrahydro-1H-benzo[d]azepin-7-ylamine in 8.5 ml DMF with stirring and stirred overnight at 65° C. The reaction mixture is evaporated to dryness i. vac., dissolved in dichloromethane and ethanol and filtered through aluminium oxide. The filtrate is combined with water, the precipitate is suction filtered and dried at 55° C. in the vacuum drying cupboard.

Yield: 260.0 mg (96%)

$R_f$ value: 0.43 (RP-8; methanol/NaCl solution (5%)=6:4)

$C_{22}H_{25}N_3O_2S$ (395.52)

Mass spectrum: $(M+H)^+=396$

Example 9

5-chloro-thiophene-2-carboxylic acid-N-[1-methyl-1-(4-oxo-2,3,4,5-tetrahydro-1H-benzo[d]azepin-7-ylcarbamoyl)-1-methyl-ethyl]-amide/5-chloro-thiophene-2-carboxylic acid-N-[1-methyl-1-(2-oxo-2,3,4,5-tetrahydro-1H-benzo[d]azepin-7-ylcarbamoyl)-1-methyl-ethyl]-amide

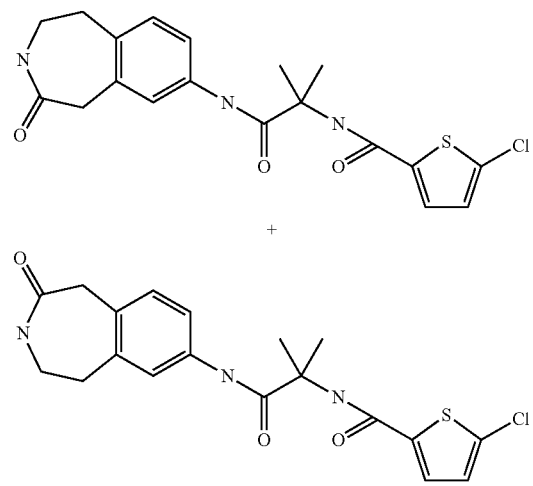 [SMILES: CC(C)(NC(=O)c1ccc(Cl)s1)C(=O)Nc1ccc2c(c1)CC(=O)NCC2 ; CC(C)(NC(=O)c1ccc(Cl)s1)C(=O)Nc1ccc2c(c1)CCNC(=O)C2]

(a) 3-trifluoroacetyl-7-nitro-2,3,4,5-tetrahydro-1H-benzo[d]azepine 12.5 g (51.39 mmol) 3-trifluoroacetyl-2,3,4,5-tetrahydro-1H-benzo[d]azepine in 30 ml acetic anhydride are dissolved in 18.9 ml (352.0 mmol) sulphuric acid (conc.) and at −5° C. to 0° C. slowly combined with 3.6 ml (51.39 mmol) nitric acid (65%) and stirred for 1 h at 0° C. The reaction mixture is added to water, extracted with ethyl acetate, the organic phase is dried on sodium sulphate and evaporated to dryness. The residue is recrystallised from ethanol.

Yield: 10.4 g (70%)

$R_f$ value: 0.78 (silica gel; dichloromethane/ethanol=95:5)

$C_{12}H_{11}F_3N_2O_3$ (288.22)

Mass spectrum: $(M+H)^+=289$

(b) tert. Butyl 7-nitro-2,3,4,5-tetrahydro-benzo[d]azepin-3-carboxylate 5.0 g (17.34 mmol) 3-trifluoroacetyl-7-nitro-2,3,4,5-tetrahydro-1H-benzo[d]azepine in 50 ml THF are combined with 10.4 ml (20.81 mmol) 2-molar sodium hydroxide solution and stirred for 30 min at room temperature. The reaction solution is combined with 1.88 g (17.69 mmol) sodium carbonate and 5.0 ml of water and while cooling with an ice bath a solution of 3.98 g (18.21 mmol) di-tert.-butyl-dicarbonate in 15 ml THF is metered in and the mixture is stirred for 1 h at room temperature. Then the insoluble matter is filtered off, the filtrate is combined with ethyl acetate and washed with sat. Sodium chloride solution. The organic phase is dried on sodium sulphate and the filtrate is evaporated to dryness i. vac.

Yield: quantitative $R_f$ value: 0.81 (silica gel; dichloromethane/ethanol=95:5)

$C_{15}H_{20}N_2O_4$ (292.33)

Mass spectrum: (M-isobuten+H)+=237

(c) 8-nitro-1,3,4,5-tetrahydro-benzo[d]azepin-2-one/7-nitro-1,3,4,5-tetrahydro-benzo[d]azepin-2-one 5.1 g (17.3 mmol) tert. Butyl 7-nitro-2,3,4,5-tetrahydro-benzo[d]azepine-3-carboxylate in 50 ml of ethyl acetate and 70 ml of water are combined with 8.9 g (41.63 mmol) sodium metaperiodate, 0.54 g (2.60 mmol) ruthenium chloride*$H_2O$ with vigorous stirring and stirred for 3.5 h at room temperature. Then the insoluble matter is filtered off, the filtrate is combined with ethyl acetate and washed with sodium disulphite solution (10%) and sat. Sodium chloride solution. The organic phase is dried on sodium sulphate and the filtrate is evaporated to dryness i. vac. The residue is dissolved in 60 ml dichloromethane, 6.0 ml TFA are added and the mixture is stirred overnight. The reaction solution is evaporated to dryness i. vac., combined with dichloromethane, washed with water and sat sodium hydrogen carbonate solution, dried on sodium sulphate and evaporated to dryness i. vac.

Yield: 2.3 g (65%)

$R_f$ value: 0.52 (silica gel; dichloromethane/ethanol=9:1)

$C_{10}H_{10}N_2O_3$ (206.20)

Mass spectrum: $(M+H)^+=207$

(d) 8-amino-1,3,4,5-tetrahydro-benzo[d]azepin-2-one/7-amino-1,3,4,5-tetrahydro-benzo[d]azepin-2-one 2.3 g (11.2 mmol) 8-nitro-1,3,4,5-tetrahydro-benzo[d]azepin-2-one/7-nitro-1,3,4,5-tetrahydro-benzo[d]azepin-2-one are dissolved in 40 ml of methanol and combined with 300 mg Pd/C 10%. The mixture is hydrogenated in a Parr apparatus at room temperature at 3 bar hydrogen pressure for 17 hours. Then the catalyst is filtered off and the filtrate is evaporated down i. vac.

Yield: 1.51 g (77%)

$R_f$ value: 0.10 (silica gel; dichloromethane/ethanol=95:5)

$C_{10}H_{12}N_2O$ (176.22)

Mass spectrum: $(M+H)^+=177$ (e) 5-chloro-thiophene-2-carboxylic acid-N-[1-methyl-1-(4-oxo-2,3,4,5-tetrahydro-1H-benzo[d]azepin-7-ylcarbamoyl)-1-methyl-ethyl]-amide/5-chloro-thiophene-2-carboxylic acid-N-[1-methyl-1-(2-oxo-2,3,4,5-tetrahydro-1H-benzo[d]azepin-7-ylcarbamoyl)-1-methyl-ethyl]-amide Prepared analogously to Example 1 from 2-[(5-chloro-thiophen-2-yl)-carbonylamino-2-methyl-propionic acid with HATU, NMM and 8-amino-1,3,4,5-tetrahydro-benzo[d]azepin-2-on/7-amino-1,3,4,5-tetrahydro-benzo[d]azepin-2-one in DMF with subsequent purification by chromatography on silica gel with the eluant (dichloromethane/ethanol 100:0 to 92:8).

Yield: quantitative
$R_f$ value: 0.40 (silica gel; dichloromethane/ethanol=9:1)
$C_{19}H_{20}ClN_3O_3S$ (405.90)
Mass spectrum: $(M+H)^+=406/408$ (chlorine isotopes)

The following compounds may be prepared analogously to Example 1:

| No. | Structural formula / Name | Yield Last Step | Mass peak(s) | $R_f$ value or $R_t$ |
|---|---|---|---|---|
| 10 | 5-chloro-thiophene-2-carboxylic acid-N-[1-methyl-1-(1,1,3-trimethyl-2,3,4,5-tetrahydro-1H-benzo[d]azepin-7-ylcarbamoyl)-ethyl}-amide | 68% | $(M + H)^+ =$ 434/436 (chlorine isotopes) | 0.33 (RP-8; methanol: 5% NaCl solution = 6:4) |
| 11 | 5-chloro-thiophene-2-carboxylic acid-N-[1-(7-ethyl-6,7,8,9-tetrahydro-5H-pyrazino[2,3-d]azepin-2-ylcarbamoyl)-1-methyl-ethyl]-amide | 1% | $(M + H)^+ =$ 422/424 (chlorine isotopes) | 0.17 (RP-8; methanol: 5% NaCl solution = 6:4) |
| 12 | 5-chloro-thiophene-2-carboxylic acid-N-[1-(1,1,3-trimethyl-2,3,4,5-tetrahydro-1H-benzo[d]azepin-7-ylcarbamoyl]-ethyl}-amide | 100% | $(M + H)^+ =$ 420/422 (chlorine isotopes) | 3.29 min (HPLC-MS) method 1 |
| 13 | 5-chloro-thiophene-2-carboxylic acid-N-[1-methyl-1-(3-methyl-2,3,4,5-tetrahydro-1H-benzo[d]azepin-7-ylcarbamoyl)-ethyl}-amide | 64% | $(M + H)^+ =$ 406/408 (chlorine isotopes) | 0.40 (RP-8; methanol: 5% NaCl solution = 6:4) |
| 14 | 5-bromo-thiophene-2-carboxylic acid-N-[1-methyl-1-(3-methyl-2,3,4,5-tetrahydro-1H-benzo[d]azepin-7-ylcarbamoyl)-ethyl}-amide | 99% | $(M + H)^+ =$ 450/452 (bromine isotopes) | 0.40 (RP-8; methanol: 5% NaCl solution = 6:4) |

-continued

| No. | Structural formula Name | Yield Last Step | Mass peak(s) | $R_f$ value or $R_t$ |
|---|---|---|---|---|
| 18 | 1-[(5-bromo-thiophen-2-yl)-carbonylamino]-N-(3-methyl-2,3,4,5-tetrahydro-1H-benzo[d]azepin-7-yl)-cyclopentane-1-carboxylic acid amide | 42% | (M + H)+ = 476/78 (bromine isotopes) | 0.61 (aluminum oxide; di-chloro-methane/ ethanol = 95:5) |
| 19 | 1-[(5-chloro-thiophen-2-yl)-carbonylamino]-N-(3-methyl-2,3,4,5-tetrahydro-1H-benzo[d]azepin-7-yl)-cyclopentane-1-carboxylic acid amide | 75% | (M + H)+ = 432/434 (chlorine isotopes) | 0.32 (RP-8; methanol/ 5% NaCl solution = 6:4) |
| 20 | 3-[(5-chloro-thiophen-2-yl)-carbonylamino]-N-(3-methyl-2,3,4,5-tetrahydro-1H-benzo[d]azepin-7-yl)-tetrahydrothiophene-3-carboxylic acid amide | 62% | (M + H)+ = 450/52 (chlorine isotopes) | |
| 21 | 5-chloro-thiophene-2-carboxylic acid-N-[1-(3-methyl-2,3,4,5-tetrahydro-1H-benzo[d]azepin-7-ylcarbamoyl]-ethyl}-amide | 48% | (M + H)+ = 392/94 (chlorine isotopes) | |
| 22 | (R)-5-chloro-thiophene-2-carboxylic acid-N-[1-(3-methyl-2,3,4,5-tetrahydro-1H-benzo[d]azepin-7-ylcarbamoyl]-1-phenyl-methyl}-amide | 26% | (M − H)− = 452/4 (chlorine isotopes) | 0.45 (RP-8; methanol/ 5% NaCl solution = 6:4) |

-continued

| No. | Structural formula Name | Yield Last Step | Mass peak(s) | $R_f$ value or $R_t$ |
|---|---|---|---|---|
| 23 | 5-chloro-thiophene-2-carboxylic acid-N-[3-tert.-butoxycarbonyl-1-(3-methyl-2,3,4,5-tetrahydro-1H-benzo[d]azepin-7-ylcarbamoyl]-propyl}-amide | 57% | (M + H)+ = 506/08 (chlorine isotopes) | |
| 24 | 5-chloro-thiophene-2-carboxylic acid-N-[2-hydroxy-1-(3-methyl-2,3,4,5-tetrahydro-1H-benzo[d]azepin-7-ylcarbamoyl]-ethyl}-amide | 2% | (M + H)+ = 408/10 (chlorine isotopes) | 0.48 (RP-8; methanol/ 5% NaCl solution = 6:4) |
| 25 | 5-chloro-thiophene-2-carboxylic acid-N-[3-hydroxy-1-(3-methyl-2,3,4,5-tetrahydro-1H-benzo[d]azepin-7-ylcarbamoyl]-propyl}-amide | 20% | (M + H)+ = 422/24 (chlorine isotopes) | 0.51 (RP-8; methanol/ 5% NaCl solution = 6:4) |
| 26 | 5-chloro-thiophene-2-carboxylic acid-N-[1-(3-methyl-2,3,4,5-tetrahydro-1H-benzo[d]azepin-7-ylcarbamoyl]-but-2-enyl}-amide | 71% | (M + H)+ = 418/20 (chlorine isotopes) | |
| 27 | 5-chloro-thiophene-2-carboxylic acid-N-[2-(1,2,4-triazol-1-yl)-1-(3-methyl-2,3,4,5-tetrahydro-1H-benzo[d]azepin-7-ylcarbamoyl]-ethyl}-amide | 55% | (M + H)+ = 459/61 (chlorine isotopes) (M − H)− = 457/9 (chlorine isotopes) | 0.46 (RP-8; methanol/ 5% NaCl solution = 6:4) |

-continued

| No. | Structural formula / Name | Yield Last Step | Mass peak(s) | $R_f$ value or $R_t$ |
|---|---|---|---|---|
| 28 | 5-chloro-thiophene-2-carboxylic acid-N-[2-(1-benzyl-imidazol-4-yl)-1-(3-methyl-2,3,4,5-tetrahydro-1H-benzo[d]azepin-7-ylcarbamoyl]-ethyl}-amide | | | |
| 29 | 5-chloro-thiophene-2-carboxylic acid-N-[3-methylsulphanyl-1-(3-methyl-2,3,4,5-tetrahydro-1H-benzo[d]azepin-7-ylcarbamoyl)-propyl}-amide | 54% | (M + H)+ = 452/54 (chlorine isotopes) | |
| 34 | 1-[(5-chloro-thiophen-2-yl)carbonylamino]-N-(3-methyl-2,3,4,5-tetrahydro-1H-benzo[d]azepin-7-yl)-cyclohexane-1-carboxylic acid amide | 8% | (M + H)+ = 446/8 (chlorine isotopes) | 0.79 (aluminum oxide; dichloromethane/ ethanol = 95:5) |

The following compounds may be prepared analogously to Example 2:

| No. | Structural formula / Name | Yield Last Step | Mass peak(s) | $R_f$ value or $R_t$ |
|---|---|---|---|---|
| 15 | 5-chloro-thiophene-2-carboxylic acid-N-[2-methoxy-1-(3-methyl-2,3,4,5-tetrahydro-1H-benzo[d]azepin-7-ylcarbamoyl)-ethyl]-amide | 86% | (M + H)+ = 422/424 chlorine isotopes | 0.52 (aluminum oxide; dichloromethane/ ethanol = 95:5) |

-continued

| No. | Structural formula / Name | Yield Last Step | Mass peak(s) | $R_f$ value or $R_t$ |
|---|---|---|---|---|
| 30 | 1-[(5-chloro-thiophen-2-yl)carbonylamino]-N-(3-methyl-2,3,4,5-tetrahydro-1H-benzo[d]azepin-7-yl)-cyclopropane-1-carboxylic acid amide | 40% | $(M + H)^+$ = 404/406 chlorine isotopes | 0.41 (RP-8; methanol/ 5% NaCl solution = 6:4) |
| 31 | 1-[(5-chloro-thiophen-2-yl)carbonylamino]-N-(3-methyl-2,3,4,5-tetrahydro-1H-benzo[d]azepin-7-yl)-cyclobutane-1-carboxylic acid amide | 60% | $(M + H)^+$ = 418/420 chlorine isotopes | 0.62 (silica gel dichloro- methane/ ethanol/ ammonia = 80:20:2) |
| 32 | 1-[(5-chloro-thiophen-2-yl)carbonylamino]-N-(3-methyl-2,3,4,5-tetrahydro-1H-benzo[d]azepin-7-yl)-cyclopent-3-ene-1-carboxylic acid amide | 70% | $(M + H)+$ = 430/32 (chlorine isotopes) $(M - H)-$ = 428/30 (chlorine isotopes) | 0.34 (RP-8; methanol/ 5% NaCl solution = 6:4) |
| 33 | 1-[(5-bromo-thiophen-2-yl)carbonylamino]-N-(3-methyl-2,3,4,5-tetrahydro-1H-benzo[d]azepin-7-yl)-cyclopent-3-ene-1-carboxylic acid amide | 85% | $(M + H)+$ = 474/6 (bromine isotopes) | 0.32 (RP-8; methanol/ 5% NaCl solution = 6:4) |

The following compounds may be prepared analogously to Example 8:

| No. | Structural formula / Name | Yield Last Step | Mass peak(s) | $R_f$ value or $R_t$ |
|---|---|---|---|---|
| 16 | 5-ethynyl-N-[1-(3-cyclopropyl-2,3,4,5-tetrahydro-4H-benzo[d]azepin-7-ylcarbamoyl)-1-methyl-ethyl]-thiophene-2-carboxylic acid amide | quantitative | $(M + H)^+$ = 422 | 3.27 min (HPLC-MS; method 2) |

| No. | Structural formula Name | Yield Last Step | Mass peak(s) | $R_f$ value or $R_t$ |
|---|---|---|---|---|
| 17 | 5-ethynyl-N-[1-methyl-(1,1,3-trimethyl-2,3,4,5-tetrahydro-4H-benzo[d]azepin-7-ylcarbamoyl)-ethyl]-thiophene-2-carboxylic acid amide | quantitative | $(M+H)^+ = 424$ | 3.29 min (HPLC-MS; method 2) |

Example 35

5-chloro-thiophene-2-carboxylic acid-N-[3-hydroxy-carbonyl-1-(3-methyl-2,3,4,5-tetrahydro-1H-benzo[d]azepin-7-ylcarbamoyl]propyl-amide

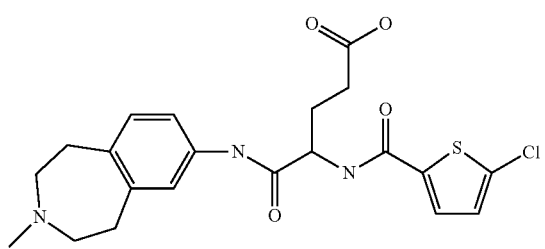 [SMILES: CN1CCc2ccc(NC(=O)C(CCC(=O)O)NC(=O)c3ccc(Cl)s3)cc2CC1]

93 mg (0.15 mmol) 5-chloro-thiophene-2-carboxylic acid-N-[3-tert.-butoxycarbonyl-1-(3-methyl-2,3,4,5-tetrahydro-1H-benzo[d]azepin-7-ylcarbamoyl]-propyl}-amide are combined with 1 ml trifluoroacetic acid in 1 ml dichloromethane with stirring at RT and stirred for 1.5 h at room temperature and concentrated by evaporation.

Yield: 78.0 mg (92%)
$C_{21}H_{24}ClN_3O_4S$ (449.959)
Mass spectrum: $(M+H)^+=450/52$ (chlorine isotopes)

Example 36

(R)-5-chloro-thiophene-2-carboxylic acid-N-[3-(1H-tetrazol-5-yl)-1-(3-methyl-2,3,4,5-tetrahydro-1H-benzo[d]azepin-7-ylcarbamoyl)-propyl]-amide

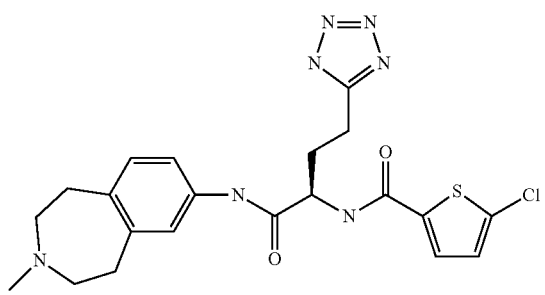 [SMILES: CN1CCc2ccc(NC(=O)[C@@H](CCc3nnn[nH]3)NC(=O)c3ccc(Cl)s3)cc2CC1]

(a)
(R)-2-tert.-butoxycarbonylamino-4-cyano-butyric acid 5.0 g (20.3 mmol) (R)—N-α-(tert.-butoxycarbonyl)-D-glutamine are combined with 2.30 ml (24.3 mmol) acetic anhydride in 55 ml of pyridine with stirring at room temperature and stirred for 20 h. The reaction mixture is evaporated down i. vac., the residue is combined with ethyl acetate and washed 3 times with 5% citric acid and 3 times with sat. NaCl solution. The organic phase is dried on sodium sulphate and concentrated by evaporation i.vac. Then it is purified by chromatography on silica gel (eluant: dichloromethane/methanol 90:10).

Yield: 3.16 g (68%)
$R_f$ value: 0.3 (silica gel; dichloromethane/methanol=9:1)
$C_{10}H_{16}N_2O_4$ (228.25)
Mass spectrum: $(M-H)^-=227$ (b) tert.butyl (R)-[3-cyano-1-(3-methyl-2,3,4,5-tetrahydro-1H-benzo[d]azepin-7-ylcarbamoyl)-propyl]-carbamate 1.0 g (4.0 mmol) (R)-2-tert.-butoxycarbonylamino-4-cyano-butyric acid is dissolved in 10 ml DMF and stirred with 1.29 g (4.03 mmol) TBTU and 2.79 ml (20.1 mmol) TEA at room temperature for 30 min. Then 1.0 g (4.01 mmol) 3-methyl-2,3,4,5-tetrahydro-1H-benzo[d]azepin-7-ylamine is added and the mixture is stirred overnight at 35° C. The reaction mixture is evaporated to dryness i. vac. And extracted with ethyl acetate. The organic phase is dried with sodium sulphate and evaporated down i. vac. Then it is purified by chromatography on silica gel (eluant: dichloromethane/methanol 95:5).

Yield: 450 mg (29%)
$R_f$ value: 0.15 (silica gel; dichloromethane/methanol=95:5)
$C_{21}H_{30}N_4O_3$ (386.49)
Mass spectrum: $(M+H)^+=387$ (c) tert.butyl (R)-[1-(3-methyl-2,3,4,5-tetrahydro-1H-benzo[d]azepin-7-ylcarbamoyl)-3-(1H-tetrazol-5-yl)-propyl]-carbamate 200 mg (0.52 mmol) tert.butyl (R)-[3-cyano-1-(3-methyl-2,3,4,5-tetrahydro-1H-benzo[d]azepin-7-ylcarbamoyl)-propyl]carbamate are placed in 1 ml DMF and combined with 80 mg (1.23 mmol) sodium azide and 66 mg (1.23 mmol) ammonium chloride. The reaction mixture is stirred overnight at 100° C., then acidified with TFA and separated using RP material (eluant: water/acetonitrile 95:5=>5:95).
Yield: 49.8 mg (18%)
$C_{21}H_{31}N_7O_3$ (429.53)
Mass spectrum: $(M+H)^+=430$ (d) (R)-2-amino-N-(3-methyl-2,3,4,5-tetrahydro-1H-benzo[d]azepin-7-yl)-4-(1H-tetrazol-5-yl)-butyramide 49.8 mg (90 µmol) tert.butyl (R)-[1-(3-methyl-2,3,4,5-tetrahydro-1H-benzo[d]azepin-7-ylcarbamoyl)-3-(1H-tetrazol-5-yl)-propyl]-carbamate are stirred in 1 ml of 2 molar aqueous hydrochloric acid at 50° C. for 2.5 h and then evaporated to dryness.
Yield: 32.7 mg (89%)
$C_{16}H_{23}N_7O$ (329.41)
Mass spectrum: $(M+H)^+=330$ (e) (R)-5-chloro-thiophene-2-carboxylic acid-N-[3-(1H-tetrazol-5-yl)-1-(3-methyl-2,3,4,5-tetrahydro-1H-benzo[d]azepin-7-ylcarbamoyl)-propyl]-amide 13 mg (0.08 mmol) 5-chloro-thiophene-2-carboxylic acid are dissolved in 0.5 ml DMF, mixed at room temperature with 26 mg (0.08 mmol) TBTU and 50 µl (0.45 mmol) NMM and stirred for 15 min. A solution of 32 mg (0.08 mmol) (R)-2-amino-N-(3-methyl-2,3,4,5-tetrahydro-1H-benzo[d]azepin-7-yl)-4-(1H-tetrazol-5-yl)-butyramide in 1 ml DMF is added to the reaction mixture and it is stirred overnight at room temperature. The reaction mixture is acidified with TFA, separated by chromatography through RP material (eluant: water/acetonitrile 95:5=>5:95) and then freeze-dried.
Yield: 18.8 mg (40%)
$R_f$ value: 2.29 min (HPLC-MS; method 2)
$C_{21}H_{24}ClN_7O_2S$ (473.99)
Mass spectrum: $(M+H)^+=474/6$ (chlorine isotopes)

Example 37

(R)-5-chloro-thiophene-2-carboxylic acid-N-[2-benzyloxy-1-(3-methyl-2,3,4,5-tetrahydro-1H-benzo[d]azepin-7-ylcarbamoyl)-ethyl]-amide

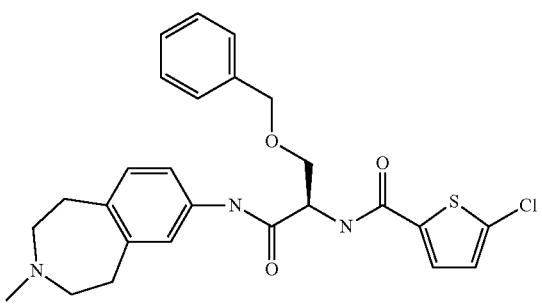 [SMILES: CN1CCc2ccc(NC(=O)[C@@H](COCc3ccccc3)NC(=O)c3ccc(Cl)s3)cc2CC1]

(a) (R) 2-amino-3-benzyloxy-N-(3-methyl-2,3,4,5-tetrahydro-1H-benzo[d]azepin-7-yl)-propionamide 0.117 g (0.60 mmol) (R)-3-benzyloxy-2-tert.-butoxycarbonylamino-propionic acid are reacted analogously to Example 2 (a) with 0.116 g (0.66 mmol) 3-methyl-2,3,4,5-tetrahydro-1H-benzo[d]azepin-7-ylamine, TBTU, DIPEA in THF. Then the BOC protective group is cleaved analogously to Example 1 (d), made basic with sodium hydroxide and extracted with ethyl acetate.
Yield: quantitative
$R_f$ value: 0.48 (RP-8; methanol/5% NaCl solution=6:4)
$C_{21}H_{27}N_3O_2$ (353.46)
Mass spectrum: $(M+H)^+=354$ (b) (R)-5-chloro-thiophene-2-carboxylic acid-N-[2-benzyloxy-1-(3-methyl-2,3,4,5-tetrahydro-1H-benzo[d]azepin-7-ylcarbamoyl)-ethyl]-amide 0.117 g (0.72 mmol) 5-chloro-thiophene-2-carboxylic acid are combined with 0.26 ml (3.60 mmol) thionyl chloride and 0.01 ml DMF in 15 ml dichloromethane with stirring at room temperature and refluxed for 2 h with stirring. Then the reaction mixture is evaporated down i.vac.
0.230 g (0.65 mmol) of (R) 2-amino-3-benzyloxy-N-(3-methyl-2,3,4,5-tetrahydro-1H-benzo[d]azepin-7-yl)-propionamide in 10 ml THF are combined with 0.27 ml (1.95 mmol) TEA and the solution of the prepared acid chloride in 10 ml THF at room temperature with stirring and stirred for 15 h. Then the mixture is diluted with ethyl acetate, washed with water, dried on sodium sulphate and concentrated by evaporation i.vac. The purification is carried out by chromatography through aluminium oxide (eluant: dichloromethane/ethanol 100:0=>98.5:1.5)
Yield: 0.14 g (43%)
$R_f$ value: 0.81 (aluminium oxide; dichloromethane/ethanol=95:5)
$C_{26}H_{28}ClN_3O_2S$ (498.04)
Mass spectrum: $(M+H)^+=498/00$ (chlorine isotopes)

Example 38

5-chloro-thiophene-2-carboxylic acid-N-[1-(3-isopropyl-2,3,4,5-tetrahydro-1H-benzo[d]azepin-7-ylcarbamoyl)-1-methyl-ethyl]-amide

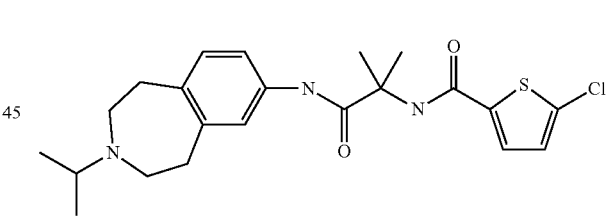

(a) 3-isopropyl-7-nitro-2,3,4,5-tetrahydro-1H-benzo[d]azepine 0.96 g (5.00 mmol) 7-nitro-2,3,4,5-tetrahydro-1H-benzo[d]azepine and 0.404 ml (5.50 mmol) acetone are dissolved in 20 ml THF, then 0.414 ml (7.50 mmol) acetic acid and 0.10 g p-toluenesulphonic acid are added and the mixture is stirred for 30 min at room temperature. At room temperature 1.378 g (6.50 mmol) sodium triacetoxyborohydride are added and stirred for 23 h. Then the mixture is made alkaline with sat. Sodium hydrogen carbonate solution and extracted with ethyl acetate, then the organic phase is dried with sodium sulphate and concentrated by evaporation i.vac.
Yield: quantitative
$C_{13}H_{18}N_2O_2$ (234.29)
Mass spectrum: $(M+H)^+=235$ (b) 3-isopropyl-2,3,4,5-tetrahydro-1H-benzo[d]azepin-7-ylamine Prepared analogously to Example 1 (c) from 3-isopropyl-7-nitro-2,3,4,5-tetrahydro-1H-benzo[d]azepine in methanol with Pd/C 10% at room temperature. Then the product is concentrated by evaporation.
Yield: 0.920 g (89%)
$R_f$ value: 0.14 (silica gel; dichloromethane/ethanol=9:1)
$C_{13}H_{20}N_2$ (204.31)
Mass spectrum: $(M+H)^+=205$ (c) 5-chloro-thiophene-2-carboxylic acid-N-[1-(3-isopropyl-2,3,4,5-tetrahydro-1H-benzo[d]azepin-7-ylcarbamoyl)-1-methyl-ethyl]-amide Prepared analogously to Example 1(f) from 3-isopropyl-2,3,4,5-tetrahydro-1H-benzo[d]azepin-7-ylamine and 2-[(5-chloro-thiophen-2-yl)-carbonylamino]-2-methyl-propionic acid with HATU and NMM in DMF at room temperature with subsequent chromatography through aluminium oxide (eluant: dichloromethane/ethanol 98:2) and through RP material (Zorbax StableBond C18; 7 μm 220 g; eluant: water/acetonitrile/formic acid=95:5:0.1=>10:90:0.1) and lyophilisation.
Yield: 0.386 g (40%)
$R_f$ value: 0.70 (aluminium oxide; dichloromethane/ethanol=95:5)
$C_{22}H_{28}ClN_3O_2S$ (434.0)
Mass spectrum: $(M+H)^+=434/6$ (chlorine isotopes)

Example 39

5-chloro-thiophene-2-carboxylic acid-N-[1-(8-methoxy-3-methyl-2,3,4,5-tetrahydro-1H-benzo[d]azepin-7-ylcarbamoyl)-1-methyl-ethyl]-amide

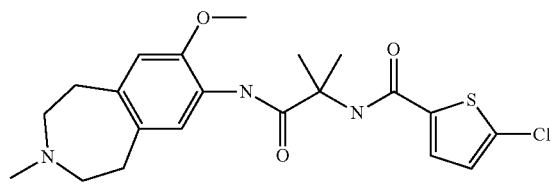 [SMILES: COc1cc2c(cc1NC(=O)C(C)(C)NC(=O)c1ccc(Cl)s1)CCN(C)CC2]

(a) 2,2,2-trifluoro-1-(7-methoxy-8-nitro-1,2,4,5-tetrahydro-benzo[d]azepin-3-yl)-ethanone 1.30 g (4.27 mmol) of 2,2,2-trifluoro-1-(7-hydroxy-8-nitro-1,2,4,5-tetrahydro-benzo[d]azepin-3-yl)-ethanone are dissolved in 20 ml DMF. At room temperature 0.59 g (4.27 mmol) potassium carbonate and 0.26 ml (4.27 mmol) methyliodide are added and the mixture is stirred overnight. Then it is filtered and the filtrate is concentrated by evaporation i.vac., the residue is triturated with water and suction filtered and dried in the circulating air dryer at 45° C.
Yield: 1.30 g (96%)
$R_f$ value: 0.59 (silica gel; petroleum ether/ethylacetate=1:1)
$C_{13}H_{13}F_3N_2O_4$ (318.25)
Mass spectrum: $(M+H)^+=319$ (b) 7-methoxy-8-nitro-2,3,4,5-tetrahydro-1H-benzo[d]azepine 1.30 g (4.08 mmol) 2,2,2-trifluoro-1-(7-methoxy-8-nitro-1,2,4,5-tetrahydro-benzo[d]azepin-3-yl)-ethanone and 3.06 ml (6.13 mmol) 2 molar sodium hydroxide solution are dissolved in 20 ml THF at room temperature and stirred for 3 h. Then the mixture is concentrated by evaporation i.vac., diluted with water and extracted with tert.-butyl-methylether. The organic phase is washed with 50% sodium hydroxide solution and sat. NaCl solution, dried on sodium sulphate and concentrated by evaporation i.vac.
Yield: 0.87 g (96%)
$R_f$ value: 0.15 (silica gel; petroleum ether/ethyl acetate=1:1)
$C_{11}H_{14}N_2O_3$ (222.24)
Mass spectrum: $(M+H)^+=223$ (c) 7-methoxy-3-methyl-8-nitro-2,3,4,5-tetrahydro-1H-benzo[d]azepine Prepared analogously to Example 1 (b) from 7-methoxy-8-nitro-2,3,4,5-tetrahydro-1H-benzo[d]azepine and aqueous formalin solution in formic acid.
Yield: 0.80 g (86%)
$R_f$ value: 0.59 (aluminium oxide; dichloromethane/ethanol=95:5)
$C_{12}H_{16}N_2O_3$ (236.27)
Mass spectrum: $(M+H)^+=237$ (d) 8-methoxy-3-methyl-2,3,4,5-tetrahydro-1H-benzo[d]azepin-7-ylamine Prepared analogously to Example 1 (c) from 7-methoxy-3-methyl-8-nitro-2,3,4,5-tetrahydro-1H-benzo[d]azepine with Pd/C 10% in methanol.
Yield: 0.67 g (96%)
$R_f$ value: 0.63 (aluminium oxide; dichloromethane/ethanol=95:5)
$C_{12}H_{18}N_{20}$ (236.27)
Mass spectrum: $(M+H)^+=207$ (e) 5-chloro-thiophene-2-carboxylic acid-N-[1-(8-methoxy-3-methyl-2,3,4,5-tetrahydro-1H-benzo[d]azepin-7-ylcarbamoyl)-1-methyl-ethyl]-amide Prepared analogously to Example 1 (f) from 8-methoxy-3-methyl-2,3,4,5-tetrahydro-1H-benzo[d]azepin-7-ylamine and 2-[(5-chloro-thiophen-2-yl)-carbonylamino]-2-methyl-propionic acid with HATU and NMM in DMF at room temperature. Then the mixture is concentrated by evaporation i.vac. And purified by chromatography through silica gel (eluant: dichloromethane/ethanol 100:0=>98:2).
Yield: 0.55 g (63%)
$R_f$ value: 0.61 (aluminium oxide; dichloromethane/ethanol=95:5)
$C_{21}H_{26}ClN_3O_3S$ (435.97)
Mass spectrum: $(M+H)^+=436/8$ (chlorine isotopes)

Example 40

5-chloro-thiophene-2-carboxylic acid-N-[1-(8-hydroxy-3-methyl-2,3,4,5-tetrahydro-1H-benzo[d]azepin-7-ylcarbamoyl)-1-methyl-ethyl]-amide

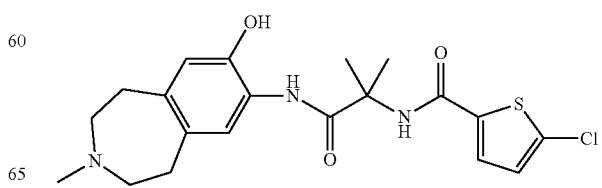

(a) 1-(7-benzyloxy-8-nitro-1,2,4,5-tetrahydro-benzo[d]azepin-3-yl)-2,2,2-trifluoro-ethanone 1.30 g (4.27 mmol) 2,2,2-trifluoro-1-(7-hydroxy-8-nitro-1,2,4,5-tetrahydro-benzo[d]azepin-3-yl)-ethanone are placed in 20 ml DMF and at room temperature 0.65 g (4.70 mmol) potassium carbonate and 0.508 ml (4.27 mmol) benzylbromide are added and the mixture is stirred for 3 h. Then it is filtered and the filtrate is concentrated by evaporation i.vac., the residue is triturated with water, suction filtered and dried at 45° C. in the circulating air dryer.
Yield: 1.67 g (99%)
$R_f$ value: 0.64 (silica gel; petroleum ether/ethyl acetate=7:3)
$C_{19}H_{17}F_3N_2O_4$ (394.34)
Mass spectrum: $(M+NH_4)^+=412$

(b) 7-benzyloxy-8-nitro-2,3,4,5-tetrahydro-1H-benzo[d]azepine

Prepared analogously to Example 39 (b) from 1-(7-benzyloxy-8-nitro-1,2,4,5-tetrahydro-benzo[d]azepin-3-yl)-2,2,2-trifluoro-ethanone.
Yield: 1.04 g (83%)
$R_f$ value: 0.46 (silica gel; petroleum ether/ethyl acetate=3:7)
$C_{17}H_{18}N_2O_3$ (298.34)
Mass spectrum: $(M+H)^+=299$

(c) 7-benzyloxy-3-methyl-8-nitro-2,3,4,5-tetrahydro-1H-benzo[d]azepine

Prepared analogously to Example 1 (b) from 7-benzyloxy-8-nitro-2,3,4,5-tetrahydro-1H-benzo[d]azepine and aqueous formalin solution in formic acid.
Yield: 1.08 g (99%)
$R_f$ value: 0.8 (aluminium oxide; dichloromethane/ethanol=95:5)
$C_{18}H_{20}N_2O_3$ (312.36)
Mass spectrum: $(M+H)^+=313$

(d) 8-amino-3-methyl-2,3,4,5-tetrahydro-1H-benzo[d]azepin-7-ol 0.50 g (1.60 mmol) 7-benzyloxy-3-methyl-8-nitro-2,3,4,5-tetrahydro-1H-benzo[d]azepine are dissolved in 20 ml of methanol and combined with 100 mg Pd/C 10%. Hydrogenation is carried out in a Parr apparatus at room temperature at 3 bar hydrogen pressure for 2 h. Then the catalyst is filtered off and the filtrate is concentrated by evaporation i.vac.
Yield: 0.26 g (84%)
$R_f$ value: 0.1 (aluminium oxide; dichloromethane/ethanol=95:5)
$C_{11}H_{16}N_2O$ (192.26)
Mass spectrum: $(M+H)^+=193$

(e) 5-chloro-thiophene-2-carboxylic acid-N-[1-(8-hydroxy-3-methyl-2,3,4,5-tetrahydro-1H-benzo[d]azepin-7-ylcarbamoyl)-1-methyl-ethyl]-amide Prepared analogously to Example 1 (f) from 8-amino-3-methyl-2,3,4,5-tetrahydro-1H-benzo[d]azepin-7-ol and 2-[(5-chloro-thiophen-2-yl)-carbonylamino]-2-methyl-propionic acid with HATU and NMM in DMF at room temperature. Then the mixture is concentrated by evaporation i.vac. And purified by chromatography through RP material (Zorbax StableBond C18; 8 μm; eluant: water with 1.5% formic acid/acetonitrile=95:5=>5:95).
Yield: 0.30 g (49%)
$R_f$ value: 0.40 (aluminium oxide; dichloromethane/ethanol=95:5)
$C_{20}H_{24}ClN_3O_3S$ (421.95)
Mass spectrum: $(M+H)^+=422/4$ (chlorine isotopes)

The following compounds may be prepared from optionally protected amino acid derivatives, benzazepine derivatives and thiophenecarboxylic acid derivatives analogously to the methods of synthesis described in the foregoing Examples:

| No. | Structural formula / Name | Yield (last step) | Mass peak(s) | $R_f$ value or $R_t$ |
|---|---|---|---|---|
| 41 | 5-chloro-thiophene-2-carboxylic acid-N-[1-(3-cyclobutyl-2,3,4,5-tetrahydro-1H-benzo[d]azepin-7-ylcarbamoyl)-1-methyl-ethyl]-amide | 32% | $(M+H)^+ = 446/448$ (chlorine isotopes) | Rt = 2.50 min HPLC-method 3a |
| 42 | 1-[(5-chloro-thiophen-2-yl)-carbonylamino]-N-(3-cyclobutyl-2,3,4,5-tetrahydro-1H-benzo[d]azepin-7-yl)-cyclopentane-1-carboxylic acid amide | 46% | $(M+H)^+ = 472/474$ (chlorine isotopes) | Rt = 2.66 min HPLC-method 3a |

| No. | Structural formula / Name | Yield (last step) | Mass peak(s) | $R_f$ value or $R_t$ |
|---|---|---|---|---|
| 43 | 1-[(5-chloro-thiophen-2-yl)-carbonylamino]-N-(3-cyclopropyl-2,3,4,5-tetrahydro-1H-benzo[d]azepin-7-yl)-cyclopentane-1-carboxylic acid amide | 49% | (M − H)+ = 458/460 (chlorine isotopes) | Rt = 4.41 min HPLC-method 3 |
| 44 | (S)-thiophene-2-carboxylic acid-N-[2-benzyloxy-1-(3-methyl-2,3,4,5-tetrahydro-1H-benzo[d]azepin-7-ylcarbamoyl)-ethyl]-amide | 70% | (M + H)⁺ = 464 | 0.31 (RP-8; methanol/5% NaCl solution = 6:4) |
| 45 | (S)-thiophene-2-carboxylic acid-N-[2-hydroxy-1-(3-methyl-2,3,4,5-tetrahydro-1H-benzo[d]azepin-7-ylcarbamoyl)-ethyl]-amide | 11% | (M + H)⁺ = 374 | 0.60 (RP-8; methanol/5% NaCl solution = 6:4) |
| 46 | 5-methyl-thiophene-2-carboxylic acid-N-[1-methyl-1-(3-methyl-2,3,4,5-tetrahydro-1H-benzo[d]azepin-7-ylcarbamoyl)-ethyl]-amide | 54% | (M − H)− = 386 | 0.63 (aluminum oxide; dichloromethane/ethanol = 95:5) |
| 47 | 5-formyl-thiophene-2-carboxylic acid-N-[1-methyl-1-(3-methyl-2,3,4,5-tetrahydro-1H-benzo[d]azepin-7-ylcarbamoyl)-ethyl]-amide | 42% | (M + H)⁺ = 400 | 0.66 (aluminum oxide; dichloromethane/ethanol = 95:5) |
| 48 | 5-chloro-thiophene-2-carboxylic acid-N-[(3-methyl-2,3,4,5-tetrahydro-1H-benzo[d]azepin-7-ylcarbamoyl)-methyl]-amide | 38% | (M + H)⁺ = 378/380 | 0.86 min (HPLC-MS; method 5) |

| No. | Structural formula Name | Yield (last step) | Mass peak(s) | $R_f$ value or $R_t$ |
|---|---|---|---|---|
| 49 | 5-bromo-thiophene-2-carboxylic acid-N-[(3-methyl-2,3,4,5-tetrahydro-1H-benzo[d]azepin-7-ylcarbamoyl)-methyl]-amide | 29% | $(M + H)^+ =$ 422/424 (bromine isotopes) | 0.88 min (HPLC-MS; method 5) |
| 50 | 5-methyl-thiophene-2-carboxylic acid-N-[(3-methyl-2,3,4,5-tetrahydro-1H-benzo[d]azepin-7-ylcarbamoyl)-methyl]-amide | 34% | $(M - H)^- =$ 358 | 0.82 min (HPLC-MS; method 5) |
| 51 | 5-iodo-thiophene-2-carboxylic acid-N-[(3-methyl-2,3,4,5-tetrahydro-1H-benzo[d]azepin-7-ylcarbamoyl)-methyl]-amide | 29% | $(M + H)^+ =$ 470 | 0.89 min (HPLC-MS; method 5) |

Example 52

3-[(5-chloro-thiophen-2-yl)carbonylamino]-N-(3-methyl-2,3,4,5-tetrahydro-1H-benzo[d]azepin-7-yl)-1-oxo-tetrahydro-thiophene-3-carboxylic acid amide

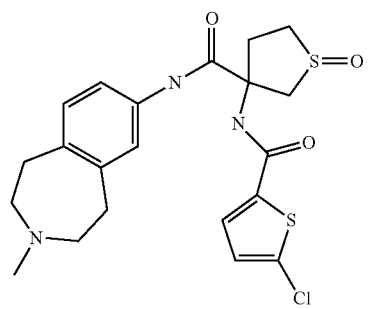 [SMILES: CN1CCc2ccc(NC(=O)C3(NC(=O)c4ccc(Cl)s4)CCS(=O)C3)cc2CC1]

90 mg (0.16 mmol) 3-[(5-chloro-thiophen-2-yl)-carbonylamino]-N-(3-methyl-2,3,4,5-tetrahydro-1H-benzo[d]azepin-7-yl)-tetrahydrothiophene-3-carboxylic acid amide (Ex. 20) are dissolved in 3.4 ml dichloromethane and 0.34 ml glacial acetic acid and 39.3 mg (0.16 mmol) 3-chloroperoxybenzoic acid are added at −5° C. Then the mixture is stirred for 1 h at 0° C., then heated to room temperature and stirred for 3 h. The reaction is washed with 5% sodium hydrogen carbonate solution and the organic phase is dried with sodium sulphate and concentrated by evaporation. The crude product is purified with RP material (Zorbax Stable-Bond C18; 3.5 μm; 4.6×75 mm eluant: water/acetonitrile/formic acid=95:5:0.1=>10:90:0.1).

Yield: 14.6 mg (18%)

$R_f$ value: 0.25 (silica gel; dichloromethane/ethanol/ammonia=8:2:0.2)

$C_{21}H_{24}ClN_3O_3S_2$ (466.02)

Mass spectrum: $(M+H)^+=466/468$ (chlorine isotopes)

Example 53

3-[(5-chloro-thiophen-2-yl)carbonylamino]-N-(3-methyl-2,3,4,5-tetrahydro-1H-benzo[d]azepin-7-yl)-1,1-dioxo-tetrahydro-thiophene-3-carboxylic acid amide

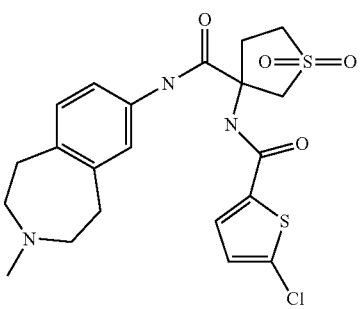

was isolated as a by-product in the preparation of Example 52.

Yield: 1.8 mg (2%)

$R_f$ value: 0.11 (silica gel; dichloromethane/ethanol/ammonia=8:2:0.2)

$C_{21}H_{24}ClN_3O_4S_2$ (482.02)

Mass spectrum: $(M+H)^+=482/484$ (chlorine isotopes)

Example 54

3-[(5-chloro-thiophen-2-yl)-carbonylamino]-N-(3-methyl-2,3,4,5-tetrahydro-1H-benzo[d]azepin-7-yl)-pyrrolidin-1-tert.butoxycarbonyl-3-carboxylic acid amide

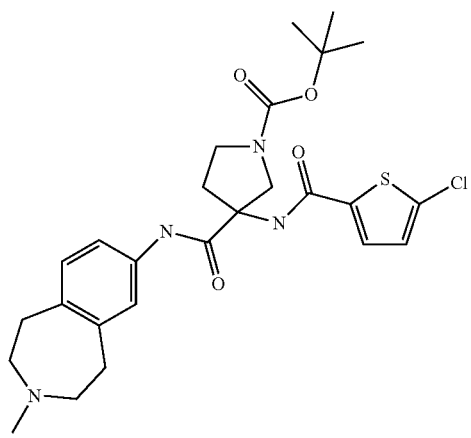 [SMILES: CN1CCc2ccc(NC(=O)C3(NC(=O)c4ccc(Cl)s4)CCN(C(=O)OC(C)(C)C)C3)cc2CC1]

The title compound was prepared analogously to the synthesis sequence in Example 1e/1f from 3-amino-pyrrolidin-1-tert.butoxycarbonyl-3-carboxylic acid, 5-chlorothiophene-2-carboxylic acid chloride and 3-methyl-2,3,4,5-tetrahydro-1H-benzo[d]azepin-7-ylamine.

Yield: 15.5 mg
$R_f$ value: 0.34 (RP-8; methanol/5% NaCl solution=6:4)
$C_{26}H_{33}ClN_4O_4S$ (533.09)
Mass spectrum: $(M+H)^+$=533/535 (chlorine isotopes)

Example 55

3-[(5-chloro-thiophen-2-yl)-carbonylamino]-N-(3-methyl-2,3,4,5-tetrahydro-1H-benzo[d]azepin-7-yl)-pyrrolidin-3-carboxylic acid amide

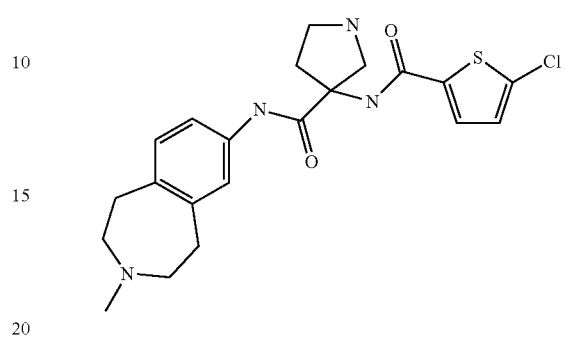

10 mg (0.02 mmol) 3-[(5-chloro-thiophen-2-yl)-carbonylamino]-N-(3-methyl-2,3,4,5-tetrahydro-1H-benzo[d]azepin-7-yl)-pyrrolidin-1-tert.butoxycarbonyl-3-carboxylic acid amide are dissolved in 0.25 ml THF and at room temperature 0.3 ml of 6 molar hydrochloric acid are added and the mixture is stirred for 1 h.

Then it is concentrated by evaporation i.vac.
Yield: 10 mg (80%)
$R_f$ value: 0.44 (RP-8; methanol/5% NaCl solution=6:4)
$C_{21}H_{25}ClN_4O_2S$ (432.98)
Mass spectrum: $(M+H)^+$=433/435 (chlorine isotopes)

The following compounds may be prepared from amino acid derivatives, benzazepine derivatives and thiophenecarboxylic acid derivatives analogously to the methods of synthesis described in the foregoing Examples or known from the literature:

| No. | Structural formula / Name | Yield Last Step | Mass peak(s) | $R_f$ value or $R_t$ |
|---|---|---|---|---|
| 56 | 4-[(5-chloro-thiophen-2-yl)-carbonylamino]-N-(3-methyl-2,3,4,5-tetrahydro-1H-benzo[d]azepin-7-yl)-tetrahydro-pyran-4-carboxylic acid amide | 68% | $(M + H)^+$ = 448/450 (chlorine isotopes) | 2.7 min (HPLC-MS; method 4) |
| 57 | 5-chloro-thiophene-2-carboxylic acid-N-[1-ethyl-1-(3-methyl-2,3,4,5-tetrahydro-1H-benzo[d]azepin-7-ylcarbamoyl)-propyl]-amide | 25% | $(M + H)^+$ = 434/436 (chlorine isotopes) | 0.31 (RP-8; methanol/ 5% NaCl solution = 6:4) |

| No. | Structural formula | Name | Yield Last Step | Mass peak(s) | $R_f$ value or $R_t$ |
|---|---|---|---|---|---|
| 59 | | 5-chloro-thiophene-2-carboxylic acid-N-[1-(3-methyl-2,3,4,5-tetrahydro-1H-benzo[d]azepin-7-ylcarbamoyl)-1-(prop-2-ynyl)-but-3-ynyl]-amide | 45% | $(M + H)^+$ = 454/456 (chlorine isotopes) | 0.3 (silica gel; dichloromethane/ethanol/glacial acetic acid = 90:10:1) |

Example 58

5-chloro-thiophene-2-carboxylic acid-N-[2-methoxy-1-methoxymethyl-1-(3-methyl-2,3,4,5-tetrahydro-1H-benzo[d]azepin-7-ylcarbamoyl)-ethyl]-amide

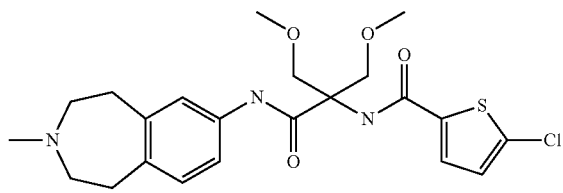 [SMILES: COCC(COC)(NC(=O)c1ccc(Cl)s1)C(=O)Nc1ccc2c(c1)CCN(C)CC2]

(a) 5-chloro-thiophene-2-carboxylic acid(1-hydroxymethyl-2-methoxy-1-methoxymethyl-ethyl)-amide 1.14 g (6.16 mmol) 2-amino-3-methoxy-2-methoxymethyl-propan-1-ol are suspended in 9 ml THF, cooled in the ice bath and combined with 2.56 ml (18.4 mmol) TEA. 1.12 g (6.19 mmol) 5-chlorothiophene-2-carboxylic acid chloride are dissolved in 6 ml THF and added dropwise. After 1.5 h the mixture is filtered and the filtrate is concentrated by evaporation i.vac. Then it is purified by chromatography through RP material (Microsorb C18 Varian; eluant: water/acetonitrile/trifluoroacetic acid=90:10:0.1=>0:100:0.1).

Yield: 0.20 g (8%)

$R_t$ value: 4.25 min (HPLC-MS method 3)

$C_{11}H_{16}ClNO_4S$ (293.77)

Mass spectrum: $(M+H)^+$=294/296 (chlorine isotopes)

(b) 2-[(5-chloro-thiophene-2-carbonyl)-amino]-3-methoxy-2-methoxymethyl-propionic acid 0.20 g (0.49 mmol) 5-chloro-thiophene-2-carboxylic acid (1-hydroxymethyl-2-methoxy-1-methoxymethyl-ethyl)-amide are dissolved at room temperature in 3 ml of water/3 ml acetonitrile and combined with 0.08 g (0.51 mmol) 2,2,6,6-tetramethyl-1-piperidinyloxy radical (TEMPO) and 0.13 g (1.55 mmol) sodium hydrogen carbonate. Then 1.5 ml (3.14 mmol) of 13% sodium hypochlorite is added dropwise and the mixture is stirred for 2 h. The reaction mixture is concentrated by evaporation i.vac. And purified by chromatography through RP material (Microsorb C18 Varian; eluant: water/acetonitrile/trifluoroacetic acid=90:10:0.1=>0:100:0.1).

Yield: 0.10 g (66%)

$R_t$ value: 4.16 min (HPLC-MS method 3)

$C_{11}H_{14}ClNO_5S$ (307.75)

Mass spectrum: $(M+H)^+$=306/308 (chlorine isotopes)

(c) 5-chloro-thiophene-2-carboxylic acid-N-[2-methoxy-1-methoxymethyl-1-(3-methyl-2,3,4,5-tetrahydro-1H-benzo[d]azepin-7-ylcarbamoyl)-ethyl]-amide 0.05 g (0.16 mmol) 2-[(5-chloro-thiophene-2-carbonyl)-amino]-3-methoxy-2-methoxymethyl-propionic acid are dissolved in 1.5 ml THF and at room temperature 0.04 g (0.16 mmol) 2-ethoxy-1-ethoxycarbonyl-1,2-dihydroquinoline (EEDQ) are added. After 30 min, 0.029 g (0.16 mmol) of 3-methyl-2,3,4,5-tetrahydro-1H-benzo[d]azepin-7-ylamine is added and the mixture is stirred for 12 h at 40° C. Then it is concentrated by evaporation i.vac. And purified by chromatography through RP material (Microsorb C18 Varian; eluant: water/acetonitrile/trifluoroacetic acid=90:10:0.1=>0:100:0.1).

Yield: 13.9 mg (15%)

$R_t$ value: 4.09 min (HPLC-MS method 3)

$C_{22}H_{28}ClN_3O_4S$ (466.00)

Mass spectrum: $(M+H)^+$=466/468 (chlorine isotopes)

Example 60

5-chloro-thiophene-2-carboxylic acid-N-[3-methoxy-1-methyl-1-(3-methyl-2,3,4,5-tetrahydro-1H-benzo[d]azepin-7-ylcarbamoyl)-propyl]-amide

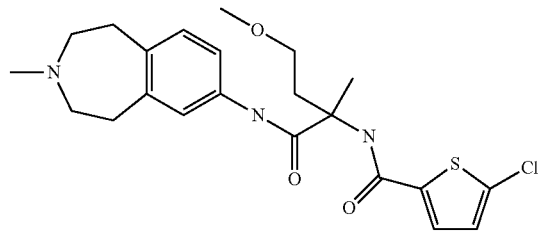 [SMILES: COCCC(C)(NC(=O)c1ccc(Cl)s1)C(=O)Nc1ccc2c(c1)CCN(C)CC2]

(a) ethyl 2-benzhydrilidenamino-4-methoxy-butanoate 15.0 g (56 mmol)N-(diphenylmethylene)glycinethylester are cooled to −78° C. in 150 ml THF, combined with 60 ml 1M NaHMDS solution and stirred for 1 h. Then 11 ml (117 mmol) 1-bromo-2-methoxyethane are added and the mixture is slowly heated to 5° C. After filtration the mixture is purified by repeated chromatography (silica gel, petroleum ether:ethyl acetate 9:1).
Yield: 8.1 g

(b) ethyl 2-benzhydrilidenamino-4-methoxy-2-methylbutanoate

Analogously to Example 60 (a) 2-benzhydrilidenamino-4-methoxy-butanoic acid is reacted with methyliodide to produce the title compound.
$C_{21}H_{25}NO_3$ (339.43)
Mass spectrum: $(M+H)^+=340$

(c) 5-chloro-thiophene-2-carboxylic acid-N-(1-ethoxycarbonyl-3-methoxy-1-methyl-propyl)-amide 0.57 g of ethyl 2-benzhydrilidenamino-4-methoxy-2-methylbutanoate in 2.5 ml THF are combined with 0.7 ml of 4M HCl and stirred for 2 h at room temperature. Then the mixture is combined with ethyl acetate and 1 M HCl. The aqueous phase is extracted three times with ethyl acetate and then freeze-dried. The crude product is reacted with 5-chlorothiophenecarboxylic acid chloride analogously to Example 1(e) to produce the title compound.
$C_{21}H_{25}NO_3$ (339.43)
Mass spectrum: $(M+H)^+=340$

(d) 5-chloro-thiophene-2-carboxylic acid-N-[3-methoxy-1-methyl-1-(3-methyl-2,3,4,5-tetrahydro-1H-benzo[d]azepin-7-ylcarbamoyl)-propyl]-amide 0.60 ml of a 2M solution of trimethylaluminium in toluene are added to a mixture of 130 mg (0.738 mmol) 3-methyl-2,3,4,5-tetrahydro-1H-benzo[d]azepin-7-ylamine in dichloromethane and stirred for 15 min. Then the mixture is added to 233 mg (0.729 mmol) 5-chloro-thiophene-2-carboxylic acid-N-(1-ethoxycarbonyl-3-methoxy-1-methylpropyl)-amide and stirred for 3 days. Then it is poured onto ice water/2 N NaOH, extracted several times with ethyl acetate and dried with sodium sulphate. The crude product is purified by chromatography.
$R_t$ value: 2.53 min (HPLC-MS method 2)
$C_{22}H_{28}ClN_3O_3S$ (450)
Mass spectrum: $(M+H)^+=450/452$ (chlorine isotopes)

Example 61

(R)-5-chloro-thiophene-2-carboxylic acid-N-[2-methoxy-1-methyl-1-(3-methyl-2,3,4,5-tetrahydro-1H-benzo[d]azepin-7-ylcarbamoyl)-ethyl]-amide

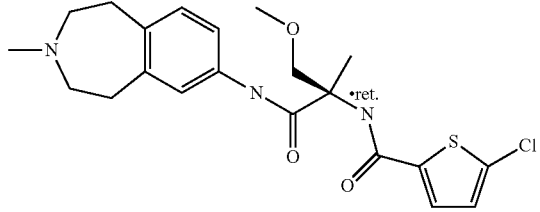 [SMILES: COC[C@@](C)(NC(=O)c1ccc(Cl)s1)C(=O)Nc1ccc2c(c1)CCN(C)CC2]

A mixture of 1.5 g (6.8 mmol)N-tert.butoxycarbonyl-α-methylserine in 100 ml acetonitrile is combined with in each case one-fifth of 7.8 g (34 mmol) of silver oxide and 4.3 ml (68 mmol) iodomethane, with vigorous stirring, at hourly intervals within 5 h and the mixture is stirred for 4 days. Then it is filtered and the crude product is reacted with 3-methyl-2,3,4,5-tetrahydro-1H-benzo[d]azepin-7-ylamine and 5-chlorothiophene-2-carboxylic acid chloride analogously to the reaction conditions described in Example if, 55 and 58a to obtain the title compound.
$R_f$ value: 0.63 (aluminium oxide; dichloromethane/ethanol=95:5)
$C_{21}H_{26}ClN_3O_3S$ (435.97)
Mass spectrum: $(M+H)^+=436/438$ (chlorine isotopes)

The following compounds may be prepared from amino acid derivatives, benzazepine derivatives and thiophenecarboxylic acid derivatives analogously to the methods of synthesis described in the foregoing Examples:

| No. | Structural formula | Name | Yield Last Step | Mass peak(s) | $R_f$ value or $R_t$ |
|---|---|---|---|---|---|
| 62 | | 5-chloro-thiophene-2-carboxylic acid-N-[2-benzyloxy-1-methyl-1-(3-methyl-2,3,4,5-tetrahydro-1H-benzo[d]azepin-7-ylcarbamoyl)-ethyl]-amide | 57% | $(M + H)^+ =$ 512/514 (chlorine isotopes) | Rt: 2.8 min HPLC-method 3a |

| No. | Structural formula Name | Yield Last Step | Mass peak(s) | $R_f$ value or $R_t$ |
|---|---|---|---|---|
| 63 | (R)-5-chloro-thiophene-2-carboxylic acid-N-[2-hydroxy-1-methyl-1-(3-methyl-2,3,4,5-tetrahydro-1H-benzo[d]azepin-7-ylcarbamoyl)-ethyl]-amide | 4% | $(M + H)^+ =$ 422/424 (chlorine isotopes) | 2.25 min (HPLC; method 2) |

Example 64

5-bromo-thiophene-2-carboxylic acid-N-[3-hydroxy-1-methyl-1-(3-methyl-2,3,4,5-tetrahydro-1H-benzo[d]azepin-7-ylcarbamoyl)-propyl]-amide

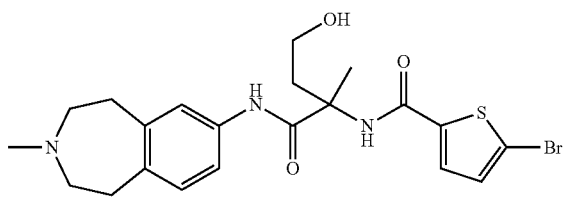 [SMILES: CN1CCc2ccc(NC(=O)C(C)(CCO)NC(=O)c3ccc(Br)s3)cc2CC1]

(a) methyl 2-[(5-bromo-thiophene-2-carbonyl)-amino]-propionate 5.18 g (25.30 mmol) 5-bromothiophene-2-carboxylic acid are stirred in 20 ml of thionyl chloride for 1 h at 60° C. and then the mixture is concentrated by evaporation i.vac.

3.52 g (25.26 mmol) DL-OMe-Ala-HCL are placed in 100 ml dichloromethane with 20 ml (142.25 mmol) TEA, then at 0° C. the acid chloride is added dropwise to 20 ml dichloromethane. At room temperature the mixture is stirred for 16 h and concentrated by evaporation i.vac. Then sodium hydrogen carbonate solution is added and the mixture is extracted 3× with ethyl acetate. The organic phase is washed 1× with 1 molar hydrochloric acid and 1× with sat. Sodium hydrogen carbonate solution and dried with sodium sulphate. Then it is concentrated by evaporation i.vac. And purified by chromatography through silica gel (eluant: ethyl acetate/petroleum ether 1:3=>1:2).

Yield: 6.0 g (82%)

$R_f$ value: 0.17 (silica gel; ethyl acetate/petroleum ether=30:70)

$C_9H_{10}BrNO_3S$ (292.15)

Mass spectrum: $(M+H)^+=290/292$ (bromine isotopes)

(b) 5-bromo-thiophene-2-carboxylic acid-N-(3-methyl-2-oxo-tetrahydro-furan-3-yl)-amide (prepared analogously to J. Org. Chem., 1993, 58, 6966)

1.90 ml (22.62 mmol) diisopropylamine and 5.00 ml (33.34 mmol) N,N,N,N-tetramethyl-ethylenediamine (TMEDA) are placed in 110 ml THF at 0° C. and slowly combined with 14.2 ml (22.62 mmol) 1.6 M n-butyllithium in n-hexane. Then the mixture is stirred for 20 min and cooled to −78° C., then 2.12 g (7.26 mmol) methyl 2-[(5-bromo-thiophene-2-carbonyl)-amino]-propionate in 50 ml THF are slowly added dropwise and the mixture is stirred for 1 h.

In a two-necked flask 4.0 ml (80.91 mmol) ethylene oxide are condensed at −78° C. and this is then added to the reaction mixture. The mixture is stirred for 20 h at room temperature. Then nitrogen is passed through the reaction vessel in order to expel excess ethylene oxide, then the reaction mixture is combined with aqueous ammonium chloride solution and concentrated by evaporation i.vac. The residue is combined with 1 M hydrochloric acid and THF and extracted with ethyl acetate. The organic phase is dried with sodium sulphate and purified by chromatography through RP material (eluant: water/acetonitrile 90:10=>0:100).

Yield: 0.20 g (9%)

$R_f$ value: 0.52 (silica gel; ethyl acetate/petroleum ether=30:10)

$C_{10}H_{10}BrNO_3S$ (304.16)

Mass spectrum: $(M+H)^+=304/306$ (bromine isotopes)

(c) 5-bromo-thiophene-2-carboxylic acid-N-[3-hydroxy-1-methyl-1-(3-methyl-2,3,4,5-tetrahydro-1H-benzo[d]azepin-7-ylcarbamoyl)-propyl]-amide 0.16 g (0.66 mmol) 3-methyl-2,3,4,5-tetrahydro-1H-benzo[d]azepine are suspended at room temperature in 3 ml dichloromethane, 1.30 ml (2.60 mmol) 2M trimethylaluminium solution in toluene are added dropwise thereto and the mixture is stirred for 30 min. 0.20 g (0.66 mmol) 5-bromo-thiophene-2-carboxylic acid (3-methyl-2-oxo-tetrahydro-furan-3-yl)-amide in 6 ml THF are added dropwise to the reaction mixture. It is then stirred for 20 h at room temperature. Then the reaction is poured onto 60 ml of 2 M sodium hydroxide solution and extracted 3× with ethyl acetate. The combined organic phases are dried with sodium sulphate and purified by chromatography through RP material (Microsorb C18 Varian eluant: water/acetonitrile 90:10=>0:100).

Yield: 0.14 g (38%)

$R_t$ value: 2.22 min (HPLC-MS; method 3a)

$C_{21}H_{26}BrN_3O_3S$ (480.43)

Mass spectrum: $(M+H)^+=480/482$ (bromine isotopes)

Example 65

5-chloro-thiophene-2-carboxylic acid-N-[1-methyl-3-dimethylaminocarbonyl-1-(3-methyl-2,3,4,5-tetrahydro-1H-benzo[d]azepin-7-ylcarbamoyl)-propyl]-amide

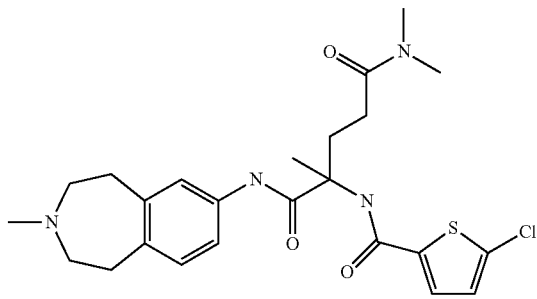 [SMILES: CN1CCc2ccc(NC(=O)C(C)(CCC(=O)N(C)C)NC(=O)c3ccc(Cl)s3)cc2CC1]

0.20 g (0.77 mmol) N-BOC-α-methyl-D,L-glutamic acid in 5 ml THF are combined with 0.24 g (0.77 mmol) TBTU and 0.10 ml (0.77 mmol) TEA with stirring at room temperature and stirred for 5 min. Then 0.38 ml (0.77 mmol) dimethylamine 2M in THF are and the mixture is stirred for 15 h at room temperature. The reaction mixture is concentrated by evaporation i.vac. And reacted analogously to the foregoing Examples to form the title compound.

$R_f$ value: 0.3 (silica gel; dichloromethane/ethanol/ammonia 80:20:2)

$C_{24}H_{31}ClN_4O_3S$ (491.05)

Mass spectrum: $(M+H)^+=491/493$ (chlorine isotopes)

The following compounds may be prepared from amino acid derivatives, benzazepine derivatives and thiophenecarboxylic acid derivatives analogously to the methods of synthesis described in the foregoing Examples:

| 66 | 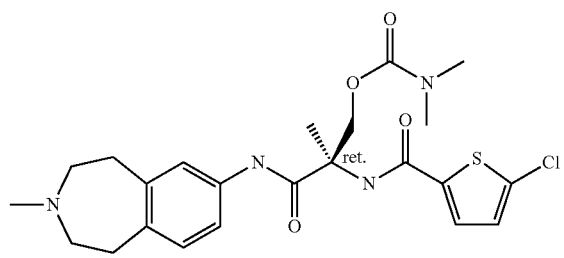 [SMILES: CN1CCc2ccc(NC(=O)[C@@](C)(COC(=O)N(C)C)NC(=O)c3ccc(Cl)s3)cc2CC1] | $(M + H)^+$ = 493/495 (chlorine isotopes) | Rt: 2.5 min HPLC-method 2 |
|---|---|---|---|

(R)-5-chloro-thiophene-2-carboxylic acid-N-[2-dimethylaminocarbonyloxy-1-methyl-1-(3-methyl-2,3,4,5-tetrahydro-1H-benzo[d]azepin-7-ylcarbamoyl)-ethyl]-amide

| 67 | 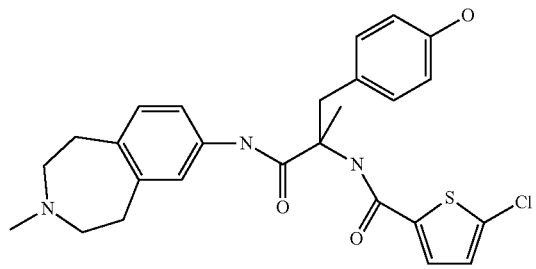 [SMILES: CN1CCc2ccc(NC(=O)C(C)(Cc3ccc(O)cc3)NC(=O)c3ccc(Cl)s3)cc2CC1] | $(M + H)^+$ = 498/500 (chlorine isotopes) | Rf: 0.48; silica gel; CH$_2$Cl$_2$/ethanol/ NH$_3$ = 80:20:2 |
|---|---|---|---|

5-chloro-thiophene-2-carboxylic acid-N-[2-(4-hydroxy-phenyl)-1-methyl-1-(3-methyl-2,3,4,5-tetrahydro-1H-benzo[d]azepin-7-ylcarbamoyl)-ethyl]-amide

| 68 | 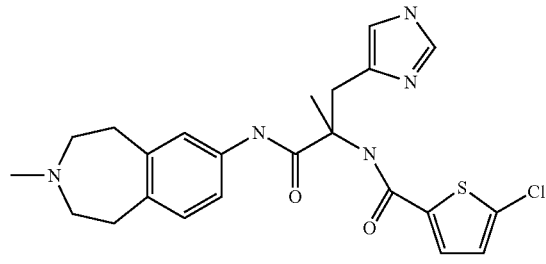 [SMILES: CN1CCc2ccc(NC(=O)C(C)(Cc3c[nH]cn3)NC(=O)c3ccc(Cl)s3)cc2CC1] | $(M + H)^+$ = 472/474 (chlorine isotopes) | Rf: 0.5; silica gel; CH$_2$Cl$_2$/ethanol = 80:20 |
|---|---|---|---|

5-chloro-thiophene-2-carboxylic acid-N-[2-(1H-imidazol-4-yl)-1-methyl-1-(3-methyl-2,3,4,5-tetrahydro-1H-benzo[d]azepin-7-ylcarbamoyl)-ethyl]-amide

Example 69

(R)-5-chloro-thiophene-2-carboxylic acid-N-[2-(3-methoxycarbonyl-propyloxy)-1-methyl-1-(3-methyl-2,3,4,5-tetrahydro-1H-benzo[d]azepin-7-ylcarbamoyl)-ethyl]-amide

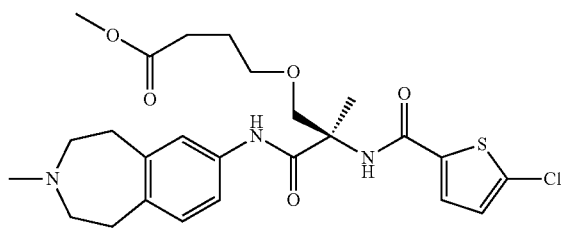 [SMILES: COC(=O)CCCOC[C@@](C)(NC(=O)c1ccc(Cl)s1)C(=O)Nc1ccc2c(c1)CCN(C)CC2]

(a) tert.butyl (R)—N-[2-(3-methoxycarbonyl-prop-2-enyloxy)-1-methyl-1-(3-methyl-2,3,4,5-tetrahydro-1H-benzo[d]azepin-7-ylcarbamoyl)-ethyl]-carbamate A mixture of 120 mg (0.226 mmol) tert.butyl (R)—N-[2-(prop-2-enyloxy)-1-methyl-1-(3-methyl-2,3,4,5-tetrahydro-1H-benzo[d]azepin-7-ylcarbamoyl)ethyl]-carbamate (prepared from (R)—O-allyl-α-methyl-N-butoxycarbonylserine and 3-methyl-2,3,4,5-tetrahydro-1H-benzo[d]azepin-7-ylamine) in methylene chloride is rinsed for 30 min with argon, combined with 0.42 ml (4.66 mmol) methyl acrylate and 2nd generation Grubbs catalyst and heated to boiling for 4 h. Then the mixture is concentrated by evaporation and purified by chromatography. $R_t$ value: 2.53 min (HPLC-MS; method 2)

(b) (R)-5-chloro-thiophene-2-carboxylic acid-N-[2-(3-methoxycarbonyl-propyloxy)-1-methyl-1-(3-methyl-2,3,4,5-tetrahydro-1H-benzo[d]azepin-7-ylcarbamoyl)-ethyl]-amide Tert.butyl (R)—N-[2-(3-methoxycarbonyl-prop-2-enyloxy)-1-methyl-1-(3-methyl-2,3,4,5-tetrahydro-1H-benzo[d]azepin-7-ylcarbamoyl)-ethyl]-carbamate is reacted by a 3-step synthesis sequence analogously to Example 1(c), 35 and 1(f) to form the title compound.
$R_t$ value: 1.79 min (method 6)
$C_{25}H_{32}ClN_3O_5S$ (522.06)
Mass spectrum: $(M+H)^+=522/524$ (chlorine isotopes)

Example 70

(R)-5-chloro-thiophene-2-carboxylic acid-N-[2-(3-hydroxycarbonyl-propyloxy)-1-methyl-1-(3-methyl-2,3,4,5-tetrahydro-1H-benzo[d]azepin-7-ylcarbamoyl)-ethyl]-amide

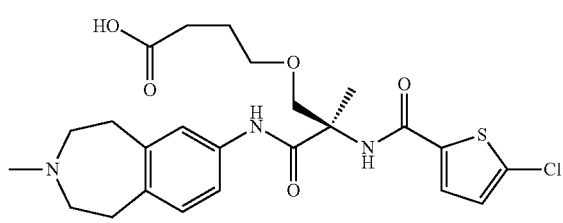 [SMILES: CN1CCc2ccc(NC(=O)[C@@](C)(COCCCC(=O)O)NC(=O)c3ccc(Cl)s3)cc2CC1]

is prepared from Example 69 by saponification with lithium hydroxide analogously to Example 8 (d).
$R_t$ value: 2.4 min (HPLC-MS; method 2)
$C_{24}H_{30}ClN_3O_5S$ (508.03)
Mass spectrum: $(M+H)^+=508/510$ (chlorine isotopes)

Example 71

5-chloro-thiophene-2-carboxylic acid-N-[1-methyl-1-(3,5-dimethyl-2,3,4,5-tetrahydro-1H-benzo[d]azepin-7-ylcarbamoyl)-ethyl]-amide

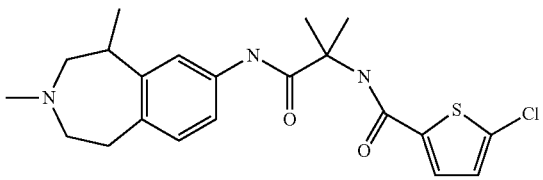 [SMILES: CC1CN(C)CCc2ccc(NC(=O)C(C)(C)NC(=O)c3ccc(Cl)s3)cc21]

(a) 3,5-dimethyl-2,3,4,5-tetrahydro-1H-benzo[d]azepin-7-ylamine and 35-dimethyl-2,3,4,5-tetrahydro-1H-benzo[d]azepin-8-ylamine Starting from 1-methyl-2,3,4,5-tetrahydro-1H-benzo[d]azepine a mixture of the two title compounds may be prepared by the synthesis sequence of Leuckart-Wallach reaction analogously to Example 1(b), nitrogenation analogously to Example 9(a) and reduction analogously to Example 9(d), and the mixture may be purified by chromatography (silica gel, methylene chloride/(ethanol: ammonia 95:5) 99/1→8/2):

3,5-dimethyl-2,3,4,5-tetrahydro-1H-benzo[d]azepin-7-ylamine $R_f$ value: 0.70 (silica gel; methylene chloride/methanol/ammonia 80/20/2)
$C_{12}H_{18}N_2$ (190.29)
Mass spectrum: $(M+H)^+=191$ 3,5-dimethyl-2,3,4,5-tetrahydro-1H-benzo[d]azepin-8-ylamine $R_f$ value: 0.75 (silica gel; methylene chloride/methanol/ammonia 80/20/2)
$C_{12}H_{18}N_2$ (190.29)
Mass spectrum: $(M+H)^+=191$ (b) 5-chloro-thiophene-2-carboxylic acid-N-[1-methyl-1-(3,5-dimethyl-2,3,4,5-tetrahydro-1H-benzo[d]azepin-7-ylcarbamoyl)-ethyl]-amide is prepared by reacting 3,5-dimethyl-2,3,4,5-tetrahydro-1H-benzo[d]azepin-7-ylamine analogously to Example 1(f).
$R_f$ value: 0.6 (silica gel; methylene chloride/methanol/ammonia 80/20/2)
$C_{21}H_{26}ClN_3O_2S$ (419.97)
Mass spectrum: $(M+H)^+=420/422$ (chlorine isotopes)

Example 72

5-chloro-thiophene-2-carboxylic acid-N-[1-methyl-1-(3,5-dimethyl-2,3,4,5-tetrahydro-1H-benzo[d]azepin-8-ylcarbamoyl)-ethyl]-amide

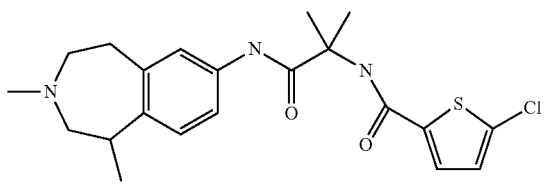 [SMILES: CC1CN(C)CCc2cc(NC(=O)C(C)(C)NC(=O)c3ccc(Cl)s3)ccc21]

is prepared from 3,5-dimethyl-2,3,4,5-tetrahydro-1H-benzo[d]azepin-8-ylamine (see Example 71a) analogously to Example 1(f).

$R_f$ value: 0.8 (silica gel; methylene chloride/methanol/ammonia 80/20/2)

$C_{21}H_{26}ClN_3O_2S$ (419.97)

Mass spectrum: $(M+H)^+$=420/422 (chlorine isotopes)

Example 73

5-chloro-thiophene-2-carboxylic acid-N-{1-methyl-1-[3-methyl-5-(4-aminophenyl)-2,3,4,5-tetrahydro-1H-benzo[d]azepin-7-ylcarbamoyl]-ethyl}-amide

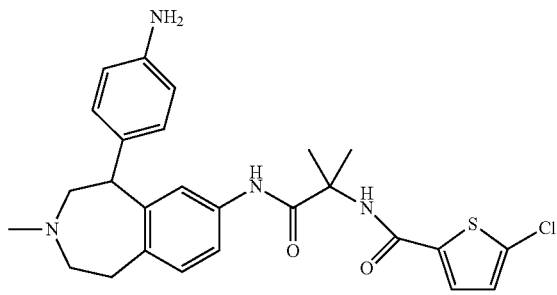 [SMILES: CN1CCc2ccc(NC(=O)C(C)(C)NC(=O)c3ccc(Cl)s3)cc2C(c2ccc(N)cc2)C1]

(a) 3-methyl-5-phenyl-2,3,4,5-tetrahydro-1H-benzo[d]azepine 1.00 g (4.48 mmol) 1-phenyl-2,3,4,5-tetrahydro-1H-benzo[d]azepine is taken up in 1.7 ml formic acid and combined with 1.22 ml of 37% formalin solution, then heated to 70° C. for 2 h. The reaction mixture is concentrated, made basic with 10 M NaOH and extracted with ethyl acetate. The organic phases are dried with sodium sulphate, then filtered and evaporated down.

$R_f$ value: 0.35 (silica gel; methylene chloride/methanol/ammonia 95/5/0.5)

$C_{17}H_{19}N$ (237.34)

Mass spectrum: $(M+H)^+$=238

(b) 3-methyl-5-(4-nitrophenyl)-7-nitro-2,3,4,5-tetrahydro-1H-benzo[d]azepine 3-methyl-5-phenyl-2,3,4,5-tetrahydro-1H-benzo[d]azepine is nitrogenated analogously to Example 9(a) and purified by chromatography (silica gel: petroleum ether/ethyl acetate 1/1→1/100)

$R_f$ value: 0.2 (silica gel; ethyl acetate)

$C_{17}H_{17}N_3O_4$ (327.33)

Mass spectrum: $(M+H)^+$=328

(c) 5-chloro-thiophene-2-carboxylic acid-N-{1-methyl-1-[3-methyl-5-(4-aminophenyl)-2,3,4,5-tetrahydro-1H-benzo[d]azepin-7-ylcarbamoyl]-ethyl}-amide is prepared by hydrogenation of 3-methyl-5-(4-nitrophenyl)-7-nitro-2,3,4,5-tetrahydro-1H-benzo[d]azepine analogously to Example 1(c) and subsequent reaction with 2-[(5-chloro-thiophen-2-yl)-carbonylamino]-2-methyl-propionic acid analogously to Example 1(f).

$R_f$ value: 0.6 (aluminium oxide; methylene chloride/ethanol 95/5)

$C_{26}H_{29}ClN_4O_2S$ (497.05)

Mass spectrum: $(M+H)^+$=497/499 (chlorine isotopes) The following compounds may be prepared from amino acid derivatives, benzazepine derivatives and thiophenecarboxylic acid derivatives analogously to the methods of synthesis described in the Examples or known from the literature:

| | | | |
|---|---|---|---|
| 74 | 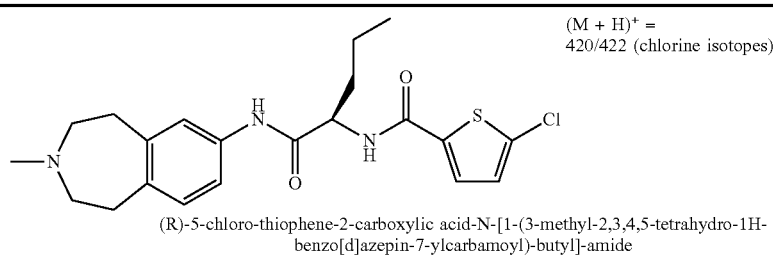 (R)-5-chloro-thiophene-2-carboxylic acid-N-[1-(3-methyl-2,3,4,5-tetrahydro-1H-benzo[d]azepin-7-ylcarbamoyl)-butyl]-amide | $(M + H)^+$ = 420/422 (chlorine isotopes) | Rt: 2.63 min HPLC-method 2 |
| 75 | 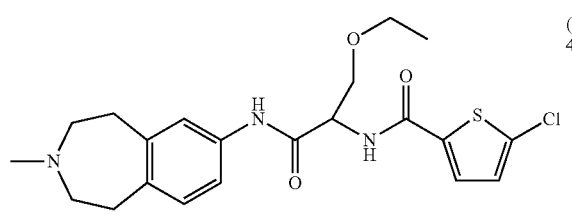 5-chloro-thiophene-2-carboxylic acid-N-[2-ethoxy-1-(3-methyl-2,3,4,5-tetrahydro-1H-benzo[d]azepin-7-ylcarbamoyl)-ethyl]-amide | $(M + H)^+$ = 436/438 (chlorine isotopes) | Rt: 2.56 min HPLC-method 2 |

| | | | |
|---|---|---|---|
| 76 | 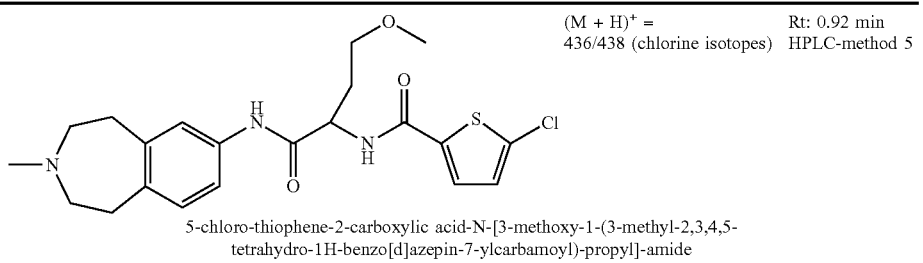  5-chloro-thiophene-2-carboxylic acid-N-[3-methoxy-1-(3-methyl-2,3,4,5-tetrahydro-1H-benzo[d]azepin-7-ylcarbamoyl)-propyl]-amide | (M + H)⁺ = 436/438 (chlorine isotopes) | Rt: 0.92 min HPLC-method 5 |
| 77 | 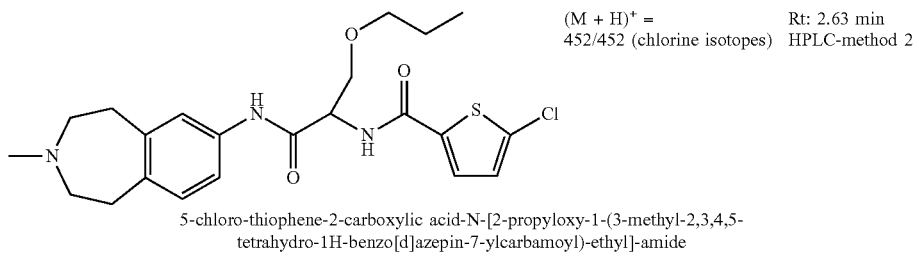  5-chloro-thiophene-2-carboxylic acid-N-[2-propyloxy-1-(3-methyl-2,3,4,5-tetrahydro-1H-benzo[d]azepin-7-ylcarbamoyl)-ethyl]-amide | (M + H)⁺ = 452/452 (chlorine isotopes) | Rt: 2.63 min HPLC-method 2 |
| 78 | 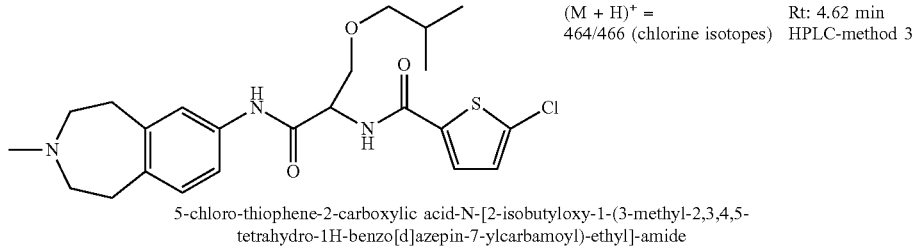  5-chloro-thiophene-2-carboxylic acid-N-[2-isobutyloxy-1-(3-methyl-2,3,4,5-tetrahydro-1H-benzo[d]azepin-7-ylcarbamoyl)-ethyl]-amide | (M + H)⁺ = 464/466 (chlorine isotopes) | Rt: 4.62 min HPLC-method 3 |
| 79 | 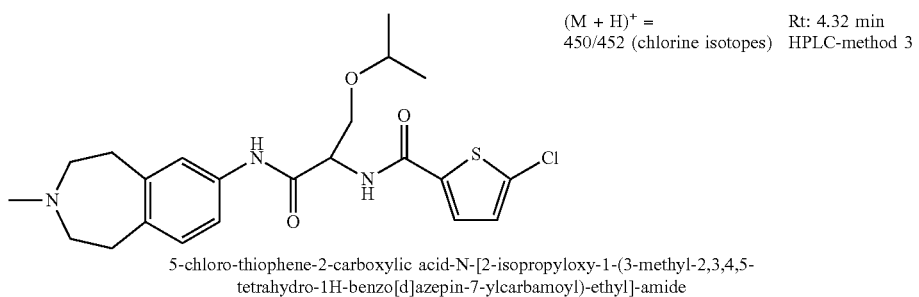  5-chloro-thiophene-2-carboxylic acid-N-[2-isopropyloxy-1-(3-methyl-2,3,4,5-tetrahydro-1H-benzo[d]azepin-7-ylcarbamoyl)-ethyl]-amide | (M + H)⁺ = 450/452 (chlorine isotopes) | Rt: 4.32 min HPLC-method 3 |
| 80 | 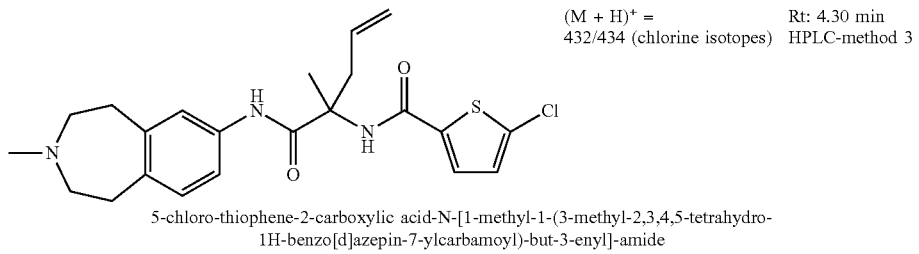  5-chloro-thiophene-2-carboxylic acid-N-[1-methyl-1-(3-methyl-2,3,4,5-tetrahydro-1H-benzo[d]azepin-7-ylcarbamoyl)-but-3-enyl]-amide | (M + H)⁺ = 432/434 (chlorine isotopes) | Rt: 4.30 min HPLC-method 3 |
| 81 | 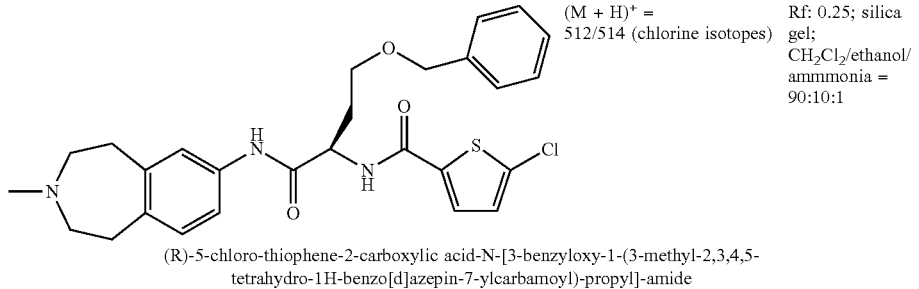  (R)-5-chloro-thiophene-2-carboxylic acid-N-[3-benzyloxy-1-(3-methyl-2,3,4,5-tetrahydro-1H-benzo[d]azepin-7-ylcarbamoyl)-propyl]-amide | (M + H)⁺ = 512/514 (chlorine isotopes) | Rf: 0.25; silica gel; CH₂Cl₂/ethanol/ ammmonia = 90:10:1 |

| 82 | 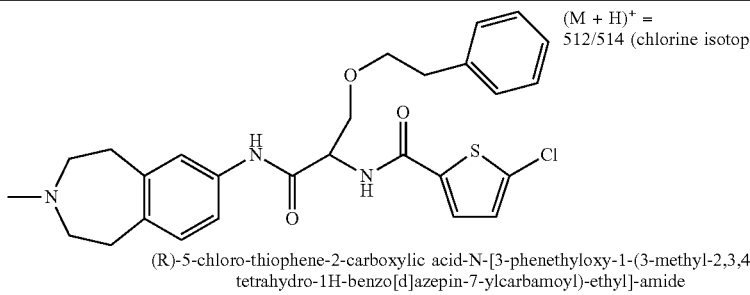 | (M + H)⁺ = 512/514 (chlorine isotopes) | Rt: 4.82 min HPLC-method 3 |

(R)-5-chloro-thiophene-2-carboxylic acid-N-[3-phenethyloxy-1-(3-methyl-2,3,4,5-tetrahydro-1H-benzo[d]azepin-7-ylcarbamoyl)-ethyl]-amide

Example 83

5-chloro-thiophene-2-carboxylic acid-N-[2-(2-methoxyethyloxy)-1-(3-methyl-2,3,4,5-tetrahydro-1H-benzo[d]azepin-7-ylcarbamoyl)-ethyl]-amide

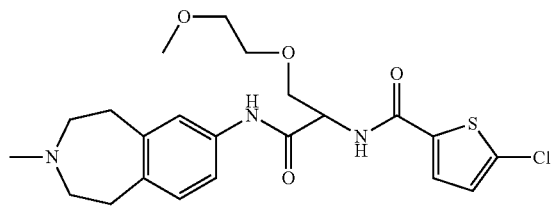 [SMILES: COCCOCC(NC(=O)c1ccc(Cl)s1)C(=O)Nc1ccc2c(c1)CCN(C)CC2]

(a) methyl N-(5-chlorothiophen-2-yl)carbonyl-aziridine-2-carboxylate

A mixture of 4.40 g (43.5 mmol) methyl aziridine-2-carboxylate and 13.5 ml (97.3 mmol) triethylamine in 30 ml methylene chloride is combined with 8.80 g (48.6 mmol) 5-chlorothiophenecarboxylic acid chloride in 30 ml methylene chloride while cooling with ice and subsequently after removal of the cooling bath stirred for 3 h at room temperature. Then the mixture is diluted with water, extracted with methylene chloride, dried with sodium sulphate, concentrated and purified by chromatography (silica gel, petroleum ether/ethyl acetate 80/15→80/20) to obtain the slightly contaminated title compound.

$R_f$ value: 0.42 (silica gel; methylene chloride/methanol 80/20)

$C_9H_8ClNO_3S$ (245.68)

Mass spectrum: (M+H)⁺=246/248 (chlorine isotopes)

(b) methyl 2-(5-chlorothiophen-2-yl)carbonylamino-3-(2-methoxyethyloxy)propionate A mixture of 0.30 g (about 1 mmol) methyl N-(5-chlorothiophen-2-yl)carbonyl-aziridine-2-carboxylate and 0.29 ml (3.7 mmol) 2-methoxyethanol in 4 ml methylene chloride is slowly combined with 0.16 ml boron trifluoride etherate and stirred for 3 h. The reaction mixture is concentrated and purified by chromatography (silica gel, petroleum ether/ethyl acetate 80/20→40/60).

$R_f$ value: 0.05 (silica gel; methylene chloride/methanol 80/20)

$C_{12}H_{16}ClNO_5S$ (321.78)

Mass spectrum: (M+H)⁺=322/324 (chlorine isotopes)

(c) 5-chloro-thiophene-2-carboxylic acid-N-[2-(2-methoxyethyloxy)-1-(3-methyl-2,3,4,5-tetrahydro-1H-benzo[d]azepin-7-ylcarbamoyl)-ethyl]-amide The title compound is prepared from methyl 2-(5-chlorothiophen-2yl)carbonylamino-3-(2-methoxyethyloxy)propionate by lithium hydroxide saponification and subsequent reaction with 3-methyl-2,3,4,5-tetrahydro-1H-benzo[d]azepin-7-ylamine with EEDQ analogously to Example 58(c).

$R_f$ value: 3.98 min (method 3)

$C_{22}H_{28}ClN_3O_4S$ (465.99)

Mass spectrum: (M+H)⁺=466/468 (chlorine isotopes)

Example 84 and 85

1-[(5-chloro-thiophen-2-yl)-carbonylamino]-3,4-dihydroxy-N-(3-methyl-2,3,4,5-tetrahydro-1H-benzo[d]azepin-7-yl)-cyclopentane-1-carboxylic acid amide (84) and 1-[(5-chloro-thiophen-2-yl)-carbonylamino]-3-formyloxy-4-hydroxy-N-(3-methyl-2,3,4,5-tetrahydro-1H-benzo[d]azepin-7-yl)-cyclopentane-1-carboxylic acid amide (85)

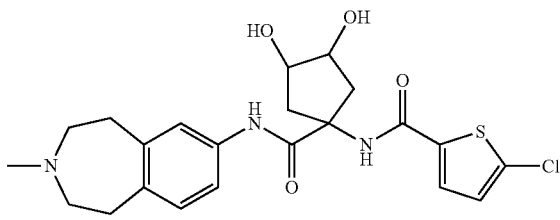

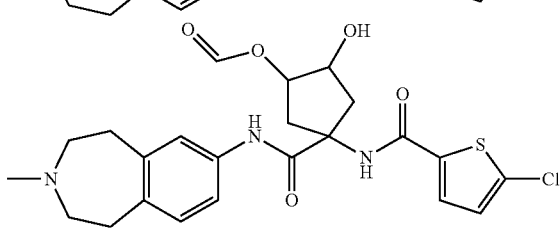

A mixture of 0.10 g (0.348 mmol) 1-[(5-chloro-thiophen-2-yl)-carbonylamino]-3,4-epoxy-cyclopentane-1-carboxylic acid, 0.113 g (0.352 mmol) TBTU and 0.116 ml (1.055 mmol) NMM in 1.5 ml DMF is stirred for 30 min and then combined with 62 mg (0.352 mmol) 3-methyl-2,3,4,5-tetrahydro-1H-benzo[d]azepin-7-ylamine and stirred overnight. Water is added, the mixture is extracted with ethyl acetate, concentrated and the residue is taken up in DMF and trifluoroacetic acid and purified by chromatography by HPLC.

Example 84

$R_t$ value: 3.53 min (method 3)
$C_{22}H_{26}ClN_3O_4S$ (463.98)
Mass spectrum: (M+H)$^+$=464/466 (chlorine isotopes)

Example 85

$R_t$ value: 3.72 min (method 3)
$C_{23}H_{26}ClN_3O_5S$ (491.99)
Mass spectrum: (M+H)$^+$=492/494 (chlorine isotopes)

Example 86

1-[(5-chloro-thiophen-2-yl)-carbonylamino]-3,4-dimethoxy-N-(3-methyl-2,3,4,5-tetrahydro-1H-benzo[d]azepin-7-yl)-cyclopentane-1-carboxylic acid amide

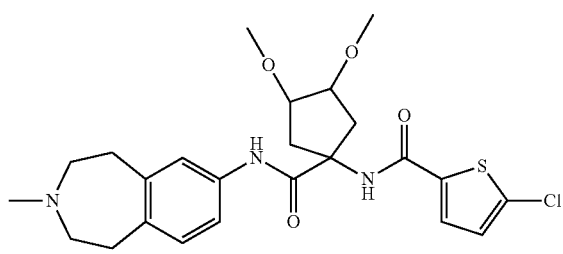 [SMILES: COC1CC(NC(=O)c2ccc(Cl)s2)(C(=O)Nc2ccc3c(c2)CCN(C)CC3)CC1OC]

(a) methyl 1-[(5-chloro-thiophen-2-yl)-carbonylamino]-3,4-epoxy-cyclopentane-1-carboxylate A mixture of 0.85 g (2.9 mmol) methyl 1-[(5-chloro-thiophen-2-yl)-carbonylamino]-cyclopent-3-ene-1-carboxylate and 20 ml methylene chloride is combined with 0.92 g 70% meta-chloroperbenzoic acid at 0° C. and stirred for 3 h at room temperature. The mixture is washed with sat. Sodium hydrogen carbonate solution and concentrated.

$C_{12}H_{12}ClNO_4S$ (301.75)
Mass spectrum: (M+H)$^+$=302/304 (chlorine isotopes)

(b) methyl 1-[(5-chloro-thiophen-2-yl)-carbonylamino]-3,4-dihydroxy-cyclopentane-1-carboxylate A mixture of 0.76 g (1.84 mmol) methyl 1-[(5-chloro-thiophen-2-yl)-carbonylamino]-3,4-epoxy-cyclopentane-1-carboxylate, 3.0 ml acetic acid and 0.38 g potassium hydrogen sulphate are stirred for 4 h at 40° C. Then the mixture is concentrated by evaporation, dissolved in DMF, acidified with trifluoroacetic acid and purified by preparative HPLC.

$C_{12}H_{14}ClNO_5S$ (319.76)
Mass spectrum: (M+H)$^+$=320/322 (chlorine isotopes)

(c) 1-[(5-chloro-thiophen-2-yl)-carbonylamino]-3,4-dimethoxy-N-(3-methyl-2,3,4,5-tetrahydro-1H-benzo[d]azepin-7-yl)-cyclopentane-1-carboxylic acid amide The title compound was prepared from methyl 1-[(5-chloro-thiophen-2-yl)-carbonylamino]-3,4-dihydroxy-cyclopentane-1-carboxylate by methylation analogously to Example 61 and subsequent saponification with LiOH and reaction with 3-methyl-2,3,4,5-tetrahydro-1H-benzo[d]azepin-7-ylamine.

$R_t$ value: 4.09 min (HPLC-MS; method 3)
$C_{24}H_{30}ClN_3O_4S$ (492.04)
Mass spectrum: (M+H)$^+$=492/494 (chlorine isotopes)

Example 87

(R)-5-bromo-thiophene-2-carboxylic acid-N-[2-(5-methyl-oxazol-2-yl)-1-(3-methyl-2,3,4,5-tetrahydro-1H-benzo[d]azepin-7-ylcarbamoyl)-ethyl]-amide

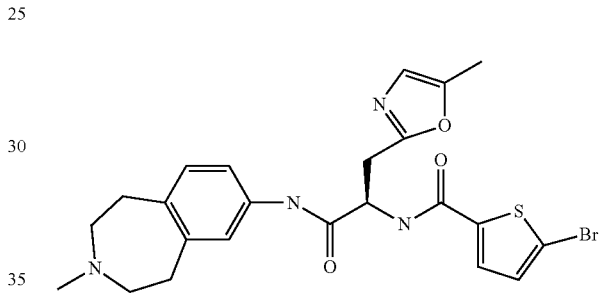

A mixture of 0.70 g (2.5 mmol) methyl (R)-2-tert.butoxycarbonylamino-3-propargylaminocarbonyl-propionate, 10 mg gold trichloride and 9.0 ml acetonitrile is stirred for 16 h at 50° C. Then the mixture is filtered, concentrated by evaporation and purified by HPLC. The crude product is reacted analogously to Example 64(c) with methyl-2,3,4,5-tetrahydro-1H-benzo[d]azepin-7-ylamine, then subjected to BOC cleaving and reaction with 5-bromothiophenecarboxylic acid analogously to Example 1(f) to form the title compound.

$R_t$ value: 2.52 min (HPLC-MS; method 2)
$C_{23}H_{25}BrN_4O_3S$ (517.45)
Mass spectrum: (M+H)$^+$=517/519 (bromine isotopes)

The following compounds may be prepared from amino acid derivatives, benzazepine derivatives and thiophenecarboxylic acid derivatives analogously to the methods of synthesis described in the Examples or known from the literature:

| 88 | 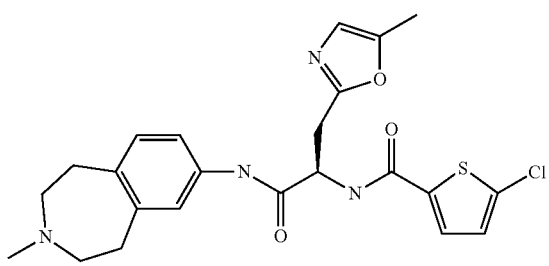 [SMILES: Cc1cnc(C[C@@H](NC(=O)c2ccc(Cl)s2)C(=O)Nc2ccc3c(c2)CCN(C)CC3)o1] | (M + H)$^+$ = 473/475 (chlorine isotopes) | Rt: 2.48 min HPLC-method 2 |

(R)-5-chloro-thiophene-2-carboxylic acid-N-[2-(5-methyl-oxazol-2-yl)-1-(3-methyl-2,3,4,5-tetrahydro-1H-benzo[d]azepin-7-ylcarbamoyl)-ethyl]-amide

| | | | |
|---|---|---|---|
| 89 | 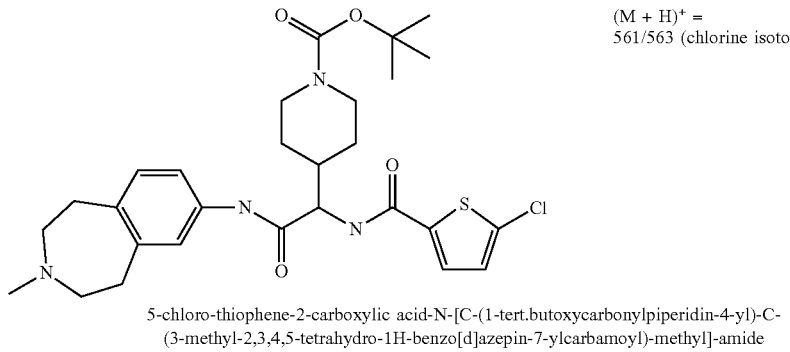 5-chloro-thiophene-2-carboxylic acid-N-[C-(1-tert.butoxycarbonylpiperidin-4-yl)-C-(3-methyl-2,3,4,5-tetrahydro-1H-benzo[d]azepin-7-ylcarbamoyl)-methyl]-amide | (M + H)$^+$ = 561/563 (chlorine isotopes) | Rf: 0.37; silica gel; CH$_2$Cl$_2$/ethanol/ ammonia = 90:10:1 |
| 90 | 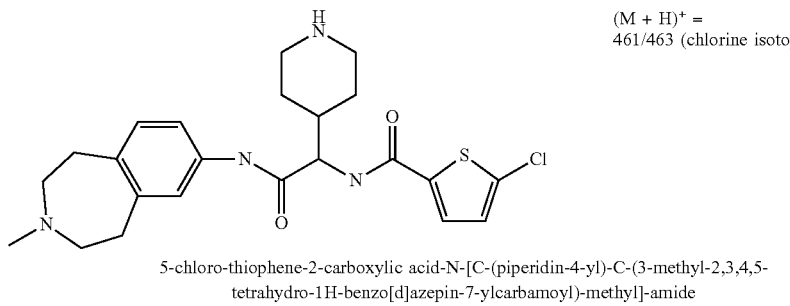 5-chloro-thiophene-2-carboxylic acid-N-[C-(piperidin-4-yl)-C-(3-methyl-2,3,4,5-tetrahydro-1H-benzo[d]azepin-7-ylcarbamoyl)-methyl]-amide | (M + H)$^+$ = 461/463 (chlorine isotopes) | Rf: 0.42; RP8; MeOH/5% NaCl solution = 6/4 |
| 91 | 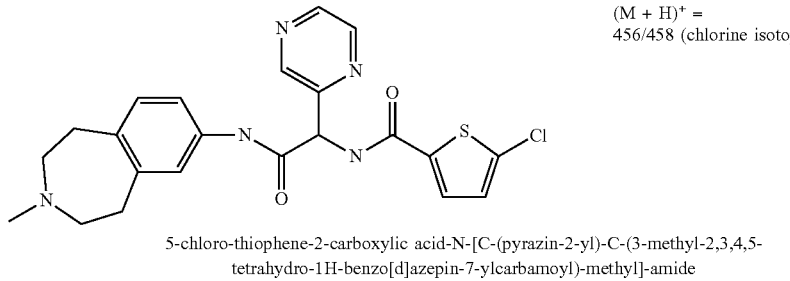 5-chloro-thiophene-2-carboxylic acid-N-[C-(pyrazin-2-yl)-C-(3-methyl-2,3,4,5-tetrahydro-1H-benzo[d]azepin-7-ylcarbamoyl)-methyl]-amide | (M + H)$^+$ = 456/458 (chlorine isotopes) | Rf: 0.35; RP8; MeOH/5% NaCl solution = 6/4 |
| 92 | 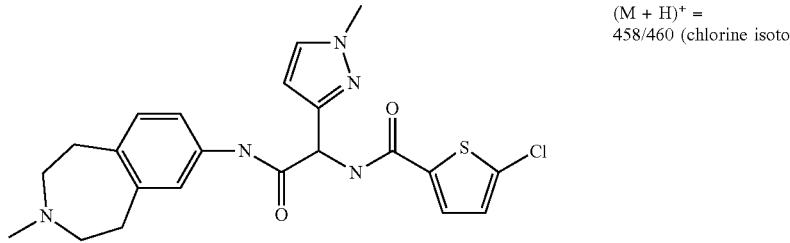 5-chloro-thiophene-2-carboxylic acid-N-[C-(1-methyl-pyrazol-3-yl)-C-(3-methyl-2,3,4,5-tetrahydro-1H-benzo[d]azepin-7-ylcarbamoyl)-methyl]-amide | (M + H)$^+$ = 458/460 (chlorine isotopes) | Rf: 0.6; silica gel; CH$_2$Cl$_2$/ethanol/ ammonia = 80:20:2 |
| 93 | 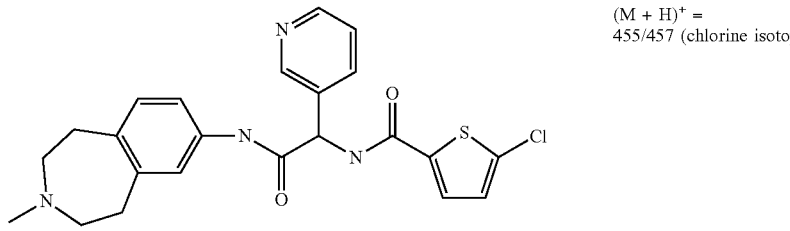 5-chloro-thiophene-2-carboxylic acid-N-[C-(pyridin-3-yl)-C-(3-methyl-2,3,4,5-tetrahydro-1H-benzo[d]azepin-7-ylcarbamoyl)-methyl]-amide | (M + H)$^+$ = 455/457 (chlorine isotopes) | Rf: 0.54; Alox; CH$_2$Cl$_2$/ethanol = 95/5 |

| | | | |
|---|---|---|---|
| 94 | 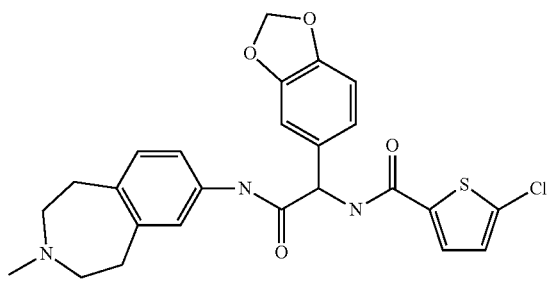 [SMILES: CN1CCc2ccc(NC(=O)C(NC(=O)c3ccc(Cl)s3)c3ccc4c(c3)OCO4)cc2CC1]

5-chloro-thiophene-2-carboxylic acid-N-[C-(3,4-methylenedioxophenyl)-C-(3-methyl-2,3,4,5-tetrahydro-1H-benzo[d]azepin-7-ylcarbamoyl)-methyl]-amide | (M + H)⁺ = 498/500 (chlorine isotopes) | Rf: 0.75; silica gel; CH$_2$Cl$_2$/ethanol/ammonia = 80:20:2 |
| 95 | 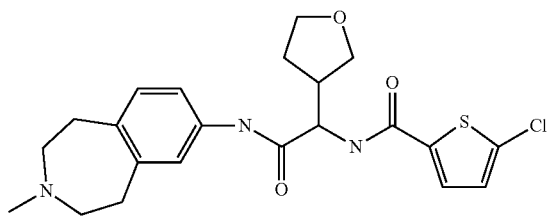 [SMILES: CN1CCc2ccc(NC(=O)C(NC(=O)c3ccc(Cl)s3)C3CCOC3)cc2CC1]

5-chloro-thiophene-2-carboxylic acid-N-[C-(tetrahydrofuran-3-yl)-C-(3-methyl-2,3,4,5-tetrahydro-1H-benzo[d]azepin-7-ylcarbamoyl)-methyl]-amide | (M + H)⁺ = 448/450 (chlorine isotopes) | Rt: 2.72 min HPLC-method 4 |
| 96 | 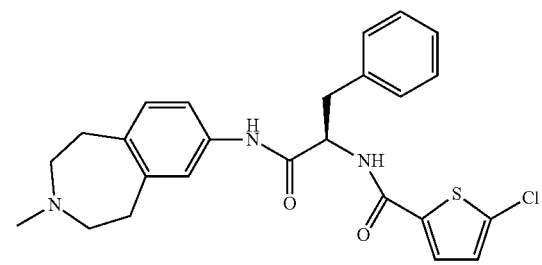 [SMILES: CN1CCc2ccc(NC(=O)[C@@H](Cc3ccccc3)NC(=O)c3ccc(Cl)s3)cc2CC1]

(R)-5-chloro-thiophene-2-carboxylic acid-N-[2-phenyl-1-(3-methyl-2,3,4,5-tetrahydro-1H-benzo[d]azepin-7-ylcarbamoyl)-ethyl]-amide | (M + H)⁺ = 468/470 (chlorine isotopes) | Rf: 0.79; Alox; CH$_2$Cl$_2$/ethanol = 95/5 |
| 97 | 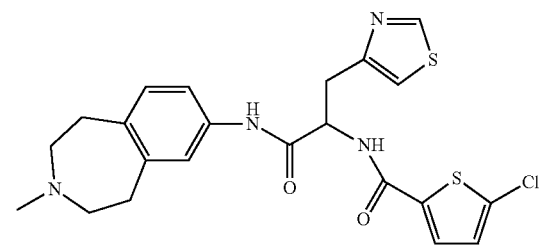 [SMILES: CN1CCc2ccc(NC(=O)C(Cc3cscn3)NC(=O)c3ccc(Cl)s3)cc2CC1]

5-chloro-thiophene-2-carboxylic acid-N-[2-(thiazol-4-yl)-1-(3-methyl-2,3,4,5-tetrahydro-1H-benzo[d]azepin-7-ylcarbamoyl)-ethyl]-amide | (M + H)⁺ = 475/477 (chlorine isotopes) | Rf: 0.56; Alox; CH$_2$Cl$_2$/ethanol = 95/5 |
| 98 | 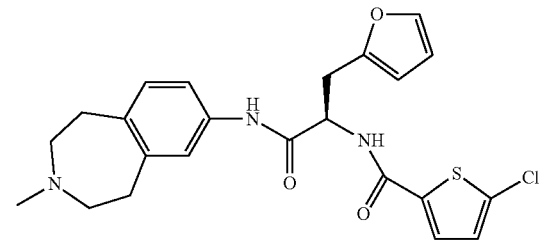 [SMILES: CN1CCc2ccc(NC(=O)[C@@H](Cc3ccco3)NC(=O)c3ccc(Cl)s3)cc2CC1]

(R)-5-chloro-thiophene-2-carboxylic acid-N-[2-(furan-2-yl)-1-(3-meethyl-2,3,4,5-tetrahydro-1H-benzo[d]azepin-7-ylcarbamoyl)-ethyl]-amide | (M + H)⁺ = 458/460 (chlorine isotopes) | Rf: 0.77; Alox; CH$_2$Cl$_2$/ethanol = 95/5 |

| | | | |
|---|---|---|---|
| 99 | 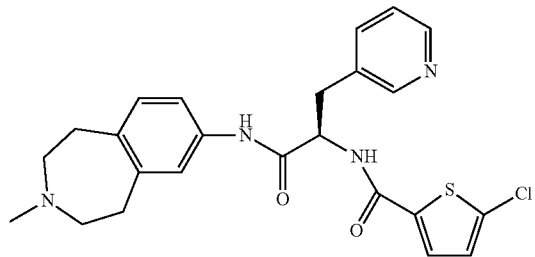 [SMILES: CN1CCc2ccc(NC(=O)[C@@H](Cc3cccnc3)NC(=O)c3ccc(Cl)s3)cc2CC1]<br>(R)-5-chloro-thiophene-2-carboxylic acid-N-[2-(pyridin-3-yl)-1-(3-methyl-2,3,4,5-tetrahydro-1H-benzo[d]azepin-7-ylcarbamoyl)-ethyl]-amide | $(M + H)^+ =$ 469/471 (chlorine isotopes) | Rf: 0.54; silica gel; $CH_2Cl_2$/ethanol/ammonia = 80:20:2 |
| 100 | 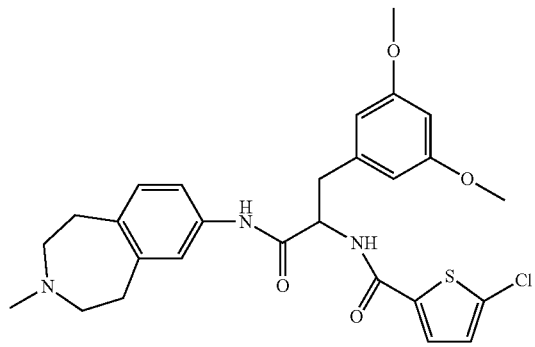 [SMILES: COc1cc(CC(NC(=O)c2ccc(Cl)s2)C(=O)Nc2ccc3c(c2)CCN(C)CC3)cc(OC)c1]<br>5-chloro-thiophene-2-carboxylic acid-N-[2-(3,5-dimethoxyphenyl)-1-(3-methyl-2,3,4,5-tetrahydro-1H-benzo[d]azepin-7-ylcarbamoyl)-ethyl]-amide | $(M + H)^+ =$ 528/530 (chlorine isotopes) | Rf: 0.27; silica gel; $CH_2Cl_2$/ethanol/ammonia = 90:10:1 |
| 101 | 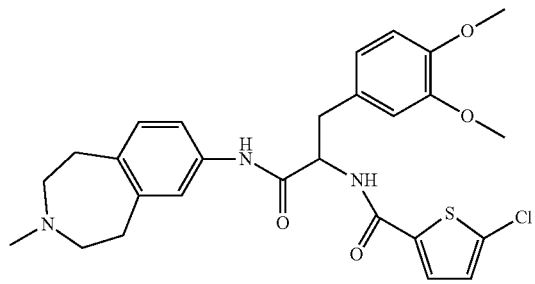 [SMILES: COc1ccc(CC(NC(=O)c2ccc(Cl)s2)C(=O)Nc2ccc3c(c2)CCN(C)CC3)cc1OC]<br>5-chloro-thiophene-2-carboxylic acid-N-[2-(3,4-dimethoxyphenyl)-1-(3-methyl-2,3,4,5-tetrahydro-1H-benzo[d]azepin-7-ylcarbamoyl)-ethyl]-amide | $(M + H)^+ =$ 528/530 (chlorine isotopes) | Rf: 0.7; silica gel; $CH_2Cl_2$/ethanol/ammonia = 80:20:2 |
| 102 | 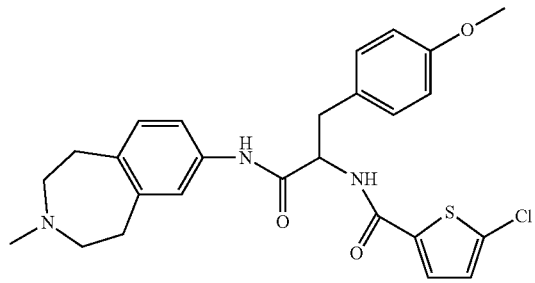 [SMILES: COc1ccc(CC(NC(=O)c2ccc(Cl)s2)C(=O)Nc2ccc3c(c2)CCN(C)CC3)cc1]<br>5-chloro-thiophene-2-carboxylic acid-N-[2-(4-methoxyphenyl)-1-(3-methyl-2,3,4,5-tetrahydro-1H-benzo[d]azepin-7-ylcarbamoyl)-ethyl]-amide | $(M + H)^+ =$ 498/500 (chlorine isotopes) | Rf: 0.7; silica gel; $CH_2Cl_2$/ethanol/ammonia = 80:20:2 |

| | | | |
|---|---|---|---|
| 103 | 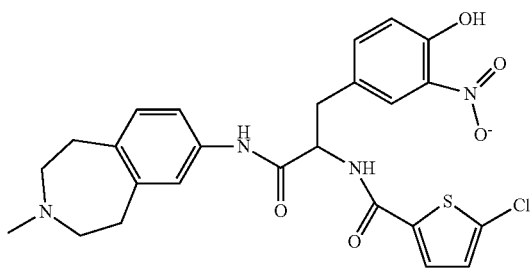<br>5-chloro-thiophene-2-carboxylic acid-N-[2-(4-hydroxy-3-nitro-phenyl)-1-(3-methyl-2,3,4,5-tetrahydro-1H-benzo[d]azepin-7-ylcarbamoyl)-ethyl]-amide | $(M + H)^+ =$ 529/531 (chlorine isotopes) | Rf: 0.18; silica gel; $CH_2Cl_2$/ethanol/ ammonia = 80:20:2 |
| 104 | 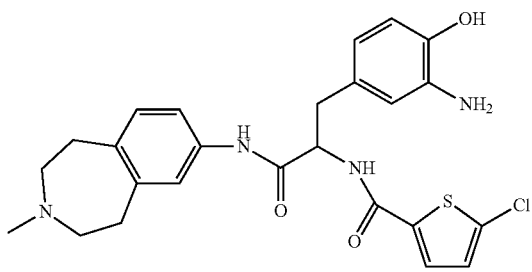 [SMILES: CN1CCc2ccc(NC(=O)C(Cc3ccc(O)c(N)c3)NC(=O)c3ccc(Cl)s3)cc2CC1]<br>5-chloro-thiophene-2-carboxylic acid-N-[2-(4-hydroxy-3-amino-phenyl)-1-(3-methyl-2,3,4,5-tetrahydro-1H-benzo[d]azepin-7-ylcarbamoyl)-ethyl]-amide | $(M + H)^+ =$ 499/501 (chlorine isotopes) | Rf: 0.30; silica gel; $CH_2Cl_2$/ethanol/ ammonia = 80:20:2 |
| 105 | 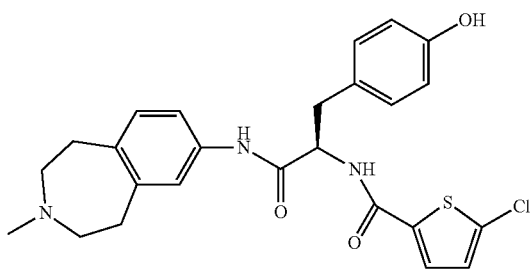 [SMILES: CN1CCc2ccc(NC(=O)[C@@H](Cc3ccc(O)cc3)NC(=O)c3ccc(Cl)s3)cc2CC1]<br>(R)-5-chloro-thiophene-2-carboxylic acid-N-[2-(4-hydroxy-phenyl)-1-(3-methyl-2,3,4,5-tetrahydro-1H-benzo[d]azepin-7-ylcarbamoyl)-ethyl]-amide | $(M + H)^+ =$ 484/486 (chlorine isotopes) | Rf: 0.5; silica gel; $CH_2Cl_2$/ethanol/ ammonia = 80:20:2 |
| 106 | 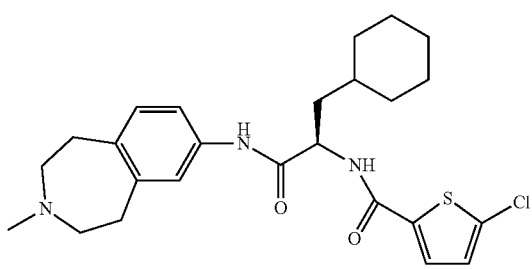 [SMILES: CN1CCc2ccc(NC(=O)[C@@H](CC3CCCCC3)NC(=O)c3ccc(Cl)s3)cc2CC1]<br>(R)-5-chloro-thiophene-2-carboxylic acid-N-[2-cyclohexyl-1-(3-methyl-2,3,4,5-tetrahydro-1H-benzo[d]azepin-7-ylcarbamoyl)-ethyl]-amide | $(M + H)^+ =$ 474/476 (chlorine isotopes) | Rf: 0.18; silica gel; $CH_2Cl_2$/ethanol = 80:20 |
| 107 | 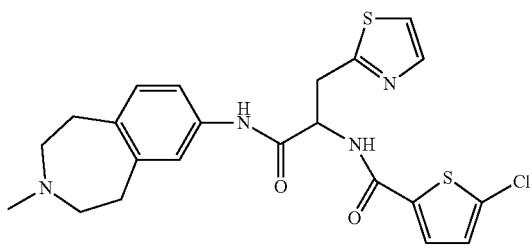 [SMILES: CN1CCc2ccc(NC(=O)C(Cc3nccs3)NC(=O)c3ccc(Cl)s3)cc2CC1]<br>5-chloro-thiophene-2-carboxylic acid-N-[2-(thiazol-2-yl)-1-(3-methyl-2,3,4,5-tetrahydro-1H-benzo[d]azepin-7-ylcarbamoyl)-ethyl]-amide | $(M + H)^+ =$ 475/477 (chlorine isotopes) | Rt: 2.7 min HPLC-method 4 |

| | | | |
|---|---|---|---|
| 108 | 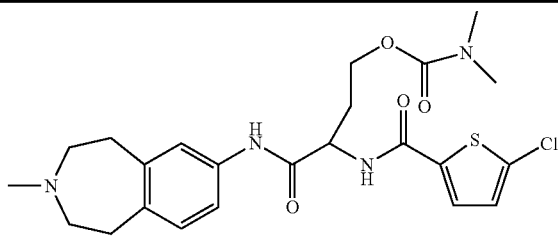  5-chloro-thiophene-2-carboxylic acid-N-[3-dimethylaminocarbonyloxy-1-(3-methyl-2,3,4,5-tetrahydro-1H-benzo[d]azepin-7-ylcarbamoyl)-propyl]-amide | (M + H)⁺ = 493/495 (chlorine isotopes) | Rt: 4.14 min HPLC-method 3 |
| 109 | 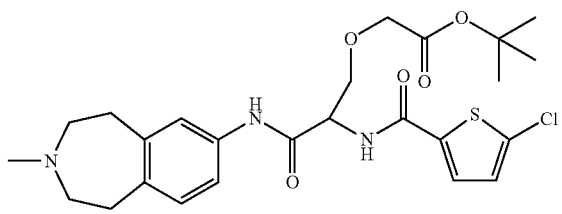 [SMILES: CN1CCc2ccc(NC(=O)C(COCC(=O)OC(C)(C)C)NC(=O)c3ccc(Cl)s3)cc2CC1]  5-chloro-thiophene-2-carboxylic acid-N-[2-tert.butoyloxycarbonylmethyloxy-1-(3-methyl-2,3,4,5-tetrahydro-1H-benzo[d]azepin-7-ylcarbamoyl)-ethyl]-amide | (M + H)⁺ = 522/524 (chlorine isotopes) | Rf: 0.74; silica gel; CH₂Cl₂/ethanol/ ammonia = 80:20:2 |
| 110 | 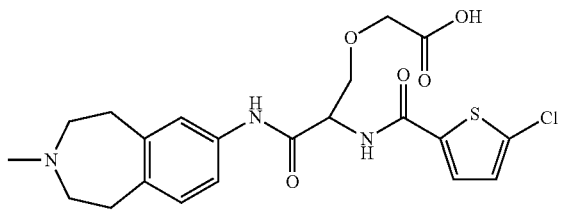 [SMILES: CN1CCc2ccc(NC(=O)C(COCC(=O)O)NC(=O)c3ccc(Cl)s3)cc2CC1]  5-chloro-thiophene-2-carboxylic acid-N-[2-hydroxycarbonylmethyloxy-1-(3-methyl-2,3,4,5-tetrahydro-1H-benzo[d]azepin-7-ylcarbamoyl)-ethyl]-amide | (M + H)⁻ = 464/466 (chlorine isotopes) | Rf: 0.45; RP8; MeOH/5% NaCl solution = 6/4 |
| 111 | 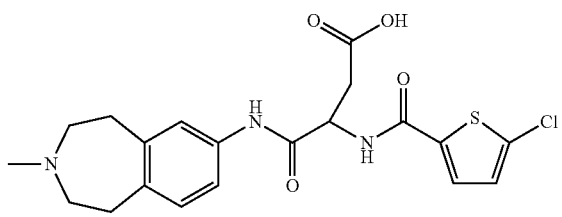 [SMILES: CN1CCc2ccc(NC(=O)C(CC(=O)O)NC(=O)c3ccc(Cl)s3)cc2CC1]  5-chloro-thiophene-2-carboxylic acid-N-[2-hydroxycarbonyl-1-(3-methyl-2,3,4,5-tetrahydro-1H-benzo[d]azepin-7-ylcarbamoyl)-ethyl]-amide | (M + H)⁺ = 436/438 (chlorine isotopes) | Rf: 0.65; RP8; MeOH/5% NaCl solution = 6/4 |
| 112 | 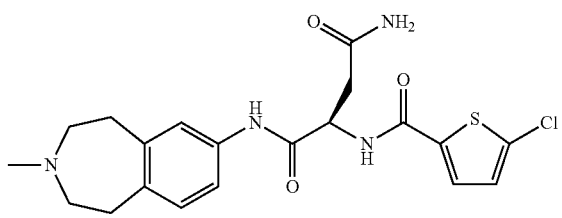 [SMILES: CN1CCc2ccc(NC(=O)[C@@H](CC(N)=O)NC(=O)c3ccc(Cl)s3)cc2CC1]  (R)-5-chloro-thiophene-2-carboxylic acid-N-[2-aminocarbonyl-1-(3-methyl-2,3,4,5-tetrahydro-1H-benzo[d]azepin-7-ylcarbamoyl)-ethyl]-amide | (M + H)⁺ = 435/437 (chlorine isotopes) | Rf: 0.25; silica gel; CH₂Cl₂/ethanol/ ammonia = 80:20:2 |
| 113 | 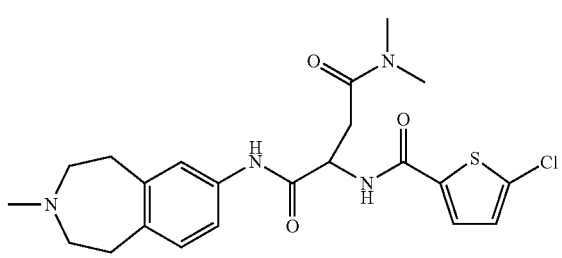 [SMILES: CN1CCc2ccc(NC(=O)C(CC(=O)N(C)C)NC(=O)c3ccc(Cl)s3)cc2CC1]  5-chloro-thiophene-2-carboxylic acid-N-[2-dimethylaminocarbonyl-1-(3-methyl-2,3,4,5-tetrahydro-1H-benzo[d]azepin-7-ylcarbamoyl)-ethyl]-amide | (M + H)⁺ = 463/465 (chlorine isotopes) | Rf: 0.6; silica gel; CH₂Cl₂/ethanol/ ammonia = 80:20:2 |

| 114 | 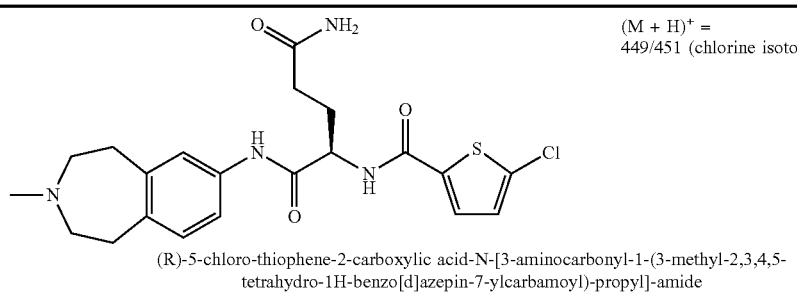 (R)-5-chloro-thiophene-2-carboxylic acid-N-[3-aminocarbonyl-1-(3-methyl-2,3,4,5-tetrahydro-1H-benzo[d]azepin-7-ylcarbamoyl)-propyl]-amide | $(M + H)^+$ = 449/451 (chlorine isotopes) | Rf: 0.2; silica gel; $CH_2Cl_2$/ethanol/ammonia = 80:20:2 |
|---|---|---|---|
| 115 | 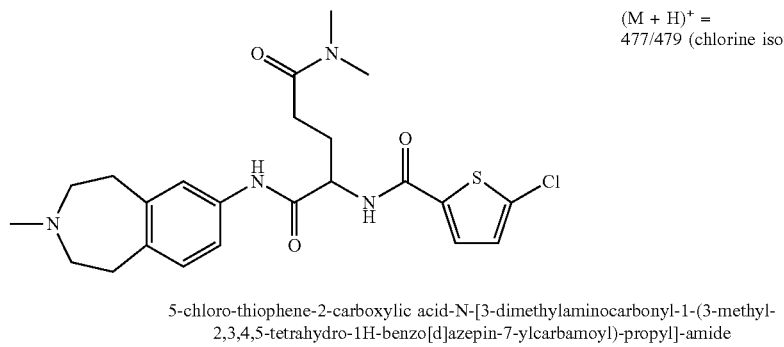 5-chloro-thiophene-2-carboxylic acid-N-[3-dimethylaminocarbonyl-1-(3-methyl-2,3,4,5-tetrahydro-1H-benzo[d]azepin-7-ylcarbamoyl)-propyl]-amide | $(M + H)^+$ = 477/479 (chlorine isotopes) | Rf: 0.3; silica gel; $CH_2Cl_2$/ethanol/ammonia = 80:20:2 |
| 116 | 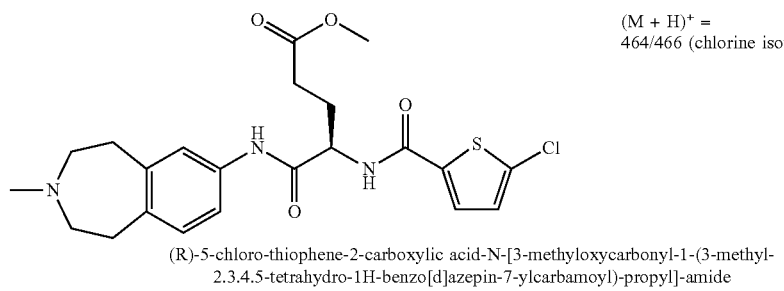 (R)-5-chloro-thiophene-2-carboxylic acid-N-[3-methyloxycarbonyl-1-(3-methyl-2,3,4,5-tetrahydro-1H-benzo[d]azepin-7-ylcarbamoyl)-propyl]-amide | $(M + H)^+$ = 464/466 (chlorine isotopes) | Rt: 0.94 min HPLC-method 5 |
| 117 | 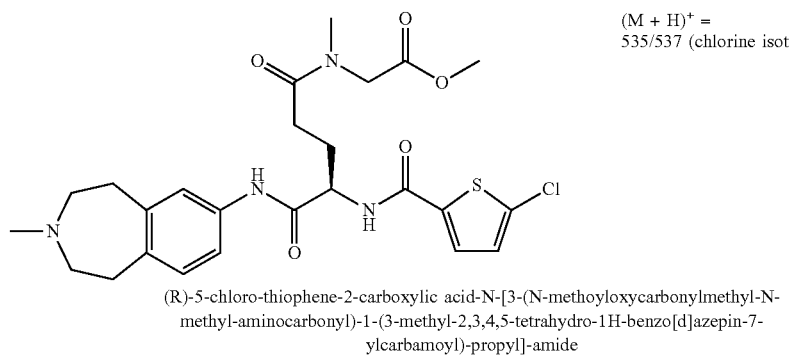 (R)-5-chloro-thiophene-2-carboxylic acid-N-[3-(N-methoyloxycarbonylmethyl-N-methyl-aminocarbonyl)-1-(3-methyl-2,3,4,5-tetrahydro-1H-benzo[d]azepin-7-ylcarbamoyl)-propyl]-amide | $(M + H)^+$ = 535/537 (chlorine isotopes) | Rt: 0.90 min HPLC-method 5 |
| 118 | 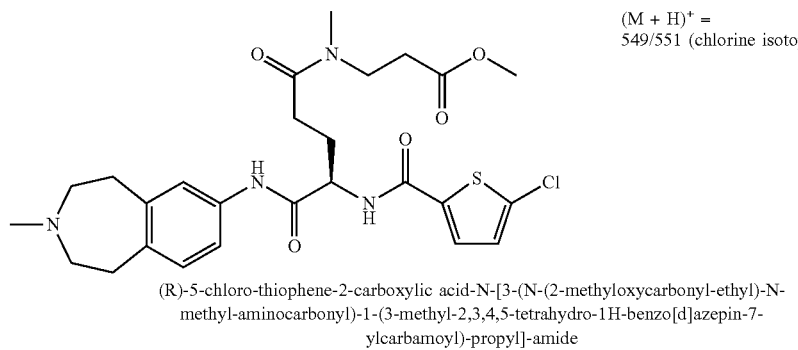 (R)-5-chloro-thiophene-2-carboxylic acid-N-[3-(N-(2-methyloxycarbonyl-ethyl)-N-methyl-aminocarbonyl)-1-(3-methyl-2,3,4,5-tetrahydro-1H-benzo[d]azepin-7-ylcarbamoyl)-propyl]-amide | $(M + H)^+$ = 549/551 (chlorine isotopes) | Rt: 0.89 min HPLC-method 5 |

| 119 | 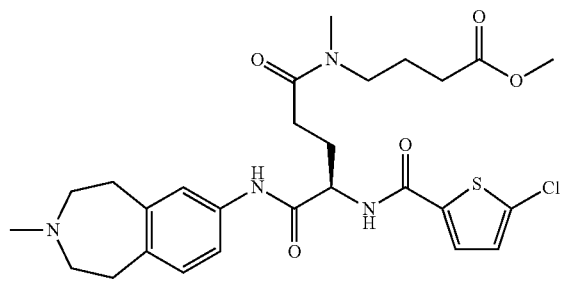 | (M + H)+ = 563/565 (chlorine isotopes) | Rt: 0.89 min HPLC-method 5 |

(R)-5-chloro-thiophene-2-carboxylic acid-N-[3-(N-(3-methyloxycarbonyl-propyl)-N-methyl-aminocarbonyl)-1-(3-methyl-2,3,4,5-tetrahydro-1H-benzo[d]azepin-7-ylcarbamoyl)-propyl]-amide

| 120 | 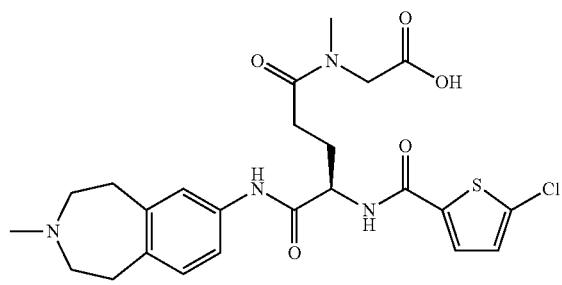 [SMILES: CN1CCc2ccc(NC(=O)[C@@H](CCC(=O)N(C)CC(=O)O)NC(=O)c3ccc(Cl)s3)cc2CC1] | (M + H)+ = 521/523 (chlorine isotopes) | Rt: 0.84 min HPLC-method 5 |

(R)-5-chloro-thiophene-2-carboxylic acid-N-[3-(N-hydroxycarbonylmethyl-N-methyl-aminocarbonyl)-1-(3-methyl-2,3,4,5-tetrahydro-1H-benzo[d]azepin-7-ylcarbamoyl)-propyl]-amide

| 121 | 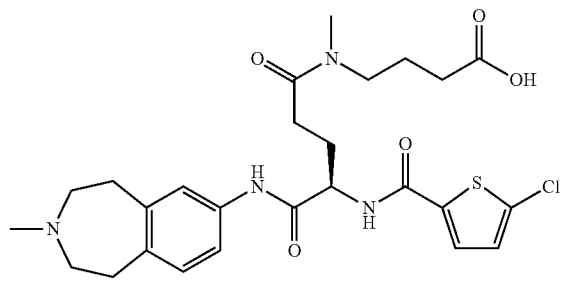 [SMILES: CN1CCc2ccc(NC(=O)[C@@H](CCC(=O)N(C)CCCC(=O)O)NC(=O)c3ccc(Cl)s3)cc2CC1] | (M + H)+ = 549/551 (chlorine isotopes) | Rt: 0.85 min HPLC-method 5 |

(R)-5-chloro-thiophene-2-carboxylic acid-N-[3-(N-(3-hydroxycarbonyl-propyl)-N-methyl-aminocarbonyl)-1-(3-methyl-2,3,4,5-tetrahydro-1H-benzo[d]azepin-7-ylcarbamoyl)-propyl]-amide

| 122 | 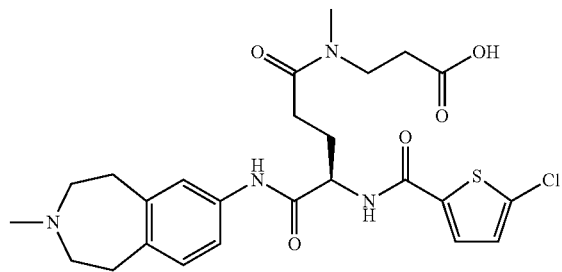 [SMILES: CN1CCc2ccc(NC(=O)[C@@H](CCC(=O)N(C)CCC(=O)O)NC(=O)c3ccc(Cl)s3)cc2CC1] | (M + H)+ = 535/537 (chlorine isotopes) | Rt: 0.84 min HPLC-method 5 |

(R)-5-chloro-thiophene-2-carboxylic acid-N-[3-(N-(2-hydroxycarbonyl-ethyl)-N-methyl-aminocarbonyl)-1-(3-methyl-2,3,4,5-tetrahydro-1H-benzo[d]azepin-7-ylcarbamoyl)-propyl]-amide

| | | | |
|---|---|---|---|
| 123 | 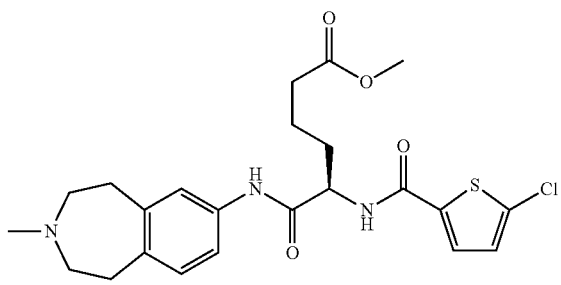 [SMILES: COC(=O)CCC[C@@H](NC(=O)c1ccc(Cl)s1)C(=O)Nc1ccc2c(c1)CCN(C)CC2] (R)-5-chloro-thiophene-2-carboxylic acid-N-[4-methyloxycarbonyl-1-(3-methyl-2,3,4,5-tetrahydro-1H-benzo[d]azepin-7-ylcarbamoyl)-butyl]-amide | $(M + H)^+ =$ 478/480 (chlorine isotopes) | Rt: 2.55 min HPLC-method 2 |
| 124 | 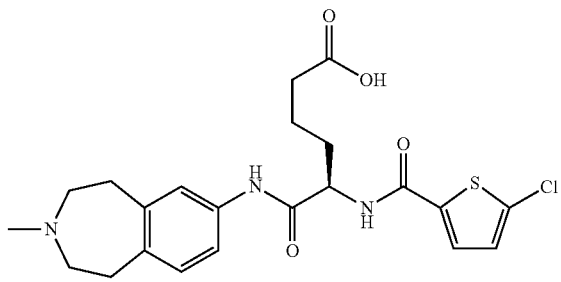 [SMILES: CN1CCc2ccc(NC(=O)[C@@H](CCCC(=O)O)NC(=O)c3ccc(Cl)s3)cc2CC1] (R)-5-chloro-thiophene-2-carboxylic acid-N-[4-hydroxycarbonyl-1-(3-methyl-2,3,4,5-tetrahydro-1H-benzo[d]azepin-7-ylcarbamoyl)-butyl]-amide | $(M + H)^+ =$ 464/466 (chlorine isotopes) | Rt: 3.87 min HPLC-method 3 |
| 125 | 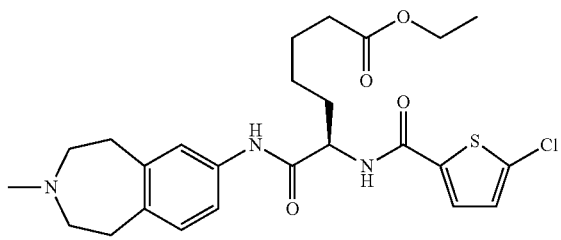 [SMILES: CCOC(=O)CCCC[C@@H](NC(=O)c1ccc(Cl)s1)C(=O)Nc1ccc2c(c1)CCN(C)CC2] (R)-5-chloro-thiophene-2-carboxylic acid-N-[5-ethyloxycarbonyl-1-(3-methyl-2,3,4,5-tetrahydro-1H-benzo[d]azepin-7-ylcarbamoyl)-phenyl]-amide | $(M + H)^+ =$ 506/508 (chlorine isotopes) | Rt: 2.71 min HPLC-method 2 |
| 126 | 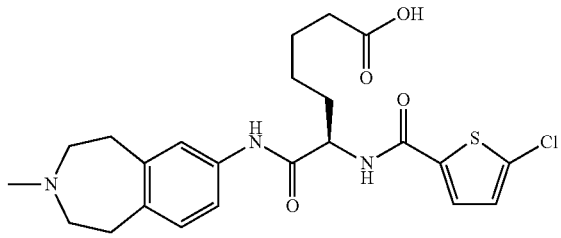 [SMILES: CN1CCc2ccc(NC(=O)[C@@H](CCCCC(=O)O)NC(=O)c3ccc(Cl)s3)cc2CC1] (R)-5-chloro-thiophene-2-carboxylic acid-N-[5-hydroxycarbonyl-1-(3-methyl-2,3,4,5-tetrahydro-1H-benzo[d]azepin-7-ylcarbamoyl)-pentyl]-amide | $(M + H)^+ =$ 478/480 (chlorine isotopes) | Rt: 3.96 min HPLC-method 3 |
| 127 | 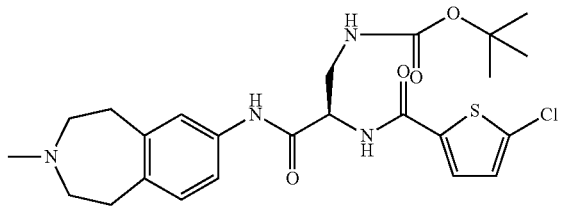 [SMILES: CN1CCc2ccc(NC(=O)[C@@H](CNC(=O)OC(C)(C)C)NC(=O)c3ccc(Cl)s3)cc2CC1] (R)-5-chloro-thiophene-2-carboxylic acid-N-[2-tert.butyloxycarbonylamino-1-(3-methyl-2,3,4,5-tetrahydro-1H-benzo[d]azepin-7-ylcarbamoyl)-ethyl]-amide | $(M + H)^+ =$ 507/509 (chlorine isotopes) | Rt: 4.43 min HPLC-method 3 |

| | | | |
|---|---|---|---|
| 128 | 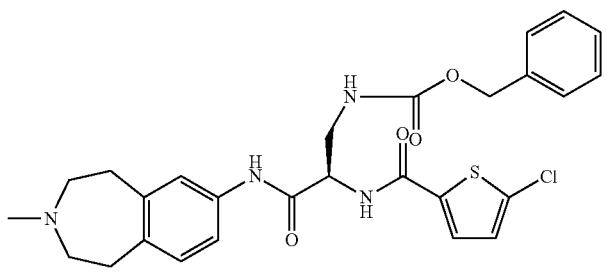 [SMILES: CN1CCc2ccc(NC(=O)[C@@H](CNC(=O)OCc3ccccc3)NC(=O)c3ccc(Cl)s3)cc2CC1] | (M + H)+ = 541/543 (chlorine isotopes) | Rt: 1.03 min HPLC-method 5 |
| | (R)-5-chloro-thiophene-2-carboxylic acid-N-[2-benzyloxycarbonylamino-1-(3-methyl-2,3,4,5-tetrahydro-1H-benzo[d]azepin-7-ylcarbamoyl)-ethyl]-amide | | |
| 129 | 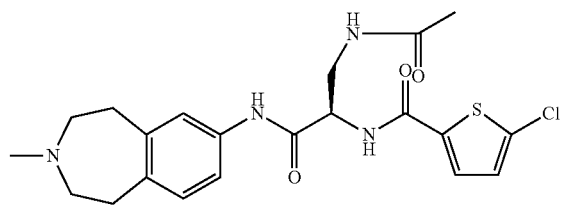 [SMILES: CC(=O)NC[C@@H](NC(=O)c1ccc(Cl)s1)C(=O)Nc1ccc2c(c1)CCN(C)CC2] | (M + H)+ = 449/451 (chlorine isotopes) | Rt: 0.84 min HPLC-method 5 |
| | (R)-5-chloro-thiophene-2-carboxylic acid-N-[2-acetylamino-1-(3-methyl-2,3,4,5-tetrahydro-1H-benzo[d]azepin-7-ylcarbamoyl)-ethyl]-amide | | |
| 130 | 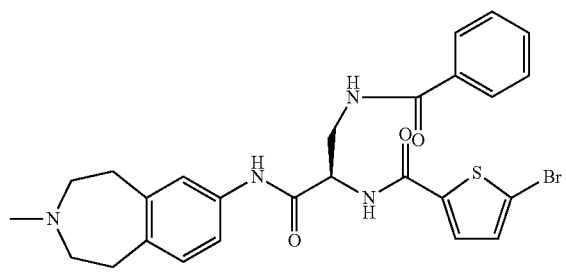 [SMILES: CN1CCc2ccc(NC(=O)[C@@H](CNC(=O)c3ccccc3)NC(=O)c3ccc(Br)s3)cc2CC1] | (M + H)+ = 555/557 (bromine isotopes) | Rt: 0.98 min HPLC-method 5 |
| | (R)-5-bromo-thiophene-2-carboxylic acid-N-[2-benzoylamino-1-(3-methyl-2,3,4,5-tetrahydro-1H-benzo[d]azepin-7-ylcarbamoyl)-ethyl]-amide | | |
| 131 | 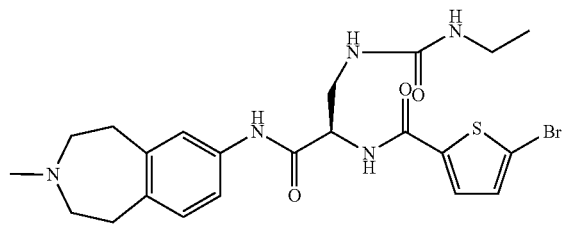 [SMILES: CCNC(=O)NC[C@@H](NC(=O)c1ccc(Br)s1)C(=O)Nc1ccc2c(c1)CCN(C)CC2] | (M + H)+ = 522/524 (bromine isotopes) | Rt: 0.90 min HPLC-method 5 |
| | (R)-5-bromo-thiophene-2-carboxylic acid-N-[2-ethylaminocarbonylamino-1-(3-methyl-2,3,4,5-tetrahydro-1H-benzo[d]azepin-7-ylcarbamoyl)-ethyl]-amide | | |
| 132 | 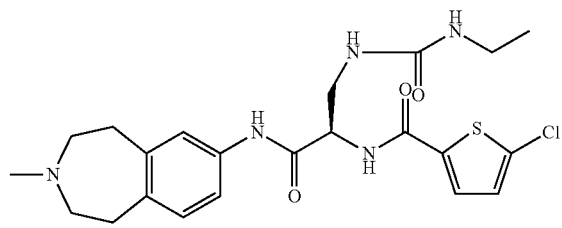 [SMILES: CCNC(=O)NC[C@@H](NC(=O)c1ccc(Cl)s1)C(=O)Nc1ccc2c(c1)CCN(C)CC2] | (M + H)+ = 478/480 (chlorine isotopes) | Rt: 0.88 min HPLC-method 5 |
| | (R)-5-chloro-thiophene-2-carboxylic acid-N-[2-ethylaminocarbonylamino-1-(3-methyl-2,3,4,5-tetrahydro-1H-benzo[d]azepin-7-ylcarbamoyl)-ethyl]-amide | | |

| | | | |
|---|---|---|---|
| 133 | 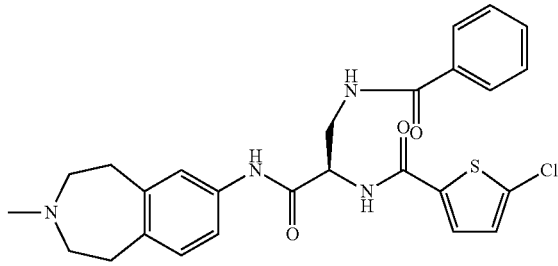 [SMILES: CN1CCc2ccc(NC(=O)[C@@H](CNC(=O)c3ccccc3)NC(=O)c3ccc(Cl)s3)cc2CC1]<br>(R)-5-chloro-thiophene-2-carboxylic acid-N-[2-benzoylamino-1-(3-methyl-2,3,4,5-tetrahydro-1H-benzo[d]azepin-7-ylcarbamoyl)-ethyl]-amide | $(M + H)^+$ = 511/513 (chlorine isotopes) | Rt: 0.97 min<br>HPLC-method 5 |
| 134 | 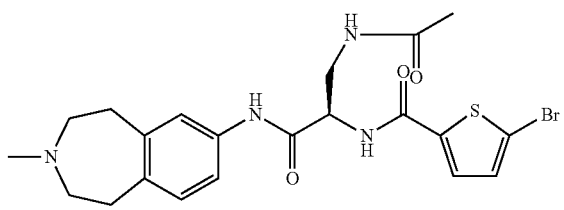 [SMILES: CC(=O)NC[C@@H](NC(=O)c1ccc(Br)s1)C(=O)Nc1ccc2c(c1)CCN(C)CC2]<br>(R)-5-bromo-thiophene-2-carboxylic acid-N-[2-acetylamino-1-(3-methyl-2,3,4,5-tetrahydro-1H-benzo[d]azepin-7-ylcarbamoyl)-ethyl]-amide | $(M + H)^+$ = 493/495 (bromine isotopes) | Rt: 0.85 min<br>HPLC-method 5 |
| 135 | 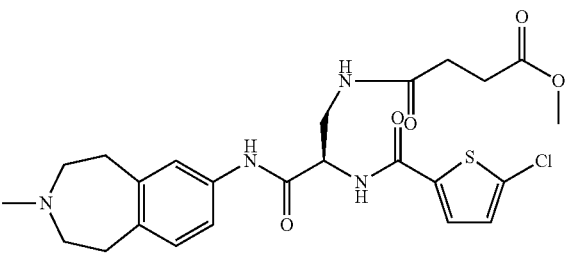<br>(R)-5-chloro-thiophene-2-carboxylic acid-N-[2-(2-methoxycarbonyl-ethyl)carbonylamino-1-(3-methyl-2,3,4,5-tetrahydro-1H-benzo[d]azepin-7-ylcarbamoyl)-ethyl]-amide | $(M + H)^+$ = 521/523 (chlorine isotopes) | Rt: 3.99 min<br>HPLC-method 3 |
| 136 | 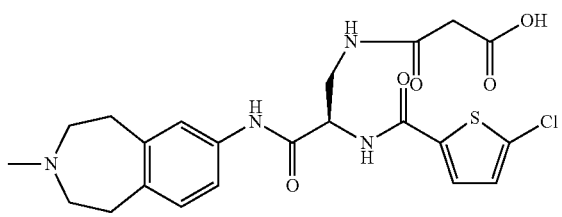 [SMILES: CN1CCc2ccc(NC(=O)[C@@H](CNC(=O)CC(=O)O)NC(=O)c3ccc(Cl)s3)cc2CC1]<br>(R)-5-chloro-thiophene-2-carboxylic acid-N-[2-hydroxycarbonylmethylcarbonylamino-1-(3-methyl-2,3,4,5-tetrahydro-1H-benzo[d]azepin-7-ylcarbamoyl)-ethyl]-amide | $(M + H)^+$ = 493/495 (chlorine isotopes) | Rt: 3.61 min<br>HPLC-method 3 |
| 137 | 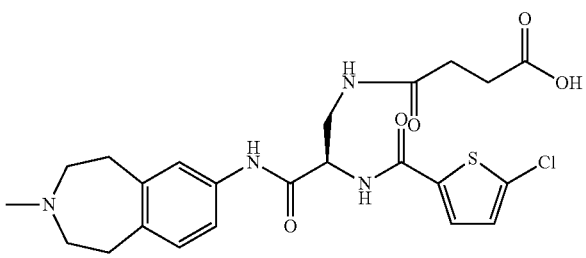 [SMILES: CN1CCc2ccc(NC(=O)[C@@H](CNC(=O)CCC(=O)O)NC(=O)c3ccc(Cl)s3)cc2CC1]<br>(R)-5-chloro-thiophene-2-carboxylic acid-N-[2-(2-hydroxycarbonyl-ethyl)carbonylamino-1-(3-methyl-2,3,4,5-tetrahydro-1H-benzo[d]azepin-7-ylcarbamoyl)-ethyl]-amide | $(M + H)^+$ = 507/509 (chlorine isotopes) | Rt: 3.64 min<br>HPLC-method 3 |

| | | | |
|---|---|---|---|
| 138 | 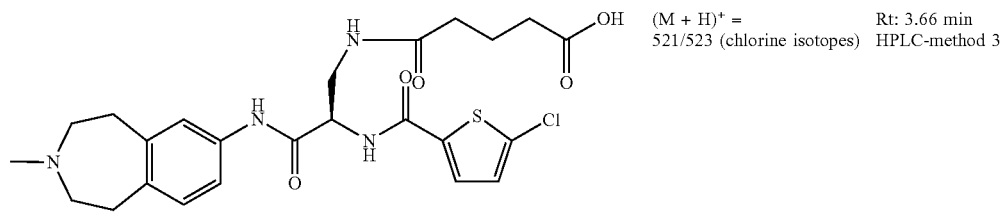 (R)-4-chloro-thiophene-2-carboxylic acid-N-[2-(3-hydroxycarbonyl-propyl)carbonylamino-1-(3-methyl-2,3,4,5-tetrahydro-1H-benzo[d]azepin-7-ylcarbamoyl)-ethyl]-amide | $(M + H)^+$ = 521/523 (chlorine isotopes) | Rt: 3.66 min HPLC-method 3 |
| 139 | 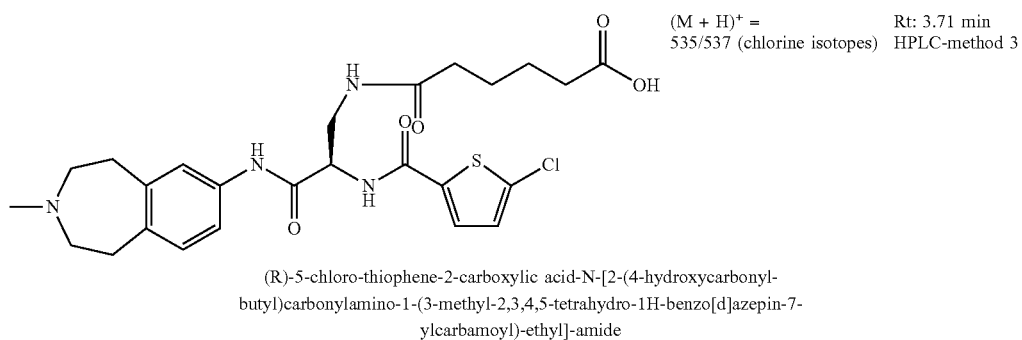 (R)-5-chloro-thiophene-2-carboxylic acid-N-[2-(4-hydroxycarbonyl-butyl)carbonylamino-1-(3-methyl-2,3,4,5-tetrahydro-1H-benzo[d]azepin-7-ylcarbamoyl)-ethyl]-amide | $(M + H)^+$ = 535/537 (chlorine isotopes) | Rt: 3.71 min HPLC-method 3 |
| 140 | 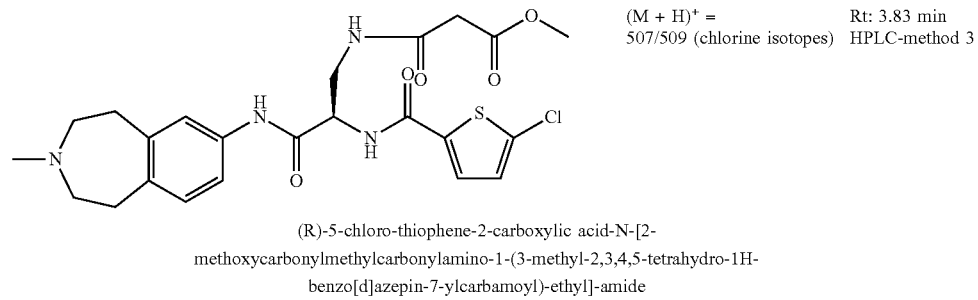 (R)-5-chloro-thiophene-2-carboxylic acid-N-[2-methoxycarbonylmethylcarbonylamino-1-(3-methyl-2,3,4,5-tetrahydro-1H-benzo[d]azepin-7-ylcarbamoyl)-ethyl]-amide | $(M + H)^+$ = 507/509 (chlorine isotopes) | Rt: 3.83 min HPLC-method 3 |
| 141 | 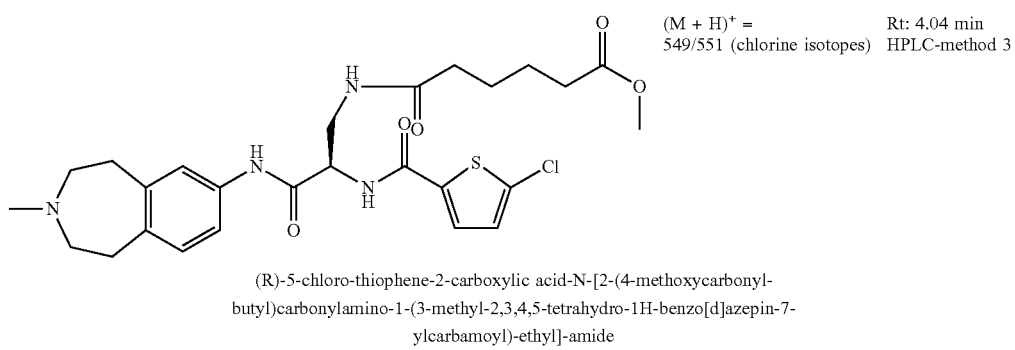 (R)-5-chloro-thiophene-2-carboxylic acid-N-[2-(4-methoxycarbonyl-butyl)carbonylamino-1-(3-methyl-2,3,4,5-tetrahydro-1H-benzo[d]azepin-7-ylcarbamoyl)-ethyl]-amide | $(M + H)^+$ = 549/551 (chlorine isotopes) | Rt: 4.04 min HPLC-method 3 |
| 142 | 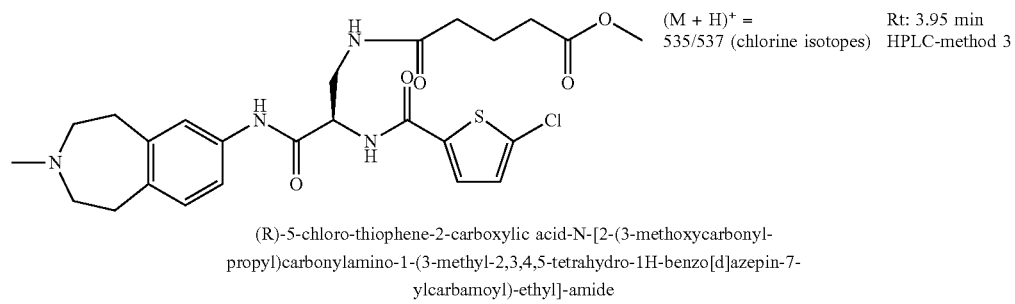 (R)-5-chloro-thiophene-2-carboxylic acid-N-[2-(3-methoxycarbonyl-propyl)carbonylamino-1-(3-methyl-2,3,4,5-tetrahydro-1H-benzo[d]azepin-7-ylcarbamoyl)-ethyl]-amide | $(M + H)^+$ = 535/537 (chlorine isotopes) | Rt: 3.95 min HPLC-method 3 |

| 143 | 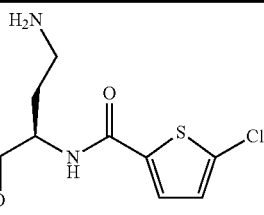 (R)-5-chloro-thiophene-2-carboxylic acid-N-[3-amino-1-(3-methyl-2,3,4,5-tetrahydrp-1H-benzo[d]azepin-7-ylcarbamoyl)-propyl]-amide | $(M + H)^+$ = 421/423 (chlorine isotopes) | Rt: 0.77 min HPLC-method 5 |
|---|---|---|---|
| 144 | 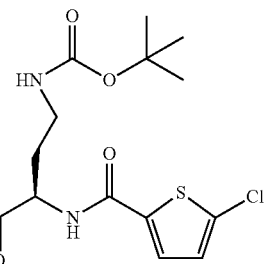 (R)-5-chloro-thiophene-2-carboxylic acid-N-[3-tert.butoxycarbonylamino-1-(3-methyl-2,3,4,5-tetrahydro-1H-benzo[d]azepin-7-ylcarbamoyl)-propyl]-amide | $(M + H)^+$ = 521/523 (chlorine isotopes) | Rt: 1.02 min HPLC-method 5 |
| 145 | 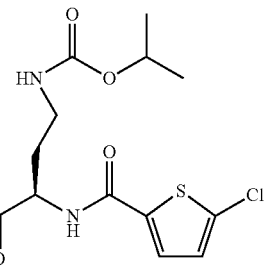 (R)-5-chloro-thiophene-2-carboxylic acid-N-[3-isopropyloxycarbonylamino-1-(3-methyl-2,3,4,5-tetrahydro-1H-benzo[d]azepin-7-ylcarbamoyl)-propyl]-amide | $(M + H)^+$ = 507/509 (chlorine isotopes) | Rt: 0.97 min HPLC-method 5 |
| 146 | 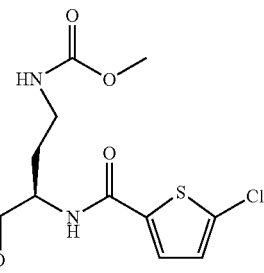 (R)-5-chloro-thiophene-2-carboxylic acid-N-[3-methyloxycarbonylamino-1-(3-methyl-2,3,4,5-tetrahydro-1H-benzo[d]azepin-7-ylcarbamoyl)-propyl]-amide | $(M + H)^+$ = 479/481 (chlorine isotopes) | Rt: 0.90 min HPLC-method 5 |
| 147 | 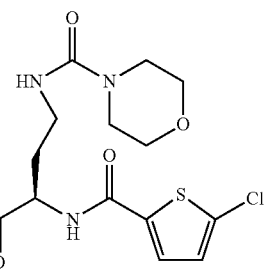 (R)-5-chloro-thiophene-2-carboxylic acid-N-[3-(morpholine-4-yl)carbonylamino-1-(3-methyl-2,3,4,5-tetrahydro-1H-benzo[d]azepin-7-ylcarbamoyl)-propyl]-amide | $(M + H)^+$ = 534/536 (chlorine isotopes) | Rt: 0.87 min HPLC-method 5 |

| | | | |
|---|---|---|---|
| 148 | 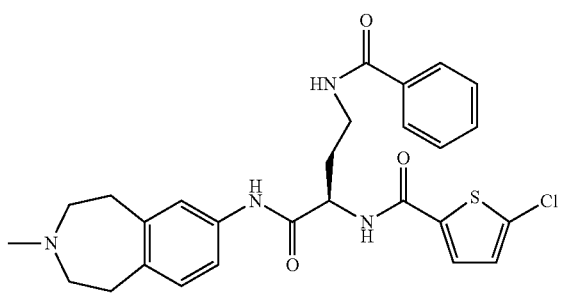 [SMILES: CN1CCc2ccc(NC(=O)[C@@H](CCNC(=O)c3ccccc3)NC(=O)c3ccc(Cl)s3)cc2CC1](R)-5-chloro-thiophene-2-carboxylic acid-N-[3-benzoylamino-1-(3-methyl-2,3,4,5-tetrahydro-1H-benzo[d]azepin-7-ylcarbamoyl)-propyl]-amide | $(M + H)^+ =$ 525/527 (chlorine isotopes) | Rt: 0.97 min HPLC-method 5 |
| 149 | 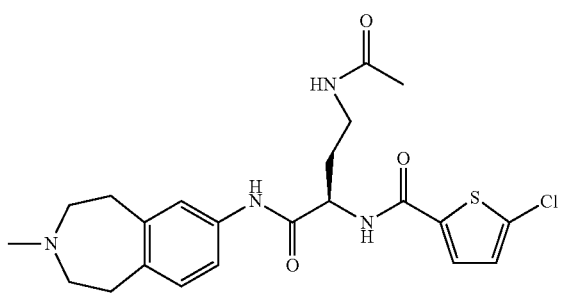 [SMILES: CC(=O)NCC[C@@H](NC(=O)c1ccc(Cl)s1)C(=O)Nc1ccc2c(c1)CCN(C)CC2](R)-5-chloro-thiophene-2-carboxylic acid-N-[3-acetylamino-1-(3-methyl-2,3,4,5-tetrahydro-1H-benzo[d]azepin-7-ylcarbamoyl)-propyl]-amide | $(M + H)^+ =$ 463/465 (chlorine isotopes) | Rt: 0.85 min HPLC-method 5 |
| 150 | 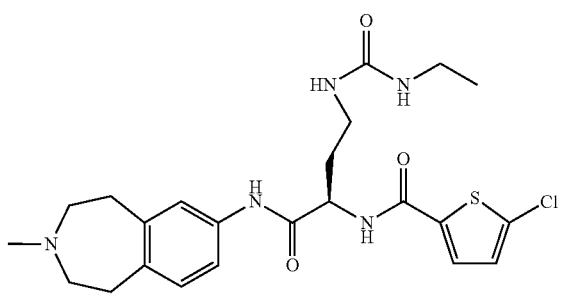 [SMILES: CCNC(=O)NCC[C@@H](NC(=O)c1ccc(Cl)s1)C(=O)Nc1ccc2c(c1)CCN(C)CC2](R)-5-chloro-thiophene-2-carboxylic acid-N-[3-ethylaminocarbonylamino-1-(3-methyl-2,3,4,5-tetrahydro-1H-benzo[d]azepin-7-ylcarbamoyl)-propyl]-amide | $(M + H)^+ =$ 492/494 (chlorine isotopes) | Rt: 0.88 min HPLC-method 5 |
| 151 | 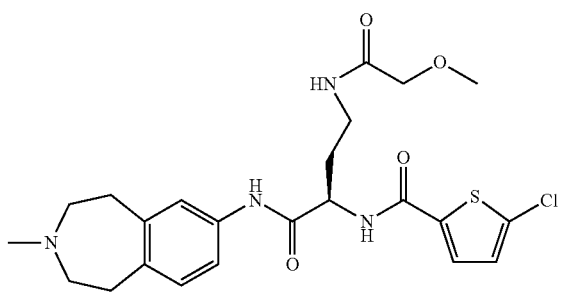 [SMILES: COCC(=O)NCC[C@@H](NC(=O)c1ccc(Cl)s1)C(=O)Nc1ccc2c(c1)CCN(C)CC2](R)-5-chloro-thiophene-2-carboxylic acid-N-[3-methyloxymethylcarbonylamino-1-(3-methyl-2,3,4,5-tetrahydro-1H-benzo[d]azepin-7-ylcarbamoyl)-propyl]-amide | $(M + H)^+ =$ 493/495 (chlorine isotopes) | Rt: 0.88 min HPLC-method 5 |

| | | | |
|---|---|---|---|
| 152 | 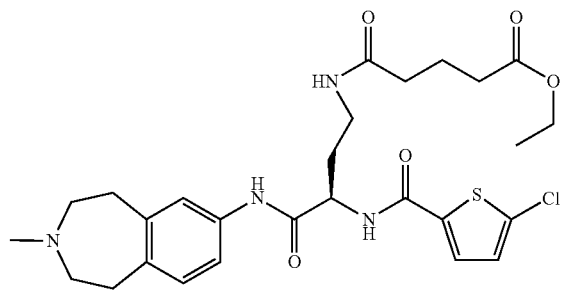 [SMILES: CCOC(=O)CCCC(=O)NCC[C@@H](NC(=O)c1ccc(Cl)s1)C(=O)Nc1ccc2c(c1)CCN(C)CC2]<br>(R)-5-chloro-thiophene-2-carboxylic acid-N-[3-(3-ethyloxycarbonyl-propyl)carbonylamino-1-(3-methyl-2,3,4,5-tetrahydro-1H-benzo[d]azepin-7-ylcarbamoyl)-propyl]-amide | (M + H)⁺ =<br>563/565 (chlorine isotopes) | Rt: 0.94 min<br>HPLC-method 5 |
| 153 | 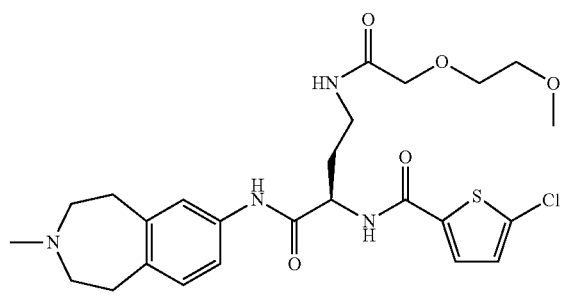<br>(R)-5-chloro-thiophene-2-carboxylic acid-N-[3-(2-methyloxy-ethyl)methylcarbonylamino-1-(3-methyl-2,3,4,5-tetrahydro-1H-benzo[d]azepin-7-ylcarbamoyl)-propyl]-amide | (M + H)⁺ =<br>537/539 (chlorine isotopes) | Rt: 0.89 min<br>HPLC-method 5 |
| 154 | 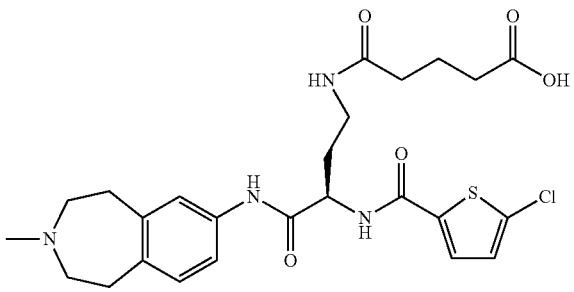 [SMILES: CN1CCc2ccc(NC(=O)[C@@H](CCNC(=O)CCCC(=O)O)NC(=O)c3ccc(Cl)s3)cc2CC1]<br>(R)-5-chloro-thiophene-2-carboxylic acid-N-[3-(3-hydroxycarbonyl-propyl)carbonylamino-1-(3-methyl-2,3,4,5-tetrahydro-1H-benzo[d]azepin-7-ylcarbamoyl)-propyl]-amide | (M + H)⁺ =<br>535/537 (chlorine isotopes) | Rt: 0.85 min<br>HPLC-method 5 |
| 155 | 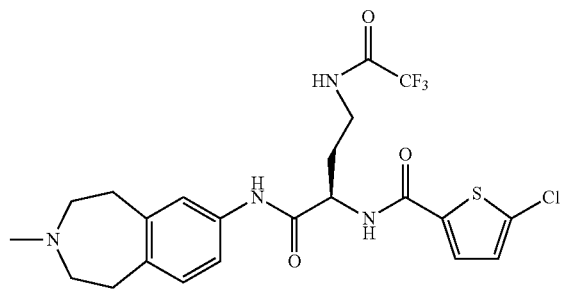 [SMILES: CN1CCc2ccc(NC(=O)[C@@H](CCNC(=O)C(F)(F)F)NC(=O)c3ccc(Cl)s3)cc2CC1]<br>(R)-5-chloro-thiophene-2-carboxylic acid-N-[3-trifluoromethylcarbonylamino-1-(3-methyl-2,3,4,5-tetrahydro-1H-benzo[d]azepin-7-ylcarbamoyl)-propyl]-amide | (M + H)⁺ =<br>517/519 (chlorine isotopes) | Rt: 0.98 min<br>HPLC-method 5 |

| 156 | 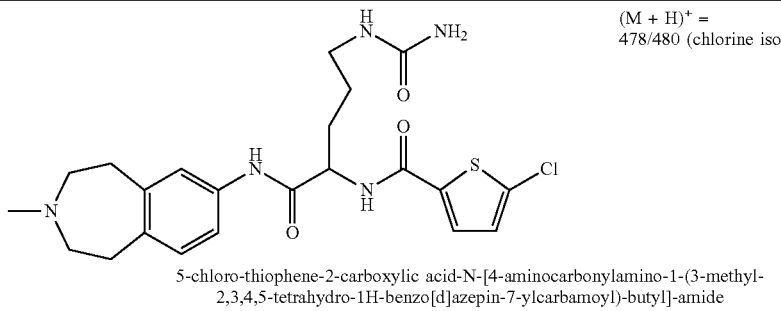 5-chloro-thiophene-2-carboxylic acid-N-[4-aminocarbonylamino-1-(3-methyl-2,3,4,5-tetrahydro-1H-benzo[d]azepin-7-ylcarbamoyl)-butyl]-amide | (M + H)⁺ = 478/480 (chlorine isotopes) | Rf: 0.2; silica gel; CH$_2$Cl$_2$/ethanol/ ammonia = 80:20:2 |
|---|---|---|---|

Example 157

5-chloro-thiophene-2-carboxylic acid-N-[1-methyl-1-(3,3-dimethyl-2,3,4,5-tetrahydro-1H-benzo[d]aze-pinium-7-ylcarbamoyl]-ethyl}-amide iodide

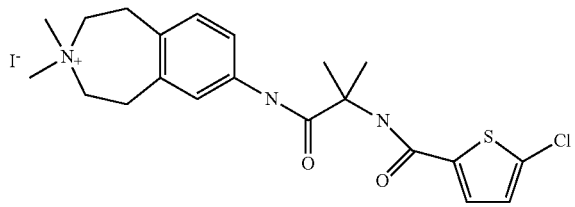 [SMILES: [I-] ; CC(C)(NC(=O)c1ccc(Cl)s1)C(=O)Nc1ccc2c(c1)CC[N+](C)(C)CC2]

A mixture of 0.50 g (2.43 mmol) 3-methyl-7-nitro-2,3,4,5-tetrahydro-1H-benzo[d]azepine, 0.44 ml (7.0 mmol) iodomethane and 2.0 ml acetonitrile are stirred for 1 h at room temperature and for 1 h at boiling temperature. The precipitate formed is suction filtered and dried. Then the mixture is hydrogenated analogously to Example 1(c) and reacted to form the title compound analogously to 1(f).

R$_t$ value: 2.7 min (HPLC-MS; method 4)
C$_{21}$H$_{27}$ClN$_3$O$_2$SI (547.88)
Mass spectrum: =420/422 (chlorine isotopes)

Example 158

1-[(5-chloro-thiophen-2-yl)-carbonylamino]-N-(3-methyl-3-oxy-2,3,4,5-tetrahydro-1H-benzo[d]aze-pin-7-yl)-cyclopentane-1-carboxylic acid amide

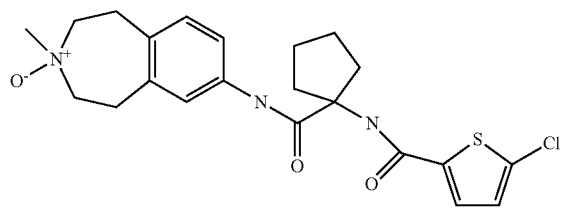 [SMILES: C[N+]1([O-])CCc2ccc(NC(=O)C3(NC(=O)c4ccc(Cl)s4)CCCC3)cc2CC1]

A mixture of 0.20 g (0.46 mmol) 1-[(5-chloro-thiophen-2-yl)-carbonylamino]-N-(3-methyl-2,3,4,5-tetrahydro-1H-benzo[d]azepin-7-yl)-cyclopentane-1-carboxylic acid amide, 0.12 ml 70% meta-chloroperbenzoic acid and 10.0 ml chloroform are stirred for 2 h at room temperature. The mixture is diluted with water and a few drops of 2 N NaOH and ethyl acetate. The mixture is kept overnight in the freezer, and after thawing a crystalline layer is found between the two phases, which is filtered off and dried.

R$_t$ value: 3.14 min (HPLC-MS; method 4)
C$_{22}$H$_{26}$ClN$_3$O$_3$S (447.98)
Mass spectrum: (M+H)⁺=448/450 (chlorine isotopes)

Example 159

5-chloro-thiophene-2-carboxylic acid-N-[1-(7-ben-zyl-6,7,8,9-tetrahydro-5H-pyrimido[4.5-d]azepin-2-ylcarbamoyl)-1-methyl-ethyl]-amide

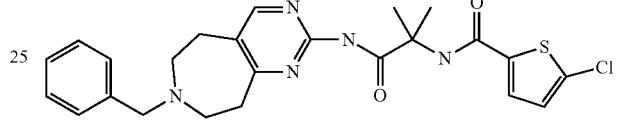

(a) 1-benzyl-5-chloro-azepan-4-carbaldehyde 310 ml (4 mol) DMF are taken and at 10-20° C. 273 ml (3 mol) phosphorus oxychloride are added dropwise thereto over a period of 40 min, then the mixture is stirred for 30 min and then combined with 400 ml dichloromethane and 239.7 g (1 mol) 1-benzyl-hexahydro-4H-azepinone and stirred for 4 h. It is poured onto 3 l of ice water and stirred for 30 min, after which it is extracted with dichloromethane. The organic phase is dried and concentrated by evaporation i.vac., then the crude product is triturated with acetone.

Yield: 177.8 g (62%)

R$_f$ value: 0.69 (silica gel: dichloromethane/ethyl acetate/ethanol=4:2:0.1)

C$_{14}$H$_{16}$ClNO (249.74)

(b) 7-benzyl-6,7,8,9-tetrahydro-5H-pyrimido[4,5-d]azepin-2-ylamine 4.60 g (0.20 mol) sodium are dissolved in 250 ml of ethanol and at room temperature combined with 5.90 g (0.10 mmol) guanidine hydrochloride and 24.97 g (0.10 mol) 1-benzyl-5-chloro-azepan-4-carbaldehyde. Then the mixture is refluxed for 5 h, then stirred for 15 h at room temperature. It is then concentrated by evaporation i.vac., combined with 500 ml dichloromethane and washed 3 times with 400 ml of water. It is purified by chromatography through silica gel (eluant: dichloromethane/methanol 95:5), concentrated by evaporation i.vac. And triturated with ethanol.

Yield: 1.97 g (8%)

C$_{15}$H$_{18}$N$_4$ (254.33)

Mass spectrum: (M+H)⁺=255

(c) 5-chloro-thiophene-2-carboxylic acid-N-[1-(7-benzyl-6,7,8,9-tetrahydro-5H-pyrimido[4.5-d]azepin-2-ylcarbamoyl)-1-methyl-ethyl]-amide 0.63 g (2.75 mmol) 2-(5-chloro-thiophen-2-yl)-4,4-dimethyl-4H-oxazol-5-one and 0.70 g (2.75 mmol) 7-benzyl-6,7,8,9-tetrahydro-5H-pyrimido[4.5-d]azepin-2-ylamine are suspended in 0.350 ml glacial acetic acid, 3.15 ml of toluene and 3.5 ml DMF and stirred for 20 h at 110° C. The mixture is separated by chromatography through silica gel (eluant: dichloromethane/ethanol 100:0=>93:7). Then it is combined with ethyl acetate and washed with 5% sodium hydrogen carbonate solution and water, dried with sodium sulphate and concentrated by evaporation i.vac.

Yield: 0.20 g (15%)
$R_f$ value: 0.5 (silica gel; dichloromethane/ethanol=90:10)
$C_{24}H_{26}ClN_5O_2S$ (484.01)
Mass spectrum: $(M-H)^-$=482/4 (chlorine isotopes)

Example 160

5-chloro-thiophene-2-carboxylic acid-N-[1-methyl-1-(6,7,8,9-tetrahydro-5H-pyrido[2,3-d]azepin-2-ylcarbamoyl)-ethyl]-amide

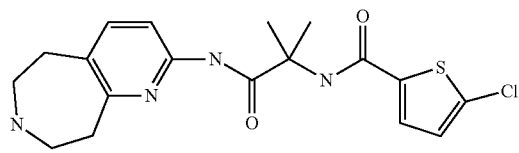 [SMILES: CC(C)(NC(=O)c1ccc(Cl)s1)C(=O)Nc1ccc2c(n1)CCNCC2]

(a) 6,7,8,9-tetrahydro-5H-pyrido[2,3-d]azepin-2-ylamine 1.2 g (3.68 mmol) 7-benzyl-6,7,8,9-tetrahydro-5H-pyrido[2,3-d]azepin-2-ylamine are dissolved in 20 ml of methanol and combined with 0.12 g palladium oxide. The mixture is hydrogenated in a Parr apparatus at 50° C. at 1 bar hydrogen pressure. Then the catalyst is filtered off and the filtrate is concentrated by evaporation i.vac. It is recrystallised from methanol.

Yield: 0.50 g (57%)
$R_f$ value: 0.21 (silica gel; dichloromethane/methanol/ammonia=5:1:0.1)
melting point: 290° C.
$C_9H_{13}N_3$ (163.22)

(b) tert.-butyl 2-amino-5,6,8,9-tetrahydro-pyrido[2,3-d]azepin-7-carboxylate 0.38 g (1.61 mmol) 6,7,8,9-tetrahydro-5H-pyrido[2,3-d]azepin-2-ylamine are suspended in 10 ml dichloromethane, then 0.667 g (4.83 mmol) potassium carbonate are added and the mixture is stirred at room temperature for 10 min. Then 0.369 g (1.69 mmol) BOC-anhydride in 10 ml dichloromethane is slowly added dropwise while cooling with ice, after which the mixture is stirred for 17 h at room temperature, diluted with 20 ml dichloromethane and washed with water. The crude product is dried with sodium sulphate, concentrated by evaporation and purified by chromatography through silica gel (eluant: dichloromethane/ethanol 98:2=>90:10).

Yield: 0.20 g (47%)
$R_f$ value: 0.5 (silica gel; dichloromethane/ethanol=90:10)
$C_{14}H_{21}N_3O_2$ (263.34)

(c) tert-butyl 2-{2-[(5-chloro-thiophen-2-yl)-carbamylamino]-2-methyl-propionylamino}-5,6,8,9-tetrahydro-pyrido[2,3-d]azepine-7-carboxylate Prepared analogously to Example 1(f) from tert.-butyl 2-amino-5,6,8,9-tetrahydro-pyrido[2,3-d]azepine-7-carboxylate and 2-[(5-chloro-thiophen-2-yl)-carbonylamino]-2-methyl-propionic acid with HATU and NMM in DMF at 70° C. and subsequent purification through silica gel (eluant: dichloromethane/ethanol 100:0=>97:3).

Yield: 0.15 g (40%)
$R_f$ value: 0.65 (silica gel; dichloromethane/ethanol=90:10)
$C_{23}H_{29}ClN_4O_4S$ (493.02)

(d) 5-chloro-thiophene-2-carboxylic acid-N-[1-methyl-1-(6,7,8,9-tetrahydro-5H-pyrido[2,3-d]azepin-2-ylcarbamoyl)-ethyl]-amide 0.150 g (0.30 mmol) tert-butyl 2-{2-[(5-chloro-thiophen-2-yl)-carbamylamino]-2-methyl-propionylamino}-5,6,8,9-tetrahydro-pyrido[2,3-d]azepine-7-carboxylate are dissolved at room temperature in 2 ml dichloromethane, combined with 0.40 ml (5.23 mmol) trifluoroacetic acid and stirred for 2 h. Then the mixture is concentrated by evaporation i.vac. And purified by chromatography through RP material (Zorbax StableBond C18, 3.5 µm; eluant: water/acetonitrile/formic acid=80:20:0.1=>10:90:0.1).

Yield: 0.080 g (52%)
$R_f$ value: 0.25 (silica gel; dichloromethane/ethanol/ammonia=90:10:1)
$C_{18}H_{21}ClN_4O_2S$ (392.91)
Mass spectrum: $(M+H)^+$=393/5 (chlorine isotopes)

Example 161

5-chloro-thiophene-2-carboxylic acid-N-[1-methyl-1-(7-methyl-6,7,8,9-tetrahydro-5H-pyrido[2,3-d]azepin-2-ylcarbamoyl)-ethyl]-amide

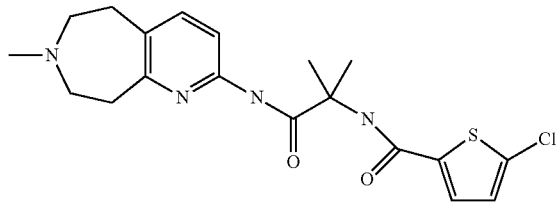 [SMILES: CN1CCc2ccc(NC(=O)C(C)(C)NC(=O)c3ccc(Cl)s3)nc2CC1]

70 mg (0.14 mmol) 5-chloro-thiophene-2-carboxylic acid-N-[1-methyl-1-(6,7,8,9-tetrahydro-5H-pyrido[2,3-d]azepin-2-ylcarbamoyl)-ethyl]-amide are dissolved in 1 ml (26.50 mmol), then 15.0 µl (0.20 mmol) 37% formaldehyde solution in water are added and the mixture is stirred for 3 h at 90° C. Then it is concentrated by evaporation i.vac.

Yield: 40 mg (56%)
$R_f$ value: 0.25 (silica gel; dichloromethane/ethanol/ammonia=80:20:2) $C_{19}H_{23}ClN_4O_2S$ (604.94)
Mass spectrum: $(M+H)^+$=407/9 (chlorine isotopes)

The following compounds may be prepared from amino acid derivatives, benzazepine derivatives and thiophenecarboxylic acid derivatives analogously to the methods of synthesis described in the Examples or known from the literature:

| | | | |
|---|---|---|---|
| 162 | 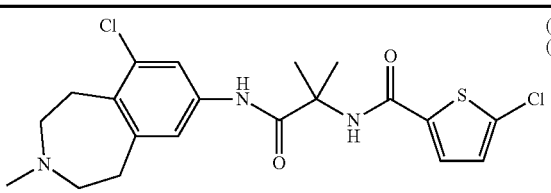<br>5-chloro-thiophene-2-carboxylic acid-N-[1-methyl-1-(3-methyl-9-chloro-2,3,4,5-tetrahydro-1H-benzo[d]azepin-7-ylcarbamoyl]-ethyl}-amide | (M + H)⁺ = 440/4452/444<br>(dichlorine isotope pattern) | Rf: 0.33; RP8;<br>MeOH/5% NaCl<br>solution = 6/4 |
| 163 | 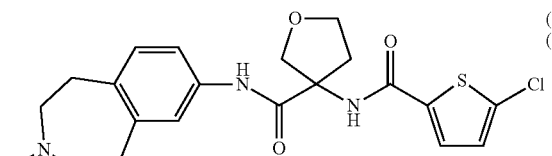<br>3-[(5-chloro-thiophen-2-yl)carbonylamino]-N-(3,5-dimethyl-2,3,4,5-tetrahydro-1H-benzo[d]azepin-7-yl)-tetrahydrofuran-3-carboxylic acid amide | (M + H)⁺ = 448/450<br>(chlorine isotopes) | Rf: 0.75; silica<br>gel;<br>CH₂Cl₂/ethanol/<br>ammonia =<br>80:20:2 |

Example 164

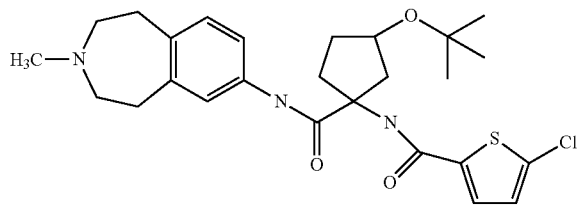 [SMILES: CN1CCc2ccc(NC(=O)C3(NC(=O)c4ccc(Cl)s4)CCC(OC(C)(C)C)C3)cc2CC1]

1-[(5-chloro-thiophen-2-yl)-carbonylamino]-N-(3-methyl-2,3,4,5-tetrahydro-1H-benzo[d]azepin-7-yl)-cyclopentane-3-tert.butoxy-1-carboxylic acid amide Example 165

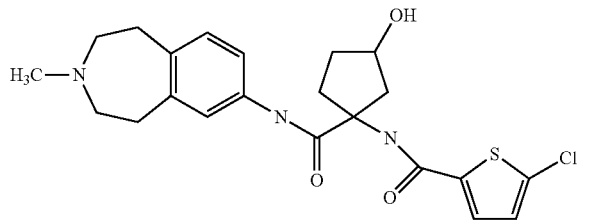 [SMILES: CN1CCc2ccc(NC(=O)C3(NC(=O)c4ccc(Cl)s4)CCC(O)C3)cc2CC1]

1-[(5-chloro-thiophen-2-yl)-carbonylamino]-N-(3-methyl-2,3,4,5-tetrahydro-1H-benzo[d]azepin-7-yl)-cyclopentane-3-hydroxy-1-carboxylic acid amide Example 166

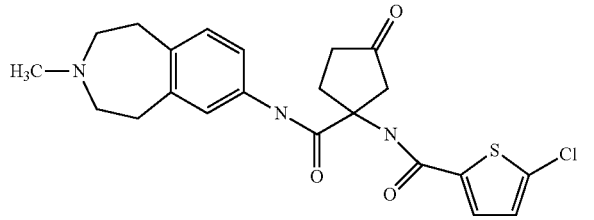 [SMILES: CN1CCc2ccc(NC(=O)C3(NC(=O)c4ccc(Cl)s4)CCC(=O)C3)cc2CC1]

1-[(5-chloro-thiophen-2-yl)-carbonylamino]-N-(3-methyl-2,3,4,5-tetrahydro-1H-benzo[d]azepin-7-yl)-cyclopentane-3-oxo-1-carboxylic acid amide Example 167

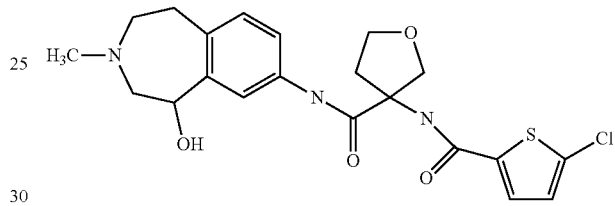

3-[(5-chloro-thiophen-2-yl)-carbonylamino]-N-(3-methyl-5-hydroxy-2,3,4,5-tetrahydro-1H-benzo[d]azepin-7-yl)-tetrahydrofuran-3-carboxylic acid amide Example 168

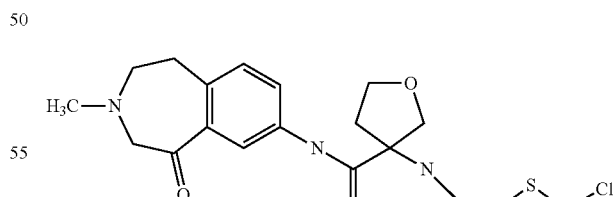

3-[(5-chloro-thiophen-2-yl)-carbonylamino]-N-(3-methyl-5-oxo-2,3,4,5-tetrahydro-1H-benzo[d]azepin-7-yl)-tetrahydrofuran-3-carboxylic acid amide

117

Example 169

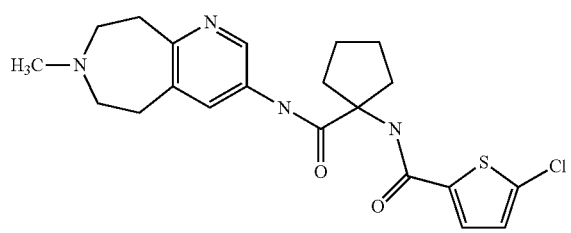 [SMILES: CN1CCc2cc(NC(=O)C3(NC(=O)c4ccc(Cl)s4)CCCC3)cnc2CC1]

1-[(5-chloro-thiophen-2-yl)-carbonylamino]-N-(7-methyl-6,7,8,9-tetrahydro-5H-pyrido[2,3-d]azepin-3-yl)-cyclopentane-1-carboxylic acid amide Example 170

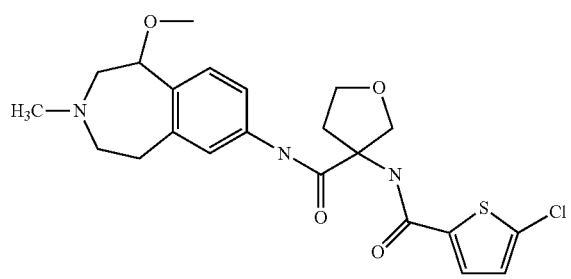 [SMILES: COC1CN(C)CCc2cc(NC(=O)C3(NC(=O)c4ccc(Cl)s4)CCOC3)ccc21]

3-[(5-chloro-thiophen-2-yl)-carbonylamino]-N-(3-methyl-1-methoxy-2,3,4,5-tetrahydro-1H-benzo[d]azepin-7-yl)-tetrahydrofuran-3-carboxylic acid amide Example 171

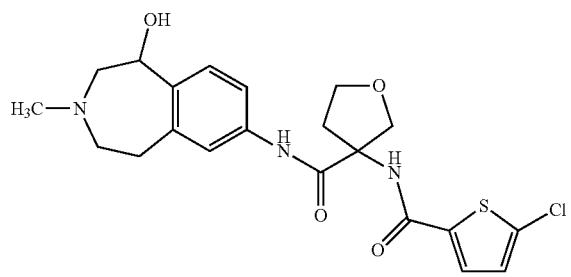 [SMILES: CN1CCc2cc(NC(=O)C3(NC(=O)c4ccc(Cl)s4)CCOC3)ccc2C(O)C1]

3-[(5-chloro-thiophen-2-yl)-carbonylamino]-N-(3-methyl-1-hydroxy-2,3,4,5-tetrahydro-1H-benzo[d]azepin-7-yl)-tetrahydrofuran-3-carboxylic acid amide

118

Example 172

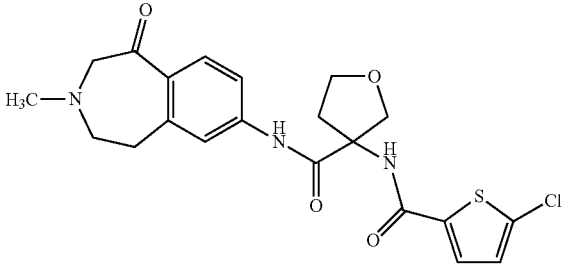 [SMILES: CN1CCc2cc(NC(=O)C3(NC(=O)c4ccc(Cl)s4)CCOC3)ccc2C(=O)C1]

3-[(5-chloro-thiophen-2-yl)-carbonylamino-N-(3-methyl-1-oxo-2,3,4,5-tetrahydro-1H-benzo[d]azepin-7-yl)-tetrahydrofuran-3-carboxylic acid amide Example 173

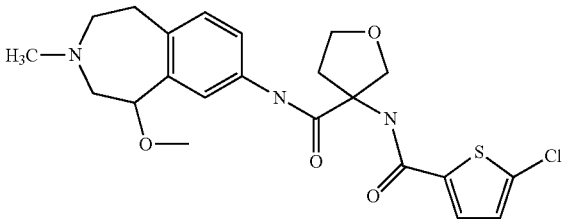 [SMILES: COC1CN(C)CCc2ccc(NC(=O)C3(NC(=O)c4ccc(Cl)s4)CCOC3)cc21]

3-[(5-chloro-thiophen-2-yl)-carbonylamino]-N-(3-methyl-5-methoxy-2,3,4,5-tetrahydro-1H-benzo[d]azepin-7-yl)-tetrahydrofuran-3-carboxylic acid amide Example 174

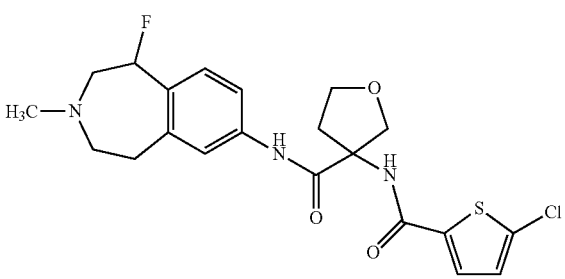 [SMILES: CN1CCc2cc(NC(=O)C3(NC(=O)c4ccc(Cl)s4)CCOC3)ccc2C(F)C1]

3-[(5-chloro-thiophen-2-yl)-carbonylamino]-N-(3-methyl-1-fluoro-2,3,4,5-tetrahydro-1H-benzo[d]azepin-7-yl)-tetrahydrofuran-3-carboxylic acid amide

Example 175

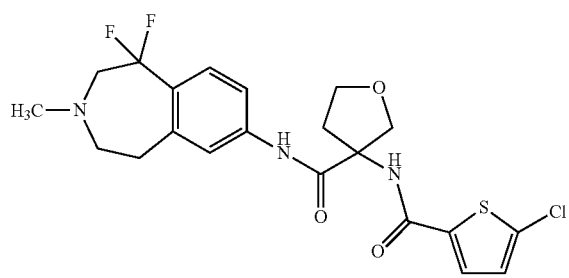 [SMILES: CN1CCc2cc(NC(=O)C3(NC(=O)c4ccc(Cl)s4)CCOC3)ccc2C(F)(F)C1]

3-[(5-chloro-thiophen-2-yl)-carbonylamino]-N-(3-methyl-1,1-difluoro-2,3,4,5-tetrahydro-1H-benzo[d]azepin-7-yl)-tetrahydrofuran-3-carboxylic acid amide

Example 176

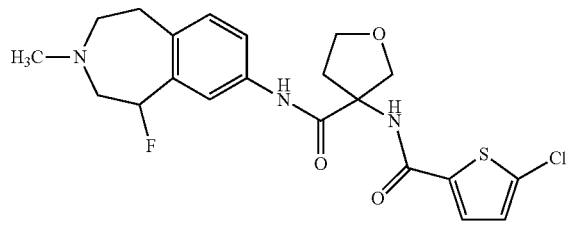 [SMILES: CN1CCc2ccc(NC(=O)C3(NC(=O)c4ccc(Cl)s4)CCOC3)cc2C(F)C1]

3-[(5-chloro-thiophen-2-yl)-carbonylamino]-N-(3-methyl-5-fluoro-2,3,4,5-tetrahydro-1H-benzo[d]azepin-7-yl)-tetrahydrofuran-3-carboxylic acid amide

Example 177

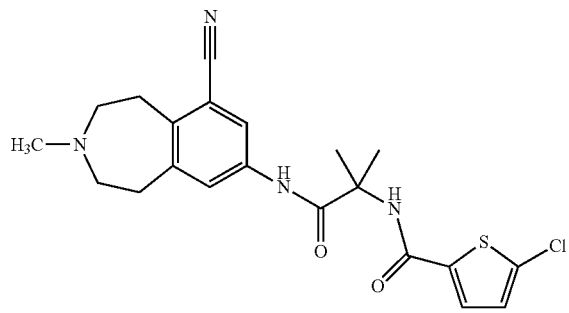 [SMILES: CN1CCc2cc(NC(=O)C(C)(C)NC(=O)c3ccc(Cl)s3)cc(C#N)c2CC1]

5-chloro-thiophene-2-carboxylic acid-N-[1-methyl-1-(3-methyl-9-cyano-2,3,4,5-tetrahydro-1H-benzo[d]azepin-7-ylcarbamoyl]-ethyl}-amide

Example 178

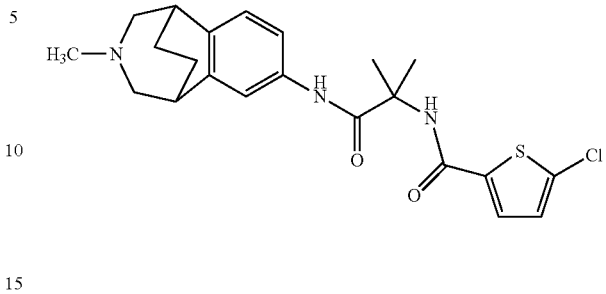

5-chloro-thiophene-2-carboxylic acid-N-[1-methyl-1-(10-methyl-10-aza-tricyclo[6,3,2,02,7]trideca-2(7),3,5-trien-4-ylcarbamoyl]-ethyl}-amide

Example 179

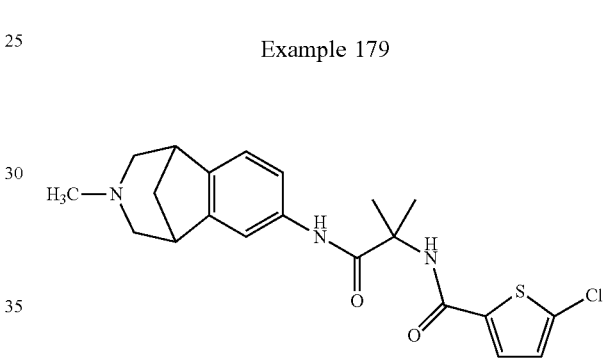

5-chloro-thiophene-2-carboxylic acid-N-[1-methyl-1-(10-methyl-10-aza-tricyclo[6,3,1,02,7]dodeca-2(7),3,5-trien-4-ylcarbamoyl]-ethyl}-amide

Example 180 N

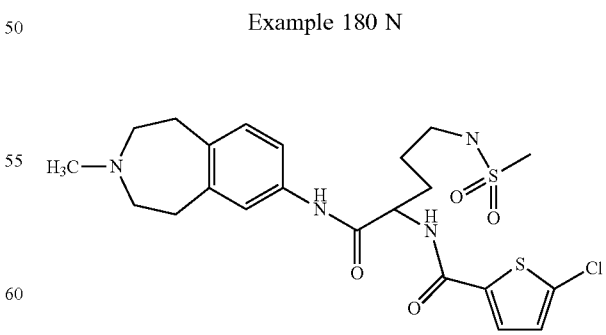

5-chloro-thiophene-2-carboxylic acid-N-[4-methyl-sulphonylamino-1-(3-methyl-2,3,4,5-tetrahydro-1H-benzo[d]azepin-7-ylcarbamoyl)-butyl]-amide

Example 181

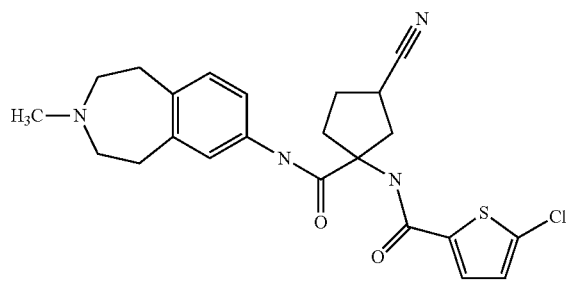 [SMILES: CN1CCc2ccc(NC(=O)C3(NC(=O)c4ccc(Cl)s4)CCC(C#N)C3)cc2CC1]

1-[(5-chloro-thiophen-2-yl)-carbonylamino]-N-(3-methyl-2,3,4,5-tetrahydro-1H-benzo[d]azepin-7-yl)-3-cyano cyclopentane-1-carboxylic acid amide

Example 182

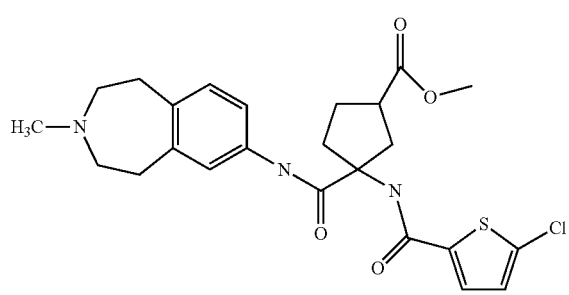 [SMILES: COC(=O)C1CCC(NC(=O)c2ccc(Cl)s2)(C(=O)Nc2ccc3c(c2)CCN(C)CC3)C1]

1-[(5-chloro-thiophen-2-yl)-carbonylamino]-N-(3-methyl-2,3,4,5-tetrahydro-1H-benzo[d]azepin-7-yl)-3-dimethylaminocarbonyl cyclopentane-1-carboxylic acid amide

Example 183

1-[(5-chloro-thiophen-2-yl)-carbonylamino]-N-(3-methyl-2,3,4,5-tetrahydro-1H-benzo[d]azepin-7-yl)-3-methoxycarbonyl cyclopentane-1-carboxylic acid amide

Example 184

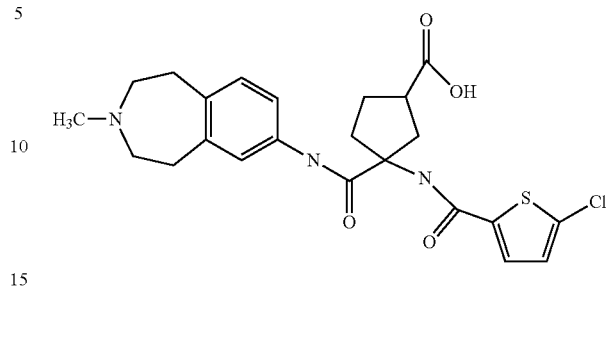

1-[(5-chloro-thiophen-2-yl)-carbonylamino]-N-(3-methyl-2,3,4,5-tetrahydro-1H-benzo[d]azepin-7-yl)-3-hydroxycarbonyl cyclopentane-1-carboxylic acid amide

Example 185

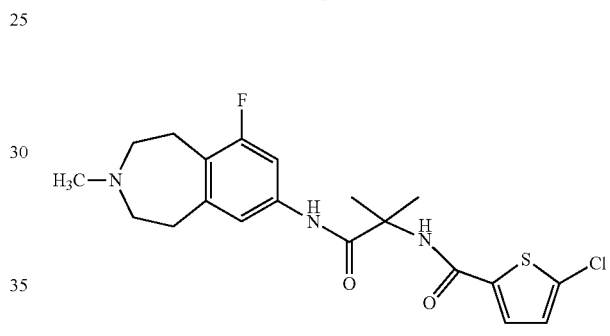

5-chloro-thiophene-2-carboxylic acid-N-[1-methyl-1-(3-methyl-9-cyano-2,3,4,5-tetrahydro-1H-benzo[d]azepin-7-ylcarbamoyl]-ethyl}-amide

Example 186

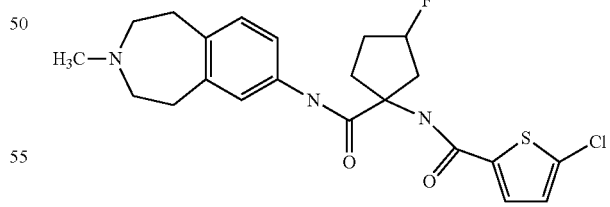

1-[(5-chloro-thiophen-2-yl)-carbonylamino]-N-(3-methyl-2,3,4,5-tetrahydro-1H-benzo[d]azepin-7-yl)-3-cyano cyclopentane-1-carboxylic acid amide The Examples that follow describe the preparation of pharmaceutical formulations which contain as active substance any desired compound of general formula I.

Example A

Dry Ampoule Containing 75 mg of Active Substance Per 10 ml

Composition:

| | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use for injections, the product is dissolved in water.

Example B

Dry Ampoule Containing 35 mg of Active Substance Per 2 ml

Composition:

| | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use for injections, the product is dissolved in water.

Example C

Tablet Containing 50 mg of Active Substance

Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

Example D

Tablet Containing 350 mg of Active Substance

Composition:

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

Example E

Capsules Containing 50 mg of Active Substance

Composition:

| | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

Example F

Capsules Containing 350 mg of Active Substance

Composition:

| | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

Example G

Suppositories Containing 100 mg of Active Substance

| 1 suppository contains: | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylenesorbitan monostearate. At 40° C. the ground active substance is homogeneously dispersed in the melt. It is cooled to 38° C. and poured into slightly chilled suppository moulds.

The invention claimed is:
1. A compound of formula (I), wherein

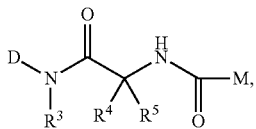

(I)

D denotes a substituted bicyclic ring system of formula (II),

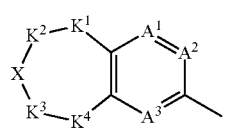

(II)

wherein
$K^1$ and $K^4$
each independently of one another represent a —$CH_2$, —$CHR^{7a}$ or a —$CR^{7b}R^{7c}$— group, wherein
$R^{7a}/R^{7b}/R^{7c}$
each independently of one another denote a $C_{1-2}$-alkyl group or a phenyl group which may be substituted by 1 or 2 substituents selected from among a nitro, amino, hydroxyl, methoxy, cyano, $C_{1-5}$-alkyl group or a fluorine, chlorine or bromine atom,
$K^2$ and $K^3$
each denote a —$CH_2$ group
X denotes an $NR^1$ group, wherein
$R^1$ denotes a hydrogen atom or
a $C_{1-5}$-alkyl, $C_{2-4}$-alkenyl-$CH_2$, $C_{2-4}$-alkynyl-$CH_2$ or $C_{3-6}$-cycloalkyl group,
wherein the methylene and methyl groups present in the previously mentioned $C_{1-5}$-alkyl groups may be substituted by one to three fluorine atoms, as long as the methylene or methyl groups are not directly bound to the nitrogen atom,
and wherein
$A^1$ denotes either N or $CR^{10}$,
$A^2$ denotes either N or $CR^{11}$,
$A^3$ denotes either N or $CR^{12}$,
wherein $R^{10}$, $R^{11}$ and $R^{12}$ each independently of one another represent
a hydrogen, fluorine or chlorine atom, or a $C_{1-3}$-alkyl, $CF_3$, hydroxy or $CH_3O$— group,
or
D denotes one of the groups (II-3) or (II-4)

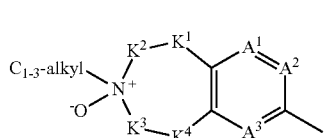

(II-3)

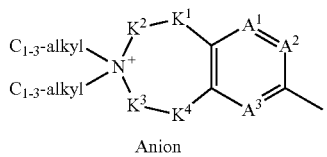

(II-4)

Anion wherein the groups $A^1$, $A^2$, $A^3$, $K^1$, $K^2$, $K^3$, and $K^4$ are as hereinbefore defined, and the anion in (II-4) may be selected from among fluoride, chloride, bromide, iodide, sulphate, phosphate, benzoate, salicylate, succinate, citrate or tartrate, and
$R^3$ denotes a hydrogen atom,
$R^4$ denotes a straight-chain or branched $C_{3-6}$-alkenyl or $C_{3-6}$-alkynyl group,
a straight-chain or branched $C_{1-4}$-alkyl group,
wherein the hydrogen atoms of the straight-chain or branched $C_{1-4}$-alkyl group may optionally be partially replaced by up to four fluorine atoms, and wherein optionally one to two hydrogen atoms may be replaced independently of one another by a $C_{3-7}$-cycloalkyl, hydroxy, $C_{1-5}$-alkyloxy, phenylmethyloxy, $C_{1-5}$-alkylsulphanyl, $C_{1-5}$-alkylsulphinyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-7}$-cycloalkyleneiminocarbonyl, amino, $C_{1-5}$-alkylamino or di-($C_{1-5}$-alkyl)-amino, phenylcarbonylamino, $C_{1-5}$-alkylcarbonylamino, carboxy-$C_{1-5}$-alkylcarbonylamino or a $C_{1-5}$-alkyloxycarbonyl-$C_{1-5}$-alkylcarbonylamino group,
wherein the above-mentioned phenyl groups may be replaced by 1 or 2 substituents selected from fluorine, chlorine, bromine, methyl, methoxy, or trifluoromethyl, or wherein the above-mentioned aminocarbonyl, $C_{1-5}$-alkylaminocarbonyl, phenylcarbonylamino, $C_{1-5}$-alkylcarbonylamino, carboxy-$C_{1-5}$-alkylcarbonylamino or $C_{1-5}$-alkyloxycarbonyl-$C_{1-5}$-alkylcarbonylamino group may optionally be additionally substituted at the nitrogen by a $C_{1-5}$-alkyl group,
a phenyl, phenyl-$C_{1-2}$-alkyl, heteroaryl-$C_{1-2}$-alkyl or C-linked heteroaryl group, wherein the heteroaryl group is selected from among imidazolyl, furanyl, thiophenyl, thiazolyl, pyrazolyl, tetrazolyl, benzimidazolyl, indolyl, pyrimidinyl, pyrazinyl, oxazolyl, and pyridinyl, and which may optionally be mono- to disubstituted in the phenyl or heteroaryl moiety by identical or different substituents selected from among chlorine or fluorine atoms or nitro, $C_{1-3}$-alkyl, $CF_3$, HO, $CH_3O$ or $CHF_2O$— groups,
$R^5$ denotes a hydrogen atom, a straight-chain or branched $C_{1-4}$-alkyl group, a propargyl or $C_{1-3}$-alkyloxy-$C_{1-3}$-alkyl group, or
$R^4$ and $R^5$ together with the carbon atom to which they are bound form a $C_{5-6}$-cycloalkenyl or $C_{3-7}$-cycloalkyl group, wherein one of the methylene groups of the $C_{3-7}$-cycloalkyl group may be replaced by an oxygen or sulphur atom or a sulphonyl group, or 1 to 2 carbon atoms of the $C_{3-7}$-cycloalkyl group may optionally be substituted independently of one another by in each case one or two fluorine atoms, or one or two $C_{1-5}$-alkyl groups, or a hydroxy, $C_{1-5}$-alkyloxy, formyloxy, nitrile, carboxy, $C_{1-5}$-alkyloxycarbonyl, aminocarbonyl, $C_{1-5}$-alkylaminocarbonyl, di-($C_{1-5}$-alkyl)-aminocarbonyl or $C_{4-7}$-cycloalkyleneiminocarbonyl group, with the proviso that when $R^4$ and $R^5$ together form a $C_{3-7}$-cycloalkyl group the methylene groups of said $C_{3-7}$-cycloalkyl group which are linked directly to the carbon atom to which the groups $R^4$ and $R^5$ are bound cannot be replaced by an oxygen or sulphur atom, M denotes a thiophene ring according to formula (III),

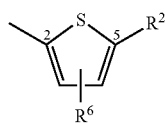

(III)

which is bound to the carbonyl group in formula (I) via the 2-position and is substituted by $R^2$ in the 5-position, where $R^2$ denotes a chlorine or bromine atom or an ethynyl group, and $R^6$ denotes a hydrogen atom, wherein the alkyl, alkenyl, alkynyl and alkyloxy groups contained in the previously mentioned definitions which have more than two carbon atoms may, unless otherwise stated, be straight-chain or branched and the alkyl groups in the previously mentioned dialkylated groups, may be identical or different, with the proviso that the compound of formula

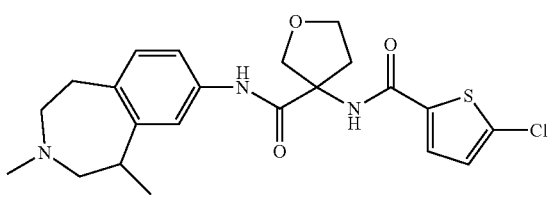 [SMILES: CC1CN(C)CCc2ccc(NC(=O)C3(NC(=O)c4ccc(Cl)s4)CCOC3)cc21]

is excluded, the tautomers, enantiomers, diastereomers, mixtures and salts thereof.

2. The compound of formula (I) according to claim 1, wherein the group

D denotes a substituted bicyclic ring system of formula (II),

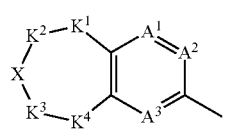

(II)

wherein the groups $K^1$ and $K^4$, $K^2$ and $K^3$ and X are defined according to claim 1, and wherein $R^{7a}/R^{7b}/R^{7c}$ each independently of one another denote a $C_{1-2}$-alkyl group, $R^1$ denotes a hydrogen atom or a $C_{1-5}$-alkyl or $C_{3-6}$-cycloalkyl group, wherein in the methylene and methyl groups present in the above-mentioned groups one to three hydrogen atoms may be replaced by fluorine atoms, provided that the methylene or methyl groups are not directly bound to the nitrogen atom, and wherein $A^1$ denotes $CR^{10}$, $A^2$ denotes $CR^{11}$, $A^3$ denotes $CR^{12}$, wherein $R^{10}$, $R^{11}$ and $R^{12}$ are defined according to claim 1 or

D denotes the group (II-4)

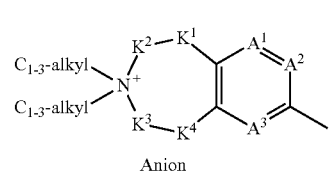

(II-4)

Anion wherein the groups $A^1$, $A^2$, $A^3$, $K^1$, $K^2$, $K^3$, and $K^4$ are as hereinbefore defined, and the anion in (II-4) may be selected from among fluoride, chloride, bromide, iodide, sulphate, phosphate, benzoate, salicylate, succinate, citrate and tartrate, the tautomers, enantiomers, diastereomers, mixtures and salts thereof.

3. The compound of formula (I) according to claim 1, wherein $R^5$ may not represent a hydrogen atom, the tautomers, enantiomers, diastereomers, mixtures and salts thereof.

4. The compound of formula (I) according to claim 1, wherein $R^4$ and $R^5$ together with the carbon atom to which they are bound, form a $C_{5-6}$-cycloalkenyl or $C_{3-7}$-cycloalkyl group, wherein one of the methylene groups of the $C_{3-7}$-cycloalkyl group may be replaced by an oxygen or sulphur atom, with the proviso that the $C_{3-7}$-cycloalkyl group of this kind formed from $R^4$ and $R^5$ together, wherein one of the methylene groups of said $C_{3-7}$-cycloalkyl group, which is linked directly to the carbon atom, to which the groups $R^4$ and $R^5$ are bound, is replaced by an oxygen or sulphur atom, is excluded, the tautomers, enantiomers, diastereomers, mixtures and salts thereof.

5. A physiologically acceptable salt of the compound compounds according to claim 1.

6. A pharmaceutical composition comprising a compound according to claim 1 or a physiologically acceptable salt thereof optionally together with one or more inert carriers and/or diluents.

7. A process for preparing a pharmaceutical composition comprising a compound of claim 1 or a physiologically acceptable salt thereof, wherein said compound or said physiologically acceptable salt thereof is incorporated in one or more inert carriers and/or diluents by a non-chemical method.

8. The compound of formula (I) according to claim 1 selected from
- 3-[(5-bromo-thiophen-2-yl)-carbonylamino]-N-(3-methyl-2,3,4,5-tetrahydro-1H-benzo[d]azepin-7-yl)-tetrahydrofuran-3-carboxylic acid amide,
- 3-[(5-chloro-thiophen-2-yl)-carbonylamino]-N-(3-methyl-2,3,4,5-tetrahydro-1H-benzo[d]azepin-7-yl)-tetrahydrofuran-3-carboxylic acid amide,
- 5-chloro-thiophene-2-carboxylic acid-N-[1-(3-ethyl-2,3,4,5-tetrahydro-1H-benzo[d]azepin-7-ylcarbamoyl)-1-methyl-ethyl]-amide,
- 5-ethynyl-N-[1-methyl-1-(3-methyl-2,3,4,5-tetrahydro-1H-benzo[d]azepin-7-ylcarbamoyl)-ethyl]-thiophene-2-carboxylic acid amide,
- 5-chloro-thiophene-2-carboxylic acid-N-[1-methyl-1-(3-methyl-2,3,4,5-tetrahydro-1H-benzo[d]azepin-7-ylcarbamoyl]-ethyl}-amide,
- 5-bromo-thiophene-2-carboxylic acid-N-[1-methyl-1-(3-methyl-2,3,4,5-tetrahydro-1H-benzo[d]azepin-7-ylcarbamoyl]-ethyl}-amide,
- 5-chloro-thiophene-2-carboxylic acid-N-[2-methoxy-1-(3-methyl-2,3,4,5-tetrahydro-1H-benzo[d]azepin-7-ylcarbamoyl)-ethyl]-amide,
- 1-[(5-bromo-thiophen-2-yl)-carbonylamino]-N-(3-methyl-2,3,4,5-tetrahydro-1H-benzo[d]azepin-7-yl)-cyclopentane-1-carboxylic acid amide,
- 1-[(5-chloro-thiophen-2-yl)-carbonylamino]-N-(3-methyl-2,3,4,5-tetrahydro-1H-benzo[d]azepin-7-yl)-cyclopentane-1-carboxylic acid amide,
- 3-[(5-chloro-thiophen-2-yl)-carbonylamino]-N-(3-methyl-2,3,4,5-tetrahydro-1H-benzo[d]azepin-7-yl)-tetrahydrothiophene-3-carboxylic acid amide,
- 1-[(5-chloro-thiophen-2-yl)carbonylamino]-N-(3-methyl-2,3,4,5-tetrahydro-1H-benzo[d]azepin-7-yl)-cyclobutane-1-carboxylic acid amide,
- 1-[(5-bromo-thiophen-2-yl)carbonylamino]-N-(3-methyl-2,3,4,5-tetrahydro-1H-benzo[d]azepin-7-yl)-cyclopent-3-ene-1-carboxylic acid amide,
- 1-[(5-chloro-thiophen-2-yl)carbonylamino]-N-(3-methyl-2,3,4,5-tetrahydro-1H-benzo[d]azepin-7-yl)-cyclohexane-1-carboxylic acid amide,
- (R)-5-chloro-thiophene-2-carboxylic acid-N-[2-benzyloxy-1-(3-methyl-2,3,4,5-tetrahydro-1H-benzo[d]azepin-7-ylcarbamoyl)-ethyl]-amide,
- 5-chloro-thiophene-2-carboxylic acid-N-[2-benzyloxy-1-methyl-1-(3-methyl-2,3,4,5-tetrahydro-1H-benzo[d]azepin-7-ylcarbamoyl)-ethyl]-amide,
- (R)-5-chloro-thiophene-2-carboxylic acid-N-[2-hydroxy-1-methyl-1-(3-methyl-2,3,4,5-tetrahydro-1H-benzo[d]azepin-7-ylcarbamoyl)-ethyl]-amide,
- 5-bromo-thiophene-2-carboxylic acid-N-[3-hydroxy-1-methyl-1-(3-methyl-2,3,4,5-tetrahydro-1H-benzo[d]azepin-7-ylcarbamoyl)-propyl]-amide,
- 5-chloro-thiophene-2-carboxylic acid-N-[1-methyl-3-dimethylaminocarbonyl-1-(3-methyl-2,3,4,5-tetrahydro-1H-benzo[d]azepin-7-ylcarbamoyl)-propyl]-amide,
- 5-chloro-thiophene-2-carboxylic acid-N-[2-(4-hydroxyphenyl)-1-methyl-1-(3-methyl-2,3,4,5-tetrahydro-1H-benzo[d]azepin-7-ylcarbamoyl)-ethyl]-amide,
- 5-chloro-thiophene-2-carboxylic acid-N-[1-methyl-1-(3,5-dimethyl-2,3,4,5-tetrahydro-1H-benzo[d]azepin-7-ylcarbamoyl)-ethyl]-amide,
- 5-chloro-thiophene-2-carboxylic acid-N-{1-methyl-1-[3-methyl-5-(4-aminophenyl)-2,3,4,5-tetrahydro-1H-benzo[d]azepin-7-ylcarbamoyl]-ethyl}-amide,
- 5-chloro-thiophene-2-carboxylic acid-N-[2-ethoxy-1-(3-methyl-2,3,4,5-tetrahydro-1H-benzo[d]azepin-7-ylcarbamoyl)-ethyl]-amide,
- 5-chloro-thiophene-2-carboxylic acid-N-[3-methoxy-1-(3-methyl-2,3,4,5-tetrahydro-1H-benzo[d]azepin-7-ylcarbamoyl)-propyl]-amide,
- 5-chloro-thiophene-2-carboxylic acid-N-[2-isopropyloxy-1-(3-methyl-2,3,4,5-tetrahydro-1H-benzo[d]azepin-7-ylcarbamoyl)-ethyl]-amide,
- (R)-5-chloro-thiophene-2-carboxylic acid-N-[3-benzyloxy-1-(3-methyl-2,3,4,5-tetrahydro-1H-benzo[d]azepin-7-ylcarbamoyl)-propyl]-amide,
- 1-[(5-chloro-thiophen-2-yl)-carbonylamino]-3,4-dimethoxy-N-(3-methyl-2,3,4,5-tetrahydro-1H-benzo[d]azepin-7-yl)-cyclopentane-1-carboxylic acid amide,
- 5-chloro-thiophene-2-carboxylic acid-N—[C-(1-methylpyrazol-3-yl)-C-(3-methyl-2,3,4,5-tetrahydro-1H-benzo[d]azepin-7-ylcarbamoyl)-methyl]-amide,
- (R)-5-chloro-thiophene-2-carboxylic acid-N-[2-phenyl-1-(3-methyl-2,3,4,5-tetrahydro-1H-benzo[d]azepin-7-ylcarbamoyl)-ethyl]-amide,
- (R)-5-chloro-thiophene-2-carboxylic acid-N-[2-(furan-2-yl)-1-(3-methyl-2,3,4,5-tetrahydro-1H-benzo[d]azepin-7-ylcarbamoyl)-ethyl]-amide,
- 5-chloro-thiophene-2-carboxylic acid-N-[2-(4-methoxyphenyl)-1-(3-methyl-2,3,4,5-tetrahydro-1H-benzo[d]azepin-7-ylcarbamoyl)-ethyl]-amide,
- 5-chloro-thiophene-2-carboxylic acid-N-[2-(4-hydroxy-3-nitro-phenyl)-1-(3-methyl-2,3,4,5-tetrahydro-1H-benzo[d]azepin-7-ylcarbamoyl)-ethyl]-amide,
- (R)-5-chloro-thiophene-2-carboxylic acid-N-[2-(4-hydroxy-phenyl)-1-(3-methyl-2,3,4,5-tetrahydro-1H-benzo[d]azepin-7-ylcarbamoyl)-ethyl]-amide,
- (R)-5-chloro-thiophene-2-carboxylic acid-N-[2-cyclohexyl-1-(3-methyl-2,3,4,5-tetrahydro-1H-benzo[d]azepin-7-ylcarbamoyl)-ethyl]-amide,
- (R)-5-chloro-thiophene-2-carboxylic acid-N-[3-aminocarbonyl-1-(3-methyl-2,3,4,5-tetrahydro-1H-benzo[d]azepin-7-ylcarbamoyl)-propyl]-amide,
- (R)-5-chloro-thiophene-2-carboxylic acid-N-[2-acetylamino-1-(3-methyl-2,3,4,5-tetrahydro-1H-benzo[d]azepin-7-ylcarbamoyl)-ethyl]-amide,
- (R)-5-bromo-thiophene-2-carboxylic acid-N-[2-benzoylamino-1-(3-methyl-2,3,4,5-tetrahydro-1H-benzo[d]azepin-7-ylcarbamoyl)-ethyl]-amide,
- (R)-5-chloro-thiophene-2-carboxylic acid-N-[2-(2-hydroxycarbonyl-ethyl)carbonylamino-1-(3-methyl-2,3,4,5-tetrahydro-1H-benzo[d]azepin-7-ylcarbamoyl)-ethyl]-amide,
- (R)-5-chloro-thiophene-2-carboxylic acid-N-[2-(4-methoxycarbonyl-butyl)carbonylamino-1-(3-methyl-2,3,4,5-tetrahydro-1H-benzo[d]azepin-7-ylcarbamoyl)-ethyl]-amide,
- 5-chloro-thiophene-2-carboxylic acid-N-[1-methyl-1-(3,3-dimethyl-2,3,4,5-tetrahydro-1H-benzo[d]azepinium-7-ylcarbamoyl)-ethyl}-amide iodide, and the tautomers, enantiomers, diastereomers, mixtures and salts thereof.

* * * * *